US011136588B2

(12) United States Patent
Kim et al.

(10) Patent No.: US 11,136,588 B2
(45) Date of Patent: *Oct. 5, 2021

(54) METHOD FOR PRODUCING WHOLE PLANTS FROM PROTOPLASTS

(71) Applicants: INSTITUTE FOR BASIC SCIENCE, Daejeon (KR); SEOUL NATIONAL UNIVERSITY R&DB FOUNDATION, Seoul (KR); AICT, Suwon-si (KR)

(72) Inventors: Jin Soo Kim, Seoul (KR); Jungeun Kim, Seoul (KR); Sunghwa Choe, Gimpo-si (KR); Je Wook Woo, Daejeon (KR); Soon Il Kwon, Gunpo-si (KR)

(73) Assignees: INSTITUTE FOR BASIC SCIENCE, Daejeon (KR); SEOUL NATIONAL UNIVERSITY R&DB FOUNDATION, Seoul (KR); AICT, Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/766,432

(22) PCT Filed: Oct. 6, 2016

(86) PCT No.: PCT/KR2016/011217
§ 371 (c)(1),
(2) Date: Apr. 6, 2018

(87) PCT Pub. No.: WO2017/061806
PCT Pub. Date: Apr. 13, 2017

(65) Prior Publication Data
US 2018/0312869 A1  Nov. 1, 2018

(30) Foreign Application Priority Data

Oct. 6, 2015  (KR) .................. 10-2015-0140314

(51) Int. Cl.
*C12N 15/82* (2006.01)
*C12N 9/22* (2006.01)
*C12N 15/11* (2006.01)

(52) U.S. Cl.
CPC ........... *C12N 15/8213* (2013.01); *C12N 9/22* (2013.01); *C12N 15/11* (2013.01); *C12N 15/8206* (2013.01); *C12N 15/8207* (2013.01); *C12N 15/8298* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 6,977,297 B1 | 12/2005 | Mithen |
| 8,008,542 B2* | 8/2011 | Wang .................. C07K 14/415 |
| | | 800/278 |
| 2009/0013433 A1 | 1/2009 | Wang et al. |
| 2014/0295556 A1 | 10/2014 | Joung et al. |
| 2015/0071903 A1 | 3/2015 | Liu et al. |
| 2016/0145631 A1* | 5/2016 | Voytas ............... C12N 15/8213 |
| | | 800/295 |

FOREIGN PATENT DOCUMENTS

| CN | 102618554 | 8/2012 | |
| CN | 103343120 | 10/2013 | |
| JP | 04502860 | 5/1992 | |
| JP | 6154856 | 6/2017 | |
| KR | WO 2014/065596 | * 5/2014 | ............ C12N 15/11 |
| KR | 20160011216 | 1/2016 | |
| WO | 2014066596 | 5/2014 | |
| WO | 2014/194190 | 12/2014 | |
| WO | 2014/199358 | 12/2014 | |
| WO | 2017/061805 | 4/2017 | |

OTHER PUBLICATIONS

Liang et al. Targeted mutagenesis in *Zea mays* using TALENs and the CRISPR/Cas system. J Genet Genomics. Feb. 20, 2014;41(2):63-8. Epub Dec. 14, 2013. (Year: 2014).*
Jiang et al. The Intrinsically Disordered Protein BKI1 Is Essential for Inhibiting BRI1 Signaling in Plants. Mol Plant. Nov. 2, 2015;8(11):1675-8. Epub Aug. 18, 2015. (Year: 2015).*
Li et al. Cas9-based Genome Editing in *Arabidopsis* and Tobacco. Methods Enzymol. 2014;546:459-72. (Year: 2014).*
Mae et al. Internalisation of Cell-Penetrating Peptides Into Tobacco Protoplasts. Biochim. Biophys. Acta. May 20, 2005;1669(2):101-7. (Year: 2005).*
Chupeau et al. Transgenic Plants of Lettuce (*Lactuca sativa*) Obtained Through Electroporation of Protoplasts. Bio/Technology 7, 503-508 (1989). (Year: 1989).*
Damm et al. Efficient transformation of *Arabidopsis thaliana* using direct gene transfer to protoplasts. Mol. Gen. Genet. May 1989;217(1):6-12. (Year: 1989).*
Gruszka et al. New allele of HvBRI1 gene encoding brassinosteroid receptor in barley. J. Appl. Genet. 2011. Aug. 2011;52(3):257-68. Epub Feb. 8, 2011. (Year: 2011).*
H. Kim et al., "A guide to genome engineering with programmable nucleases", Nature Reviews, Genetics, vol. 15, pp. 321-334, 2014.
H. D. Jones, "Regulatory uncertainty over genome editing", Nature Plants, vol. 1, No. 14011, 2015.
S. Kim et al., "Highly efficient RNA-guided genome editing in human cells via delivery of purified Cas9 ribonucleoproteins", Genome Research, vol. 24, pp. 1012-1019, 2014.
Daniel F. Voytas, "Plant genome engineering with sequence-specific nucleases", Annual Review of Plant Biology, vol. 64, pp. 327-350, Apr. 2013.

(Continued)

*Primary Examiner* — Cynthia E Collins
(74) *Attorney, Agent, or Firm* — Lex IP Meister, PLLC

(57) ABSTRACT

The present invention relates to method for preparing a plant from a protoplast comprising knocking-out or knocking-in one or more the endogenous gene of the protoplast, and the plant regenerated from a genome-modified protoplast prepared by the above method.

9 Claims, 18 Drawing Sheets

Specification includes a Sequence Listing.

(56) References Cited

OTHER PUBLICATIONS

Khaouia Belhaj et al., "Plant genome editing made easy : targeted mutagenesis in model and crop plants using the CRISPR/Cas system", Plant Methods, Biomed Central, London, vol. 9, No. 1, p. 39, Oct. 2013.
Huaxun Ye et al., "Recent Advances in the Regulation of Brassinosteroid Signaling and Biosynthesis Pathways", Journal of Integrative Plant Biology, vol. 53, No. 6, pp. 455-465, Jun. 2011.
Chidananda Nagamangala Kanchiswamy et al., "Non-GMO genetically edited crop plants", Trends in Biotechnology, vol. 33, No. 9, Sep. 2015.
EPO, A copy of European Search Report of EP 16853922 dated Feb. 7, 2019.
Hyun et al. "Site-directed Mutagenesis in *Arabidopsis thaliana* Using Dividing Tissue-targeted RGEN of the CRISPR/Cas System to Generate Heritable Null Alleles", PLANTA, vol. 241, 2015, pp. 271-284, XP035417502.
Yang et al. "The Mechanisms of Brassinosteroids Action: from Signal Transduction to Plant Development", Molecular Plant, vol. 4, No. 4, Jul. 2011, pp. 588-600, XP055373079.
Youbong Hyun et al., "Site-directed mutagenesis in *Arabidopsis thaliana* using dividing tissue-targeted RGEN of the CRISPR/Cas system to generate heritable null alleles", Planta, 241(1), 271-284. doi:10.1007/s00425-014-2180-5.
Cang-Jin Yang et al., "The Mechanisms of Brassinosteroids' Action: From Signal Transduction to Plant Development", Molecular Plant, 4(4), 588-600. doi:10.1093/mp/ssr020.
Serry Koh et al., "T-DNA tagged knockout mutation of rice OsGSKI, an orthologue of *Arabidopsis* BIN2, with enhanced tolerance to various abiotic stresses", Plant Molecular Biology, 65(4), 453-466. doi:10.1007/s11103-007-9213-4.
Kabin Xie et al., "RNA-Guided Genome Editing in Plants Using a CRISPR-Cas System", Molecular Plant, 6(6), 1975-1983. doi:10.1093/mp/sst119.
Seung Woo Cho et al., "Heritable Gene Knockout in Caenorhabditis elegans by Direct Injection of Cas9-sgRNA Ribonucleoproteins", Genetics,2013—vol. 195,p. 1177-1180.
Sojung Kim et al., "Highly efficient RNA-guided genome editing in human cells via delivery of purified Cas9 ribonucleoproteins", Genome Res.,2014—1019 , vol. 24, p. 1012-1019.
Helmut Maucher et al., "The allene oxide cyclase of barley (*Hordeum vulgare* L.) cloning and organ-specific expression", Phytochemistry,2004—811, vol. 65,p. 801-811.
Anonymous, "Intracellular signal transduction mechanism of plant photoreceptor phytochrome", Photosynthetic research, 2008, vol. 18,p. 16-23.
Anonymous, "10. P450 for higher plants: Molecular diversity and gene expression.", Chemical and biological, vol. 37, p. 128-134.
Soon-Hee Kim et al., "Characterization of a Novel DWD Protein that Participates in Heat Stress Response in *Arabidopsis*", Mol. Cells,2014—vol. 37,p. 833-840.
INPI, Office Action of BR 11 2018 007070 0 dated Mar. 3, 2020.
JPO, Office Action of JP 2018-538510 dated Mar. 24, 2020.
Takayuki Mizutani et al., "Plant Regeneration and Cell Fusion of Protoplasts from Lettuce Cultivars and Related Wild Species in Japan", Saga University Agriculture Department bulletin, 1989, 67, pp. 109-118.
Fujimoto, Y. et al., "Production of somatic hybrid plants between cultivars in *Lactuca sativa* through electrofusion", Breeding Magazine, 1988, vol. 38 (Extra vol. 2), pp. 52-53.
JPO, Office Action of JP 2018-538510 dated Jul. 17, 2019.
KIPO, Office Action of KR 10-2016-0129377 dated Jul. 3, 2019.
JPO, Notice of Allowance of the corresponding JP patent application No. 2018-538510, dated Jul. 6, 2021.
Je Wook Woo et al., "DNA-free genome editing in plants with preassembled CRISPR-Cas9 ribonucleoproteins", Nature Biotechnology, vol. 33, p. 1162-1165, Oct. 19, 2015.

\* cited by examiner

[Fig1. a]
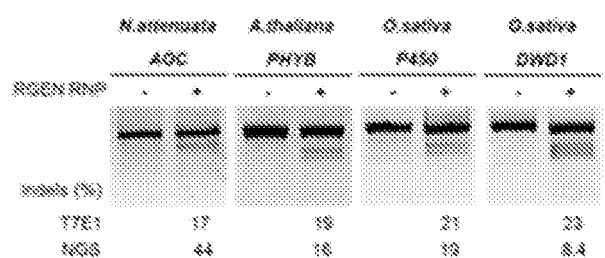

[Fig1. b]

*AOC*

| | | |
|---|---|---|
| CAAAAGACTGTCAATTC-CCT▒▒ | (SEQ ID No: 195) | WT |
| CAAAAGACTGTCAATTCACCTTGG | (SEQ ID No: 196) | +1 |
| CAAAAGACTGTCAATTCTCCTTGG | (SEQ ID No: 197) | +1 |
| CAAAAGACTGTCAATTCCCCTTGG | (SEQ ID No: 198) | +1 |
| CAAAAGACTGTCAATT--CCTTGG | (SEQ ID No: 199) | -1 |

*PHYB*

| | | |
|---|---|---|
| CACTAGGAGCAACACCC-AAC▒▒▒ | (SEQ ID No: 200) | WT |
| CACTAGGAGCAACACCCAAACGGG | (SEQ ID No: 201) | +1 |
| CACTAGGAGCAACACC--AACGGG | (SEQ ID No: 202) | -1 |
| CACTAGGAGCAACACCCCAACGGG | (SEQ ID No: 203) | +1 |
| CACTAGGAGCAACAC---AACGGG | (SEQ ID No: 204) | -2 |
| CACTAGGAGCAAC-----AACGGG | (SEQ ID No: 205) | -4 |

*P450*

| | | |
|---|---|---|
| CATATAGTTGGGTCATG-GCA▒▒▒ | (SEQ ID No: 206) | WT |
| CATATAGTTGGGTCAT--GCATGG | (SEQ ID No: 207) | -1 |
| CATATAGTTGGGTC----GCATGG | (SEQ ID No: 208) | -3 |
| CATATAGTTGGGc-----GCATGG | (SEQ ID No: 209) | -4 |
| CATATAGTTGGGT------CATGG | (SEQ ID No: 210) | -5 |

*DWD1-TS1+TS2*

| | | |
|---|---|---|
| TGCATCGTCCAAGCGCACAG▒▒▒CCCGGCCTACGACGTCAGGTTCT-----ACC▒▒▒ | (SEQ ID No: 211) | WT |
| TGCATCGTCCAAGCGC-------------------------------T-----ACCCGG | (SEQ ID No: 212) | -29 |
| TGCATCGTCCAAGCGCACAGTGGCCCGGCCTACGACGTCAGGTTCT(INS)ACCCGG | (SEQ ID No: 213) | +33 |

[Fig1. c]
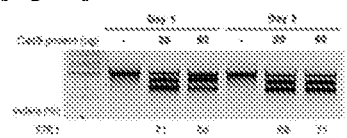
BRI1-TS1+TS2
```
TTTGAAAGATGGAAGCG-CGG   . (201bp).TGAAACTAAACTGGTCC-ACA    (SEQ ID No: 214) WT
TTTGAAAGATGGAAGCG--------------------------------C-ACACGG  (SEQ ID No: 215)-223
```
[Fig. 2a]
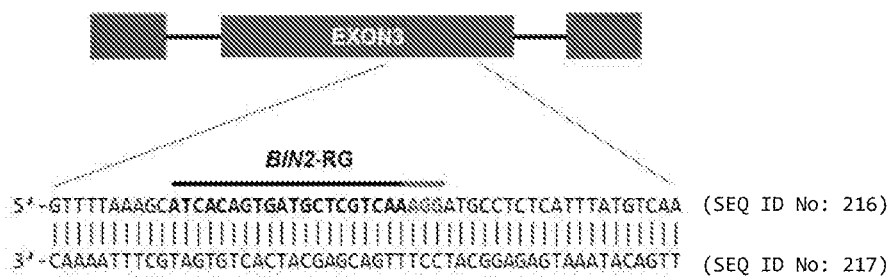
5'-GTTTTAAAGCATCACAGTGATGCTCGTCAAAGGATGCCTCTCATTTATGTCAA (SEQ ID No: 216)
3'-CAAAATTTCGTAGTGTCACTACGAGCAGTTTCCTACGGAGAGTAAATACAGTT (SEQ ID No: 217)

[Fig. 2b]
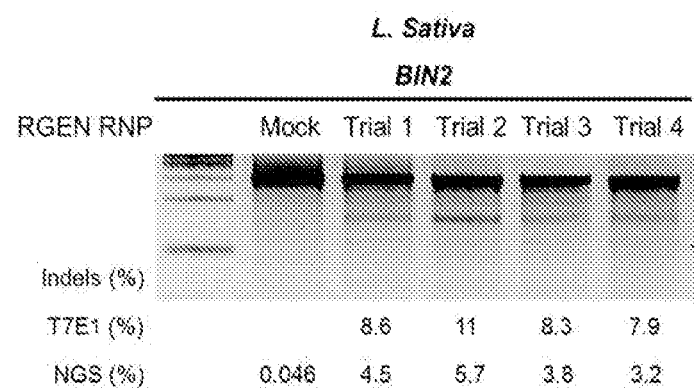

[Fig. 2c]

Trial 1

Mutated locus

```
                                PAM
ATCACAGTGATGCTCGT-CAAAGG  (SEQ ID No: 218)  WT
ATCACAGTGATGCTCGTCCAAAGG  (SEQ ID No: 219)  + 1bp (3.1%)
ATCACAGTGATGCTCG--CAAAGG  (SEQ ID No: 220)  - 1bp (0.26%)
ATCACAGTGATGCTCGTACAAAGG  (SEQ ID No: 221)  + 1bp (0.25%)
ATCACAGTGATGCTCGTTCAAAGG  (SEQ ID No: 222)  + 1bp (0.21%)
```

Trial 2

Mutated locus

```
                                PAM
ATCACAGTGATGCTCGT-CAAAGG  (SEQ ID No: 223)  WT
ATCACAGTGATGCTCGTCCAAAGG  (SEQ ID No: 224)  + 1bp (3.3%)
ATCACAGTGATGCT----CAAAGG  (SEQ ID No: 225)  - 3bp (0.68%)
ATCACAGTGATGCTCGTACAAAGG  (SEQ ID No: 226)  + 1bp (0.37%)
ATCACAGTGATGCTCGTTCAAAGG  (SEQ ID No: 227)  + 1bp (0.26%)
```

Trial 3

Mutated locus

```
                                PAM
ATCACAGTGATGCTCGT-CAAAGG  (SEQ ID No: 228)  WT
ATCACAGTGATGCTCGTCCAAAGG  (SEQ ID No: 229)  + 1bp (2.4%)
ATCACAGTGATGCTCGTACAAAGG  (SEQ ID No: 230)  + 1bp (0.43%)
ATCACAGTGATGCTCGTTCAAAGG  (SEQ ID No: 231)  + 1bp (0.27%)
ATCACAGTGATGCTCGTCCAAAGG  (SEQ ID No: 232)  + 1bp (0.15%)
```

Trial 4

Mutated locus

```
                                PAM
ATCACAGTGATGCTCGT-CAAAGG  (SEQ ID No: 233)  WT
ATCACAGTGATGCTCGTTCAAAGG  (SEQ ID No: 234)  + 1bp (2.2%)
ATCACAGTGATGCTCGTACAAAGG  (SEQ ID No: 235)  + 1bp (0.27%)
ATCACAGTGATGCT----CAAAGG  (SEQ ID No: 236)  - 3bp (0.20%)
ATCACAGTGATGCTCGTTCAAAGG  (SEQ ID No: 237)  + 1bp (0.11%)
```

[Fig.3a]
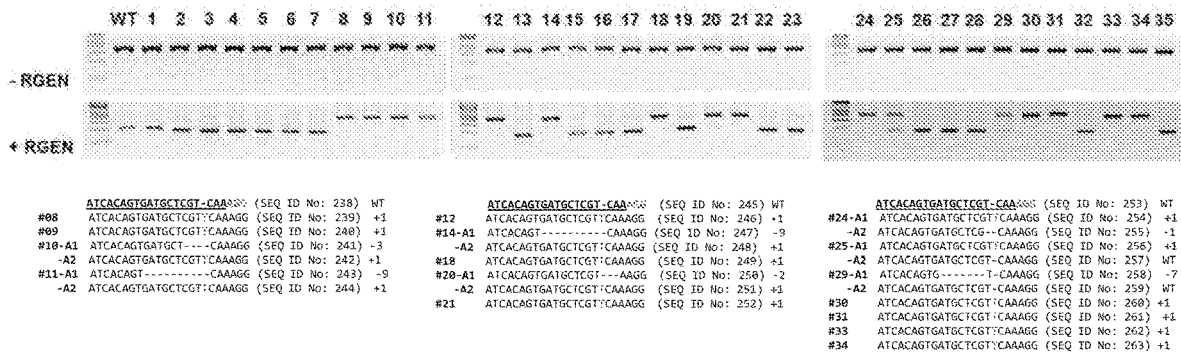
[Fig. 3b]

[Fig. 4a]
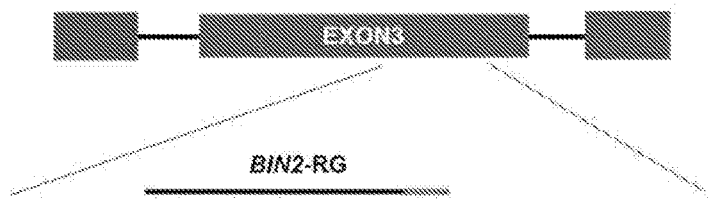
5'-GTTTTAAAGCATCACAGTGATGCTCGTCAAAGGATGCCTCTCATTTATGTCAA (SEQ ID No: 264)
   |||||||||||||||||||||||||||||||||||||||||||||||||||
3'-CAAAATTTCGTAGTGTCACTACGAGCAGTTTCCTACGGAGAGTAAATACAGTT (SEQ ID No: 265)
[Fig. 4b]
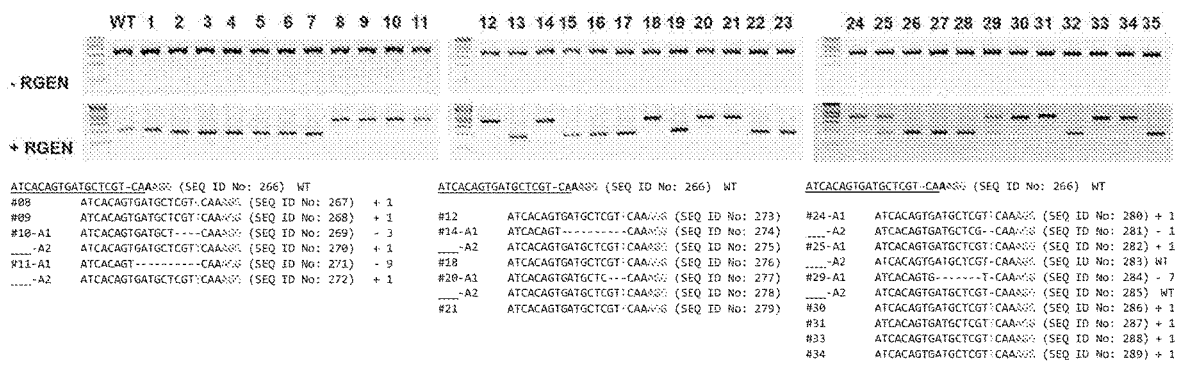

[Fig. 4c]
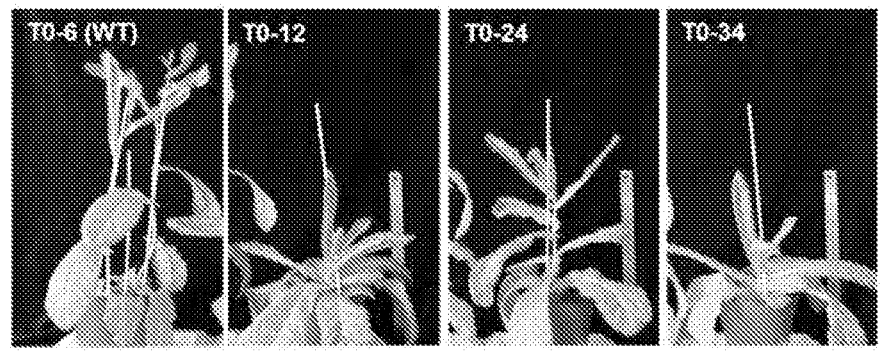

[Fig 5.]
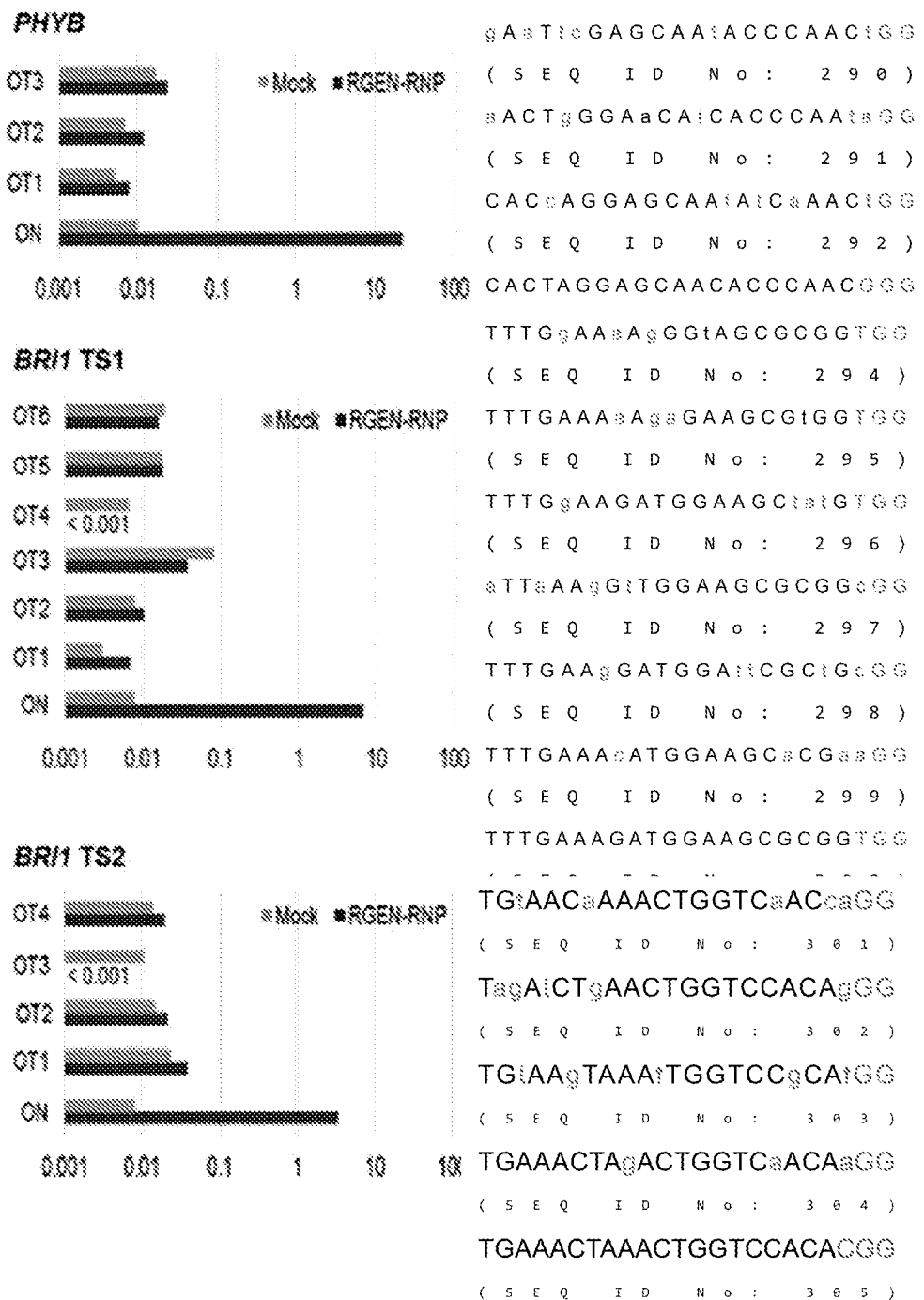

[Fig.6]

<u>GTC ACT GGG CAC ATC ATC TCC AC</u>C ACA ATT GGA GGC AAG AAT GGA GAA CCA AAA CAG ACT
GTG AGT TAC ATG GCA GAG CGT GTG GTA GGG GCT GGA TCT TTT GGA ATT GTT TTC CAG GCA
AAA TGT CTA GAA ACG GGG GAA ACT GTG GCT ATA AAA AAG GTT TTA CAA GAC AAA AGA TAC
AAG AAT CGT GAG TTG CAG TTG ATG AGA ACA ATG GAT CAT CCA AAT GTG GTT TCT TTG AAG
CAT TGT TTC TAT TCA ACT ACA AGC AAA GAT GAG CTT TTT CTC AAT CTG GTT ATG GAA TAT
GTC CCA GAG ACA ATT TTT CGG GTT TTA AAG CAT CAC AGT GAT GCT CGT CAA AGG ATG CCT
CTC ATT TAT GTC AAA CTA TAC ACA TAT CAA ATA TTT AGG GGG CTA GCA TAC ATG CAT ATG
GTT GCT GGA GCA TGC CAC AGG GAC TTG AAG CCT CAG AAT GTC CTG GTT GAT CCT CTT ACT
CAC CAA GTC AAG ATC TGC GAC TTT GGA AGC GCA AAA ATG CTA GTG AGG GGA GAA GCA AAT
ATA TCA TAT ATT TGT TCT CGT TTT TAT CGG GCC CCA GAA CTT ATC TTT GGT GCT ACT GAG
TAT ACA ACT TCG ATT GAT ATA TGG TCG GCT GGT TGC ATT CTT GCT GAG CTT CTT TTG GGG
CAG CCA CTA TTT CCC GGA GAA AAT GCA GTG GAT CAG CTT GTG GAG ATT ATT AAG GTT CTG
GGC ACG CCA ACG CGA GAA GAA CTT CGA TGT ATG AAT CCC AAC TAC ACT GAT TTT AGG TTT
CCT CAA GTA AAG GCA CAC CCT TGG CAC AAG GTA TTT CAT AAG CGG <u>ATG CCC CCG GAA GCG
ATT GAC TTA</u> (SEQ ID No: 306)

<u>VTGHIIST</u>TIGGKNGEPKQTVSYMAERVVGAGSFGIV<u>FQAKCLET</u>GETVAIKKVLQDKRYKNRELQLMRTMDH
PNVVSLKHCFYSTTSKDELFLNLVMEYVPETIFRVLKHHSDARQRMPLIYVKLYTYQIFRGLAYMHMVAGACHR
DLKPQNVLVDPLTHQVKICDFGSAKMLVRGEANISYICSRFYRAPELIFGATEYTTSIDIWSAGCILAELLLGQPL
FPGENAVDQLVEIIKVLGTPTREELRCMNPNYTDFRFPQVKAHPWHKVFHKR<u>MPPEAIDL</u> (SEQ ID No: 307)

[Fig.7]
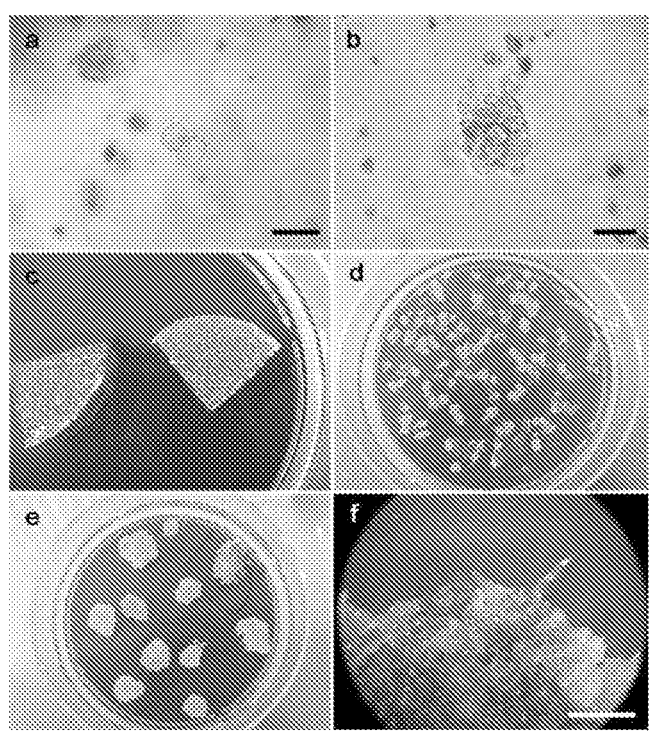

```
                                         PAM
Wild-type ATCACAGTGATGCTCGT-----CAAAGG (SEQ ID No: 308)
          ATCACAGTGATGCTCGT--T--CAAAGG (SEQ ID No: 309)   + 1bp (99.9 %)
```

9

```
                                         PAM
Wild-type ATCACAGTGATGCTCGT-----CAAAGG (SEQ ID No: 310)
          ATCACAGTGATGCTCGT--T--CAAAGG (SEQ ID No: 311)   + 1bp (99.9 %)
```

10

```
                                         PAM
Wild-type ATCACAGTGATGCTCGT-----CAAAGG (SEQ ID No: 312)
          ATCACAGTGATGCTCGT--T--CAAAGG (SEQ ID No: 313)+ 1bp (99.8 %)
```

11

```
                                         PAM
Wild-type ATCACAGTGATGCTCGT-----CAAAGG(SEQ ID No: 314)
          ATCACAGT--------------CAAAGG(SEQ ID No: 315) - 9bp (59.5 %)
          ATCACAGTGATGCTCGT--T--CAAAGG(SEQ ID No: 316)+ 1bp (40.4 %)
```

12

```
                                         PAM
Wild-type ATCACAGTGATGCTCGT-----CAAAGG (SEQ ID No: 317)
          ATCACAGTGATGCTCGT--T--CAAAGG (SEQ ID No: 318)+ 1bp (99.9 %)
```

14

```
                                         PAM
Wild-type ATCACAGTGATGCTCGT-----CAAAGG (SEQ ID No: 319)
          ATCACAGT--------------CAAAGG (SEQ ID No: 320)- 9bp (62.2 %)
          ATCACAGTGATGCTCGT--T--CAAAGG (SEQ ID No: 321)+ 1bp (37.6 %)
```

```
                              PAM
Wild-type  ATCACAGTGATGCTCGT-----CAAAGG  (SEQ ID No: 322)
           ATCACAGTGATGCTCGT-----CAAAGG  (SEQ ID No: 323)    WT (99.1 %)
```

18

```
                              PAM
Wild-type  ATCACAGTGATGCTCGT-----CAAAGG  (SEQ ID No: 324)
           ATCACAGTGATGCTCGT--T--CAAAGG  (SEQ ID No: 325)+  1bp (99.9 %)
```

20

```
                              PAM
Wild-type  ATCACAGTGATGCTCGT-----CAAAGG  (SEQ ID No: 326)
           ATCACAGTGATGCTCGT--T--CAAAGG  (SEQ ID No: 327)+  1bp (53.5 %)
           ATCACAGTGATGCTCGT-------AAGG  (SEQ ID No: 328)-  2bp (46.4 %)
```

21

```
                              PAM
Wild-type  ATCACAGTGATGCTCGT-----CAAAGG  (SEQ ID No: 329)
           ATCACAGTGATGCTCGT--T--CAAAGG  (SEQ ID No: 330)+  1bp (99.8 %)
```

24

```
                              PAM
Wild-type  ATCACAGTGATGCTCGT-----CAAAGG  (SEQ ID No: 331)
           ATCACAGTGATGCTCGT--T--CAAAGG  (SEQ ID No: 332)+  1bp (50.3 %)
           ATCACAGTGATGCTCG------CAAAGG  (SEQ ID No: 333)-  1bp (49.6 %)
```

25

```
                              PAM
Wild-type  ATCACAGTGATGCTCGT-----CAAAGG  (SEQ ID No: 334)
           ATCACAGTGATGCTCGT-----CAAAGG  (SEQ ID No: 335)    WT (50.3 %)
           ATCACAGTGATGCTCGT--T--CAAAGG  (SEQ ID No: 336)+  1bp (49.3 %)
```

```
Wild-type ATCACAGTGATGCTCGT-----CAAAGG (SEQ ID No: 337)
          ATCACAGTGATGCTCGT-----CAAAGG (SEQ ID No: 338)    WT (99.9 %)
```

29

```
Wild-type ATCACAGTGATGCTCGT-----CAAAGG (SEQ ID No: 339)
          ATCACAGTG-------T-----CAAAGG (SEQ ID No: 340)- 7bp (55.9 %)
          ATCACAGTGATGCTCGT-----CAAAGG (SEQ ID No: 341)    WT (43.4 %)
```

30

```
Wild-type ATCACAGTGATGCTCGT-----CAAAGG (SEQ ID No: 342)
          ATCACAGTGATGCTCGT--T--CAAAGG (SEQ ID No: 343) + 1bp (99.9 %)
```

31

```
Wild-type ATCACAGTGATGCTCGT-----CAAAGG (SEQ ID No: 344)
          ATCACAGTGATGCTCGT--T--CAAAGG (SEQ ID No: 345)+ 1bp (99.8 %)
```

33

```
Wild-type ATCACAGTGATGCTCGT-----CAAAGG (SEQ ID No: 346)
          ATCACAGTGATGCTCGT--T--CAAAGG (SEQ ID No: 347)+ 1bp (99.9 %)
```

34

```
Wild-type ATCACAGTGATGCTCGT-----CAAAGG (SEQ ID No: 348)
          ATCACAGTGATGCTCGT--T--CAAAGG+(SEQ ID No: 349) 1bp (99.7 %)
```

[Fig. 9]
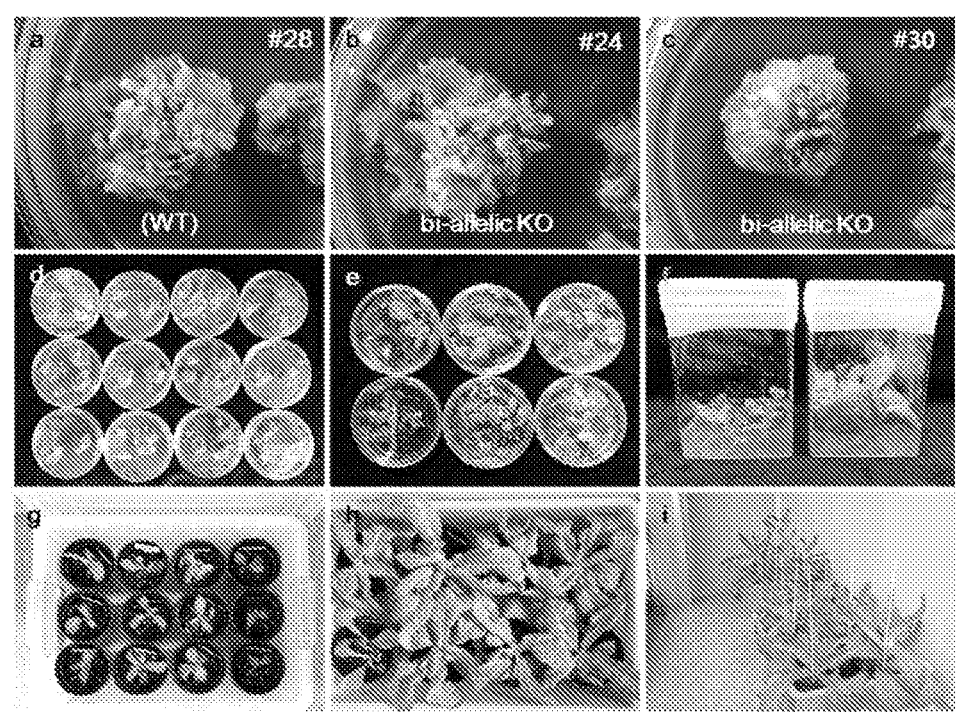

[Fig. 10a]
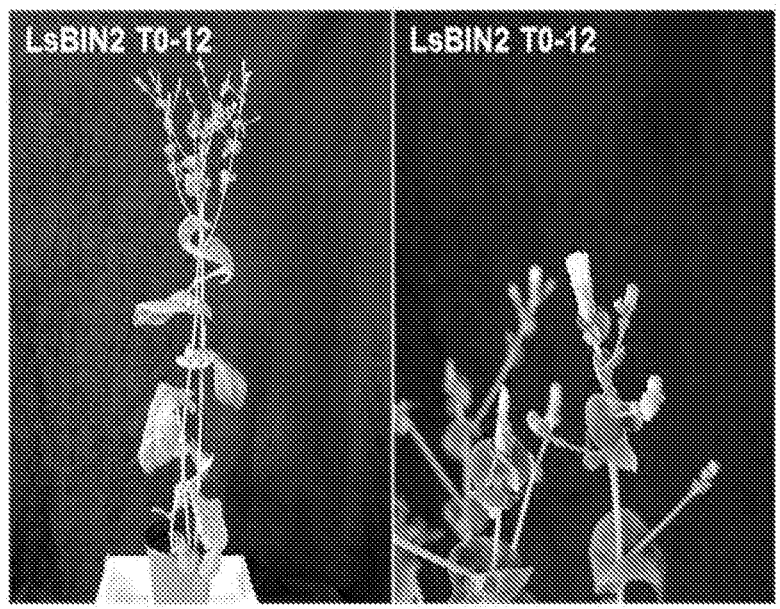

[Fig. 10b]
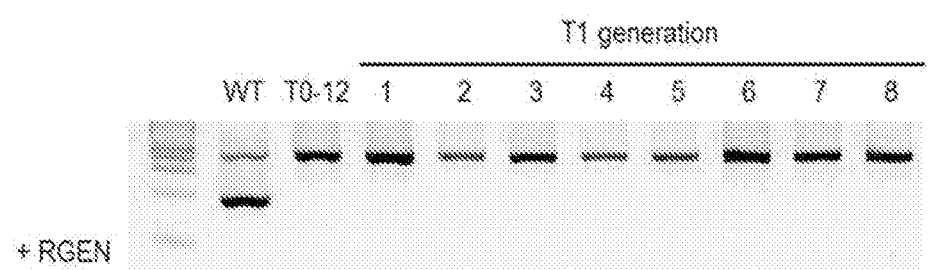

[Fig. 10c]
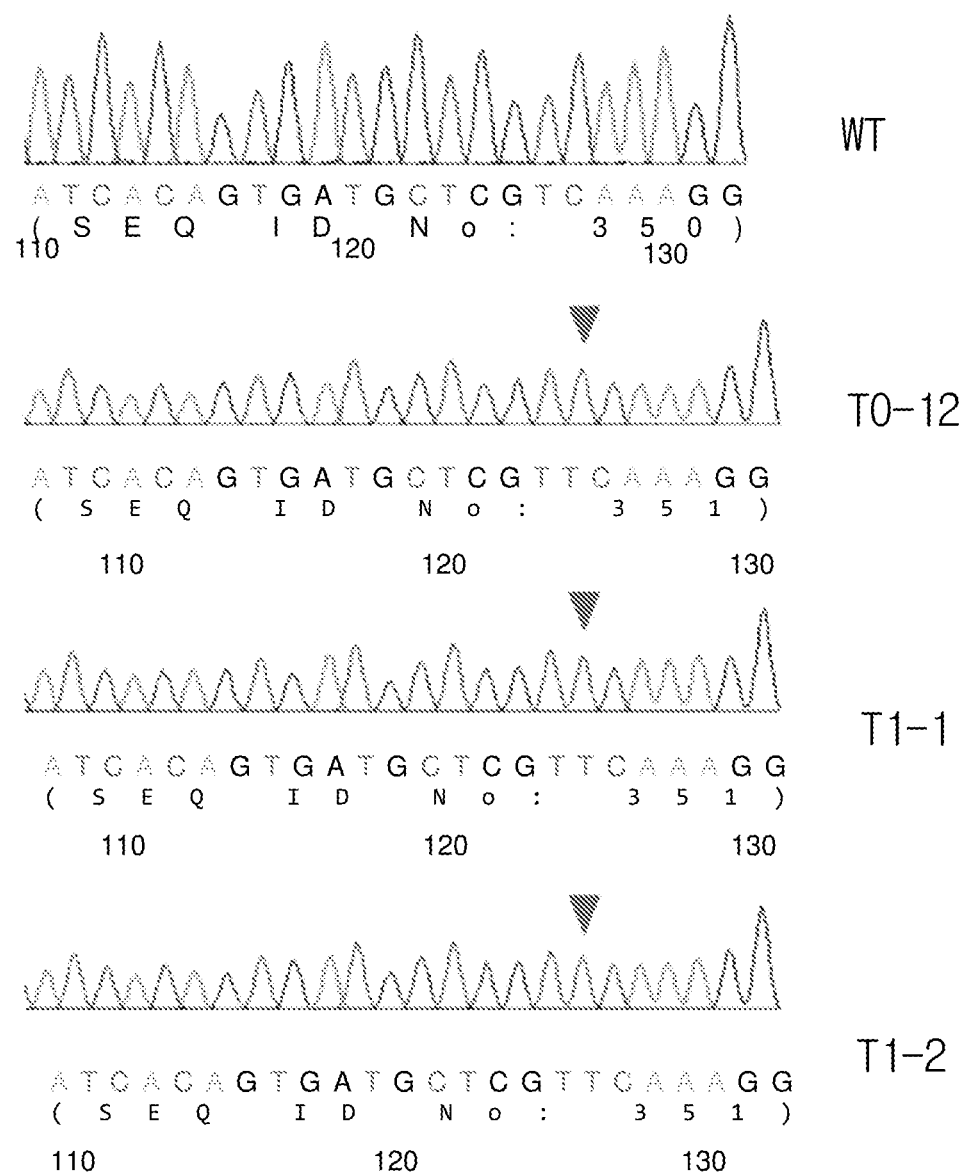

METHOD FOR PRODUCING WHOLE PLANTS FROM PROTOPLASTS

TECHNICAL FIELD

The present invention relates to method for preparing a plant from a protoplast comprising knocking-out or knocking-in one or more the endogenous gene of the protoplast, and the plant regenerated from a genome-modified protoplast prepared by the above method.

BACKGROUND ART

Programmable nucleases, which include zinc-finger nucleases (ZFNs), transcription activator-like effector nucleases (TALENs), and RNA-guided endonucleases (RGENs) repurposed from the type II clustered, regularly-interspaced palindromic repeat (CRISPR)-CRISPR-associated (Cas) adaptive immune system in bacteria and archaea have been successfully used for genome editing in cells and organisms including various plant species, paving the way for novel applications in biomedical research, medicine, and biotechnology (Kim, H. etc., Nat Rev Genet, 2014, 15: 321-334). Among these nucleases, CRISPR RGENs, the latest of the trio of nucleases, are rapidly replacing ZFNs and TALENs, owing to their ease of programmability; RGENs that consist of the Cas9 protein derived from *Streptococcus pyogenes* and guide RNAs (gRNAs) are customized by replacing the RNA component only, sidestepping the labor-intensive and time-consuming protein engineering required for making new TALENs and ZFNs. Programmable nucleases, delivered into plant cells via *Agrobacterium* or transfection of plasmids that encode them, cleave chromosomal target sites in a sequence-dependent manner, producing site-specific DNA double-strand breaks (DSBs). The repair of these DSBs by endogenous systems gives rise to targeted genome modifications.

It remains unclear whether the resulting genome-edited plants will be regulated by genetically-modified organism (GMO) legislation in the EU and other countries (Jones, H. D., Nature Plants, 2015, 1: 14011). Programmable nucleases induce small insertions and deletions (indels) or substitutions at chromosomal target sites that are indistinguishable from naturally-occurring variations. Still, these plants may be considered as GMOs by regulatory authorities in certain countries, hampering widespread use of programmable nucleases in plant biotechnology and agriculture. For example, when *Agrobacterium* is used, genome-edited plants will contain foreign DNA sequences, including those encoding programmable nucleases in the host genome. Removal of these *Agrobacterium*-derived DNA sequences by breeding is not feasible in certain plants such as grape, potato, and banana, owing to their asexual reproduction.

Alternatively, non-integrating plasmids that encode programmable nucleases can be transfected into plant cells such as protoplasts. We note, however, that transfected plasmids are degraded in cells by endogenous nucleases and that the resulting small DNA fragments can be inserted at the Cas9 on-target and off-target sites, as shown in human cells (Kim, S, etc., Genome research, 2014, 24: 1012-1019).

Delivery of preassembled Cas9 protein-gRNA ribonucleoproteins (RNPs) rather than plasmids encoding these components into plant cells could avoid the possibility of inserting recombinant DNA in the host genome. Furthermore, as shown in cultured human cells, RGEN RNPs cleave chromosomal target sites immediately after transfection and are degraded rapidly by endogenous proteases in cells, potentially reducing mosaicism and off-target effects in regenerated whole plants. Preassembled RGEN RNPs can be used broadly across plant species without prior optimization of codon usage and promoters to express Cas9 and gRNAs in each species. In addition, RGEN RNPs enable pre-screening in vitro to choose highly active gRNAs and genotyping of mutant clones via restriction fragment length polymorphism (RFLP) analysis.

To the best of our knowledge, however, RGEN RNPs have never been used in any plant species.

DISCLOSURE OF INVENTION

Technical Problem

It is an object of the present invention to provide a method for preparing a plant from a protoplast comprising knocking-out or knocking-in one or more endogenous genes of the protoplast.

Another object of the present invention is to provide a plant regenerated from a genome-edited protoplast prepared by the method for preparing a plant from a protoplast.

Still another object of the present invention is to provide a composition for cleaving DNA encoding BIN2 gene in a plant cell, comprising: a guide RNA specific to DNA encoding Brassinosteroid Insensitive 2 (BIN2) gene, BKI1 gene, or homologs thereof, or DNA encoding the guide RNA; and a nucleic acid encoding a Cas protein, or a Cas protein.

Still another object of the present invention is to provide a composition for preparing a plant from a protoplast, comprising: a guide RNA specific to DNA encoding Brassinosteroid Insensitive 2 (BIN2) gene, BKI1 gene, or homologs thereof, or DNA encoding the guide RNA; and a nucleic acid encoding a Cas protein or a Cas protein.

Still another object of the present invention is to provide a kit for preparing a plant from a protoplast comprising the composition for preparing a plant from a protoplast.

Solution to Problem

We transfected purified Cas9 protein and guide RNAs into various plant protoplasts, inducing targeted mutagenesis in regenerated plants at frequencies of up to 46%. Cas9 ribonucleoprotein delivery into protoplasts avoided the possibility of inserting foreign DNA in the host genome. The resulting plants contained germline-transmissible, small insertions or deletions at target sites, which are indistinguishable from naturally-occurring variations, possibly bypassing regulatory requirements associated with use of *Agrobacterium* or plasmids.

Advantageous Effects of Invention

In the present invention, we showed that RGEN RNPs can be delivered into protoplasts derived from various plant species and induce targeted genome modifications in whole plants regenerated from them.

BRIEF DESCRIPTION OF DRAWINGS

FIG. 1. RGEN RNP-mediated gene disruption in various plant protoplasts. (a) Mutation frequencies measured by the T7E1 assay and targeted deep sequencing. (b) Mutant DNA sequences induced by RGEN RNPs in plant cells. The PAM sequences are shown in red. Inserted nucleotides are shown in blue. WT, wild-type. (c) A timecourse analysis of genome editing in *Arabidopsis* protoplasts. (Top) The T7E1 assay. (Bottom) DNA sequences of the wild-type (WT) and mutant sequences.

FIG. 2. RGEN RNP-mediated gene disruption in bulk population. (a) The target sequence in the BIN2 gene. The PAM sequence is shown in red. (b) Mutation frequencies measured by the T7E1 assay and targeted deep sequencing in bulk population. (c) Mutant DNA sequences induced by RGEN RNPs in plant cells. The PAM sequences are shown in red. Inserted nucleotides are shown in blue. WT, wild-type.

FIG. 3. Genetic analysis of microcalli derived from a single protoplast treated with RGEN RNP. (a) Genotyping of microcalli. (Top) RGEN RFLP analysis. (Bottom) Mutant DNA sequences in microcalli. (b) Summary of genetic analysis of BIN2 gene in T0 generation.

FIG. 4. Targeted gene knockout in lettuce using an RGEN RNP. (a) The target sequence in the BIN2 gene. The PAM sequence is shown in red. (b) Genotyping of microcalli. (Top) RGEN RFLP analysis. (Bottom) Mutant DNA sequences in microcalli. (c) Whole plants regenerated from RGEN RNP-transfected protoplasts.

FIG. 5. Analysis of off-target effects. Mutation frequencies at on-target and potential off-target sites of the PHYB and BRI1 gene-specific sgRNAs were measured by targeted deep sequencing. About ~80,000 paired-end reads per site were obtained to calculate the indel rate.

FIG. 6. Partial nucleotide and amino acid sequences of LsBIN2. Underscored and boxed letters represent the sequences corresponding to degenerate primers and sgRNA, respectively.

FIG. 7. Regeneration of plantlets from RGEN RNP-transfected protoplast in *L. sativa*. Protoplast division, callus formation and shoot regeneration from RGEN RNP-transfected protoplasts in the lettuce. (a) Cell division after 5 days of protoplast culture (Bar=100 μm). (b) A multicellular colony of protoplast (Bar=100 μm). (c) Agarose-embedded colonies after 4 weeks of protoplast culture. (d) Callus formation from protoplast-derived colonies (e,f) Organogenesis and regenerated shoots from protoplast-derived calli (bar=5 mm)

FIG. 8. Targeted deep sequencing of mutant calli. Genotypes of the mutant calli were confirmed by Illumina Miseq. Sequence of each allele and the number of sequencing reads were analyzed. (A1), allele1. (A2), allele2.

FIG. 9. Plant regeneration from RGEN RNP-transfected protoplasts in *L. sativa*. (a-c) Organogenesis and shoot formation from protoplast-derived calli; wild type (#28), bi-allelic/heterozygote (#24), bi-allelic/homozygote (#30). (d) In vitro shoot proliferation and development. (e) Elongation and growth of shoots in MS culture medium free of PGR. (f) Root induction onto elongated shoots. (g) Acclimatization of plantlets. (h,i) Regenerated whole plants.

FIG. 10. Germline transmission of BIN2 mutant alleles. (a) Bolting and flowering in regenerated plants. (b) RGEN-RFLP analysis for genotyping seeds obtained from a homozygous bi-allelic mutant termed T0-12. (c) DNA sequences of the wild-type, T0-12 mutant, and T1 mutants derived from the T0-12 line. Red triangles indicate an inserted nucleotide.

BEST MODE FOR CARRYING OUT THE INVENTION

An aspect of the present invention provides a method for preparing a plant from a protoplast comprising knocking-out or knocking-in one or more the endogenous gene of the protoplast.

In one embodiment, the endogenous gene of the plant may be a gene capable of increasing stress resistance of the plant by knocking-out or knocking-in.

In another embodiment, the endogenous gene of the plant may be a gene involved in Brassinosteroid signal transduction of plants.

In still another embodiment, (i) in the knocking-out step, the endogenous gene may be one or more genes selected from the group consisting of BIN2 gene, BKI1 gene, and homolog genes thereof; and (ii) in the knocking-in step, the gene being knocked in may be one or more genes selected from the group consisting of BRI1 gene, BSU gene, BZR1 gene, DWF4 gene, CYP85A1, and homolog genes thereof.

In still another embodiment, the knocking-out of genes may be performed by knocking-out one or two alleles of the genes selected from the group consisting of BIN 2 gene, BKI1 gene, and homolog genes thereof.

In still another embodiment, the knocking-out of genes may be performed by gene knock-out and the knocking-in of genes is performed by gene knock-in.

In still another embodiment, the knocking-out of genes may be performed using an engineered nuclease specific to one or more genes selected from the group consisting of BIN2 gene, BKI1 gene, and homolog genes thereof.

In still another embodiment, the engineered nuclease may be selected from the group consisting of zinc finger nuclease (ZFN), transcription activator-like effector nuclease (TALEN), and RNA-guided engineered nuclease (RGEN).

In still another embodiment, the RGEN may comprise guide RNA, which specifically binds to a specific sequence of one or more genes selected from the group consisting of BIN2 gene, BKI1 gene, and homolog genes thereof, or DNA encoding the guide RNA; and a nucleic acid encoding a Cas protein, or a Cas protein.

In still another embodiment, the knocking-out of genes may be performed by introducing the guide RNA, which specifically binds to a specific sequence of one or more genes selected from the group consisting of BIN2 gene, BKI1 gene, and homolog genes thereof, or DNA encoding the guide RNA; and a nucleic acid encoding a Cas protein, or a Cas protein, to the protoplast.

In still another embodiment, the guide RNA may be in the form of a dual RNA or a single-chain guide RNA (sgRNA) comprising crRNA and tracrRNA.

In still another embodiment, the single-chain guide RNA may comprise a part of crRNA and tracrRNA.

In still another embodiment, the single-chain guide RNA may be in the form of isolated RNA.

In still another embodiment, the DNA encoding the guide RNA may be encoded by a vector, and the vector is virus vector, plasmid vector, or *Agrobacterium* vector.

In still another embodiment, the Cas protein may be a Cas9 protein or a variant thereof.

In still another embodiment, the Cas protein may recognize NGG trinucleotide.

In still another embodiment, the Cas protein may be linked to a protein transduction domain.

In still another embodiment, the variant of the Cas9 protein may be in a mutant form of Cas9 protein, wherein the catalytic aspartate residue is substituted with another amino acid.

In still another embodiment, the amino acid may be alanine.

In still another embodiment, the nucleic acid encoding a Cas protein or Cas protein may be derived from a microorganism of the genus *Streptococcus*.

In still another embodiment, the microorganism of the genus *Streptococcus* may be *Streptococcus pyogenes*.

In still another embodiment, the protoplast may be derived from *Lactuca sativa*.

In still another embodiment, the introduction may be performed by co-transfecting or serial-transfecting of a nucleic acid encoding a Cas protein or a Cas protein, and the guide DNA or DNA encoding the guide DNA into a protoplast.

In still another embodiment, the serial-transfection may be performed by firstly transfecting a Cas protein or a nucleic acid encoding a Cas protein followed by secondly transfecting a naked guide RNA.

In still another embodiment, the introduction may be performed by a method selected from the group consisting of microinjection, electroporation, DEAE-dextran treatment, lipofection, nanoparticle-mediated transfection, protein transduction domain-mediated transfection, and PEG-mediated transfection.

In still another embodiment, the method may further comprise regenerating the protoplast having a knocked-out gene.

In still another embodiment, the regeneration may comprise culturing a protoplast having one or more knocked-out genes selected from the group consisting of BIN2 gene, BKI1 gene, and homolog genes thereof in agarose-containing medium to form callus; and culturing the callus in regeneration medium.

Another aspect of the present invention is a plant regenerated from a genome-edited protoplast prepared by the above method.

Another aspect of the present invention is a composition for cleaving DNA encoding BIN2 gene in a plant cell, comprising: a guide RNA specific to DNA encoding Brassinosteroid Insensitive 2 (BIN2) gene, BKI1 gene, or homologs thereof, or DNA encoding the guide RNA; and a nucleic acid encoding a Cas protein, or a Cas protein.

In still another embodiment, the composition may induce a targeted mutagenesis in a plant cell.

Another aspect of the present invention is a composition for preparing a plant from a protoplast, comprising: a guide RNA specific to DNA encoding Brassinosteroid Insensitive 2 (BIN2) gene, BKI1 gene, or homologs thereof, or DNA encoding the guide RNA; and a nucleic acid encoding a Cas protein or a Cas protein.

Another aspect of the present invention is a kit for preparing a plant from a protoplast comprising the above composition.

Mode for the Invention

Hereinafter, the present invention will be described in further detail with reference to examples. It is to be understood, however, that these examples are for illustrative purposes only and are not intended to limit the scope of the present invention.

Methods

Cas9 Protein and Guide RNAs.

Cas9 protein tagged with a nuclear localization signal was purchased from ToolGen, Inc. (South Korea). Templates for guide RNA transcription were generated by oligo-extension using Phusion polymerase (Table 1-4). Guide RNAs were in vitro transcribed through run-off reactions using the T7 RNA polymerase (New England Biolabs) according to the manufacturer's protocol. The reaction mixture was treated with DNase I (New England Biolabs) in 1× DNase I reaction buffer. Transcribed sgRNAs were resolved on an 8% denaturing ureapolyacryl amide gel with SYBR gold staining (Invitrogen) for quality control. Transcribed sgRNAs were purified with MG™ PCR Product Purification SV (Macrogen) and quantified by spectrometry.

TABLE 1

List of primers used for T7E1 assay

| Target | 1st PCR | | 2nd PCR | |
|---|---|---|---|---|
| | Forward (5' to 3') | Reverse (5' to 3') | Forward (5' to 3') | Reverse (5' to 3') |
| AOC | CGAGCTCAATG AACGTGACC (SEQ ID NO: 1) | GATCAGAATG CAGAGTCC AGC(SEQ ID NO: 2) | | ATGCAGAGTC CAGCCGT TAT (SEQ ID NO: 3) |
| PHYB | TGGTTGTTTGC CATCACACT (SEQ ID NO: 4) | GAAAAGCCTG AAAGGACGAA (SEQ ID NO: 5) | | GCCTCCCCATT TGATTTCTT (SEQ ID NO: 6) |
| P450 | GGAGCTGAAC CACTTCATCC (SEQ ID NO: 7) | CCCAGCACCTG CTTCACTAT (SEQ ID NO: 8) | ACCCCAGGCC AATTCATG (SEQ ID NO: 9) | GGGACAAAGA TTCATGCAGCA (SEQ ID NO: 10) |
| DWD1 | CCTTTTCTTTG TGGGGTGTG (SEQ ID NO: 11) | TCCTTCTCCCT CTCCTCCTG (SEQ ID NO: 12) | ATCTCGTGCCA TCTCCATCC (SEQ ID NO: 13) | |
| BRI1 | ATTTGGGCTGA TCCTTGTTG (SEQ ID NO: 14) | TGTTGAACACC TGAAACTTTGG (SEQ ID NO: 15) | ACCAATTGGA AGCTGACTGG (SEQ ID NO: 16) | CCATGCCAAA ATCTGAAACC (SEQ ID NO: 17) |

TABLE 2

List of primers used for targeted deep sequencing (1st primers)

| Target | Forward (5' to 3') | Reverse (5' to 3') |
|---|---|---|
| PHYB-OT1 | CCGCATTCAACAGCTCTCTC (SEQ ID NO: 18) | GCTCAAATCAGGTGGCTAC G( SEQ ID NO: 19) |

TABLE 2-continued

List of primers used for targeted deep sequencing (1st primers)

| Target | Forward (5' to 3') | Reverse (5' to 3') |
|---|---|---|
| PHYB-OT2 | AGGCTGTTCAAAGTCCAGGT (SEQ ID NO: 20) | ATCGCTGGGAGTTCAACAGA (SEQ ID NO: 21) |
| PHYB-OT3 | CCAATGGGCCTGAAAGCTTT (SEQ ID NO: 22) | ACAACCAAAATCCGCAACGA (SEQ ID NO: 23) |
| BRI1-TS1-OT1 | CGCAAGTTGGTCAGAGTGAA (SEQ ID NO: 24) | ACAAGGAGGCTGACGGAAA (SEQ ID NO: 25) |
| BRI1-TS1-OT2 | ACTCGTTACAGGACTCGGTG (SEQ ID NO: 26) | TACAGAGCTGCTTCTGGACC (SEQ ID NO: 27) |
| BRI1-TS1-OT3 | TTACCGTAGCTGGGATCGTC (SEQ ID NO: 28) | GACTTGTCTCCCTCGCCATA (SEQ ID NO: 29) |
| BRI1-TS1-OT4 | GCAAGGACGGATGAGAAACC (SEQ ID NO: 30) | TGGCATAGTCGCTATTTCGC (SEQ ID NO: 31) |
| BRI1-TS1-OT5 | GTCTCCAAAATCCTCGTCGC (SEQ ID NO: 32) | GGAAAATTTCTCCCCGCCTC (SEQ ID NO: 33) |
| BRI1-TS1-OT6 | TATGGCGGAAGGTGTAGGTC (SEQ ID NO: 34) | TTGCTTGGCTGAAACTCACC (SEQ ID NO: 35) |
| BRI1-TS2-OT1 | CGAGTGCTGATGTGTGTGTT (SEQ ID NO: 36) | TCTCTTGGTGCAGGGTGAAT (SEQ ID NO: 37) |
| BRI1-TS2-OT2 | CCCTCTCAATTGCAGCCATT (SEQ ID NO: 38) | CGTGTCTTCCTCTGCCATTG (SEQ ID NO: 39) |
| BRI1-TS2-OT3 | ACATTTGCTGCATTGGGATCT (SEQ ID NO: 40) | CCAACCCGGCTCAAACTTAC (SEQ ID NO: 41) |
| BRI1-TS2-OT4 | CTCGTCTCAGCCAGGTTAGT (SEQ ID NO: 42) | ATCAAGAATCCAATGGCGGC (SEQ ID NO: 43) |

TABLE 3

List of primers used for targeted deep sequencing (2nd primers)

| | Sequence (5' to 3') |
|---|---|
| AOC-deepF | ACACTCTTTCCCTACACGACGCTCTTCCGATCTCGAGCTCAATGAACGTGACC (SEQ ID NO: 44) |
| AOC-deepR | GTGACTGGAGTTCAGACGTGTGCTCTTCCGATCTGATCAGAATGCAGAGTCCAGC (SEQ ID NO: 45) |
| PHYB-deepF | ACACTCTTTCCCTACACGACGCTCTTCCGATCTGCAAATGTCAGAGAAACGCG (SEQ ID NO: 46) |
| PHYB-deepR | GTGACTGGAGTTCAGACGTGTGCTCTTCCGATCTATCAGTGCTTAATCCGGTTGA (SEQ ID NO: 47) |
| P450-deepF | ACACTCTTTCCCTACACGACGCTCTTCCGATCTACCCCAGGCCAATTCATG (SEQ ID NO: 48) |
| P450-deepR | GTGACTGGAGTTCAGACGTGTGCTCTTCCGATCTGGCTCTGGTTTCAAGTTAGTACA (SEQ ID NO: 49) |
| DWD1-deepF | ACACTCTTTCCCTACACGACGCTCTTCCGATCTGCCACAACCAACGGATC (SEQ ID NO: 50) |
| DWD1-deepR | GTGACTGGAGTTCAGACGTGTGCTCTTCCGATCTTGGATTCAGACCCACCCG (SEQ ID NO: 51) |
| BRI1-TS1-deepF | ACACTCTTTCCCTACACGACGCTCTTCCGATCTTTGCGGATCTTCTTCAGGCT (SEQ ID NO: 52) |
| BRI1-TS1-deepR | GTGACTGGAGTTCAGACGTGTGCTCTTCCGATCTGCTCGTCTCCAACTTTGCAA (SEQ ID NO: 53) |

TABLE 3-continued

List of primers used for targeted deep sequencing (2nd primers)

| | Sequence (5' to 3') |
|---|---|
| BRI1-TS2-deepF | ACACTCTTTCCCTACACGACGCTCTTCCGATCTTTGCA AAGTTGGAGACGAGC (SEQ ID NO: 54) |
| BRI1-TS2-deepR | GTGACTGGAGTTCAGACGTGTGCTCTTCCGATCTATCT GAAACCCGAGCTTCCA (SEQ ID NO: 55) |
| BIN2-deepF | ACACTCTTTCCCTACACGACGCTCTTCCGATCTTGTGG TTTCTTTGAAGCATTGT (SEQ ID NO: 56) |
| BIN2-deepR | GTGACTGGAGTTCAGACGTGTGCTCTTCCGATCTTGCC ACTCACAATCACATGT (SEQ ID NO: 57) |
| PHYB-OT1-deepF | ACACTCTTTCCCTACACGACGCTCTTCCGATCTTTCAT GAAGGTGGCTCAGGT (SEQ ID NO: 58) |
| PHYB-OT1-deepR | GTGACTGGAGTTCAGACGTGTGCTCTTCCGATCTCTTC ATTCTCTTGCCGTGGG (SEQ ID NO: 59) |
| PHYB-OT2-deepF | ACACTCTTTCCCTACACGACGCTCTTCCGATCTGGTGA CAATGTGGCTAATGGT (SEQ ID NO: 60) |
| PHYB-OT2-deepR | GTGACTGGAGTTCAGACGTGTGCTCTTCCGATCTACTC GGCCAATGTTACTCCA (SEQ ID NO: 61) |
| PHYB-OT3-deepF | ACACTCTTTCCCTACACGACGCTCTTCCGATCTGGCTT GTTGGGTGATCTTGA (SEQ ID NO: 62) |
| PHYB-OT3-deepR | GTGACTGGAGTTCAGACGTGTGCTCTTCCGATCTGACC CACTTCACAGAAAGCA (SEQ ID NO: 63) |
| BRI1-TS1-OT1-deepF | ACACTCTTTCCCTACACGACGCTCTTCCGATCTTCTGC ACGATTCTACCTGACA (SEQ ID NO: 64) |
| BRI1-TS1-OT1-deepR | GTGACTGGAGTTCAGACGTGTGCTCTTCCGATCTTCTC CTGTCATGTGTTCCTAAC (SEQ ID NO: 65) |
| BRI1-TS1-OT2-deepF | ACACTCTTTCCCTACACGACGCTCTTCCGATCTTAGCT ATGCCGGTGGAAGTT (SEQ ID NO: 66) |
| BRI1-TS1-OT2-deepR | GTGACTGGAGTTCAGACGTGTGCTCTTCCGATCTACAG AAGTAGCCATTCCGAGA (SEQ ID NO: 67) |
| BRI1-TS1-OT3-deepF | ACACTCTTTCCCTACACGACGCTCTTCCGATCTCGGAG ACCTTTAAGCTTCGC (SEQ ID NO: 68) |
| BRI1-TS1-OT3-deepR | GTGACTGGAGTTCAGACGTGTGCTCTTCCGATCTTGCA AAACCATCAGCAGTGG (SEQ ID NO: 69) |
| BRI1-TS1-OT4-deepF | ACACTCTTTCCCTACACGACGCTCTTCCGATCTGTTTG AAGAAGGTGGCCCAG (SEQ ID NO: 70) |
| BRI1-TS1-OT4-deepR | GTGACTGGAGTTCAGACGTGTGCTCTTCCGATCTGGTG GGACGATCGAGCTTAT (SEQ ID NO: 71) |
| BRI1-TS1-OT5-deepF | ACACTCTTTCCCTACACGACGCTCTTCCGATCTTGACT AACCGCTTGTCCTCA (SEQ ID NO: 72) |
| BRI1-TS1-OT5-deepR | GTGACTGGAGTTCAGACGTGTGCTCTTCCGATCTACGT TGCCAGTAAAGTTCGC (SEQ ID NO: 73) |
| BRI1-TS1-OT6-deepF | ACACTCTTTCCCTACACGACGCTCTTCCGATCTCGTCT CTTACTCGCCTCCTT (SEQ ID NO: 74) |
| BRI1-TS1-OT6-deepR | GTGACTGGAGTTCAGACGTGTGCTCTTCCGATCTTCAT CTGAGGTTGGTTCGACA (SEQ ID NO:75) |
| BRI1-TS2-OT1-deepF | ACACTCTTTCCCTACACGACGCTCTTCCGATCTTCATT CAGCTTTGCCAAACCA (SEQ ID NO: 76) |
| BRI1-TS2-OT1-deepR | GTGACTGGAGTTCAGACGTGTGCTCTTCCGATCTTCCG GTGGAATTACTGCTCA (SEQ ID NO: 77) |
| BRI1-TS2-OT2-deepF | ACACTCTTTCCCTACACGACGCTCTTCCGATCTTGTTC ACAATTACTGCCACCA (SEQ ID NO: 78) |

TABLE 3-continued

List of primers used for targeted deep sequencing (2nd primers)

| | Sequence (5' to 3') |
|---|---|
| BRI1-TS2-OT2-deepR | GTGACTGGAGTTCAGACGTGTGCTCTTCCGATCTACTC TCTACGATCGCAACTCT (SEQ ID NO: 79) |
| BRI1-TS2-OT3-deepF | ACACTCTTTCCCTACACGACGCTCTTCCGATCTGGAGA TGGAGGGGATGGAAC (SEQ ID NO: 80) |
| BRI1-TS2-OT3-deepR | GTGACTGGAGTTCAGACGTGTGCTCTTCCGATCTCGGC TCTGAACAGGTCTACA (SEQ ID NO: 81) |
| BRI1-TS2-OT4-deepF | ACACTCTTTCCCTACACGACGCTCTTCCGATCTTGCAA TCAGATGTCCGGTCA (SEQ ID NO: 82) |
| BRI1-TS2-OT4-deepR | GTGACTGGAGTTCAGACGTGTGCTCTTCCGATCTGTAC CTCTTCAGCAACCAAGT (SEQ ID NO: 83) |

TABLE 4

In vitro transcription template

| | Sequence (5' to 3') |
|---|---|
| AOC-sgF | GAAATTAATACGACTCACTATAGCAAAAGACTGTCAATTCCC TGTTTTAGAGCTAGAAATAGCAAG (SEQ ID NO: 84) |
| PHYB-sgF | GAAATTAATACGACTCACTATAGGCACTAGGAGCAACACCCA ACGTTTTAGAGCTAGAAATAGCAAG (SEQ ID NO: 85) |
| P450-sgF | GAAATTAATACGACTCACTATAGGCATATAGTTGGGTCATGG CAGTTTTAGAGCTAGAAATAGCAAG (SEQ ID NO: 86) |
| DWD1-TS1-sgF | GAAATTAATACGACTCACTATAGGTGCATCGTCCAAGCGCAC AGGTTTTAGAGCTAGAAATAGCAAG (SEQ ID NO: 87) |
| DWD1-TS2-sgF | GAAATTAATACGACTCACTATAGGCTACGACGTCAGGTTCTA CCGTTTTAGAGCTAGAAATAGCAAG (SEQ ID NO: 88) |
| BRI1-TS1-sgF | GAAATTAATACGACTCACTATAGGTTTGAAAGATGGAAGCGC GGGTTTTAGAGCTAGAAATAGCAAG (SEQ ID NO: 89) |
| BRI1-TS2-sgF | GAAATTAATACGACTCACTATAGGTGAAACTAAACTGGTCCA CAGTTTTAGAGCTAGAAATAGCAAG (SEQ ID NO: 90) |
| BIN2-sgF | GAAATTAATACGACTCACTATAGATCACAGTGATGCTCGTCA AGTTTTAGAGCTAGAAATAGCAAG (SEQ ID NO: 91) |
| Universal sgR | AAAAAAGCACCGACTCGGTGCCACTTTTTCAAGTTGATAACGG ACTAGCCTTATTTTAACTTGCTATTTCTAGCTCTAAAAC (SEQ ID NO: 92) |

Protoplast Culture.

Protoplasts were isolated as previously described from *Arabidopsis*, rice, and lettuce. Initially, *Arabidopsis* (*Arabidopsis thaliana*) ecotype Columbia-0, rice (*Oryza sativa* L.) cv. Dongjin, and lettuce (*Lactuca sativa* L.) cv Cheongchima seeds were sterilized in a 70% ethanol, 0.4% hypochlorite solution for 15 min, washed three times in distilled water, and sown on ½× Murashige and Skoog solid medium supplemented with 2% sucrose. The seedlings were grown under a 16 h light (150 μmol m$^{-2}$ s$^{-1}$) and 8 h dark cycle at 25° C. in a growth room. For protoplast isolation, the leaves of 14 d *Arabidopsis* seedlings, the stem and sheath of 14 d rice seedlings, and the cotyledons of 7 d lettuce seedlings were digested with enzyme solution (1.0% cellulase R10, 0.5% macerozyme R10, 0.45 M mannitol, 20 mM MES [pH 5.7], CPW solution) during incubation with shaking (40 rpm) for 12 h at 25° C. in darkness and then diluted with an equal volume of W5 solution. The mixture was filtered before protoplasts were collected by centrifugation at 100 g in a round-bottomed tube for 5 min. Re-suspended protoplasts were purified by floating on a CPW 21S (21% [w/v] sucrose in CPW solution, pH 5.8) solution followed by centrifugation at 80 g for 7 min. The purified protoplasts were washed with W5 solution and pelleted by centrifugation at 70 g for 5 min. Finally, protoplasts were re-suspended in W5 solution and counted under the microscope using a hemocytometer. Protoplasts were diluted to a density of 1×10$^6$ protoplasts/ml of MMG solution (0.4 M mannitol and 15 mM MgCl$_2$, 4 mM MES [pH 5.7]).

Protoplast Transfection.

PEG-mediated RNP transfections were performed as previously described. Briefly, to introduce DSBs using an RNP complex, 1×10$^5$ protoplast cells were transfected with Cas9 protein (10-60 μg) premixed with in vitro transcribed sgRNA (20-120 μg). Prior to transfection, Cas9 protein in storage buffer (20 mM HEPES pH 7.5, 150 mM KCl, 1 mM DTT, and 10% glycerol) was mixed with sgRNA in 1×NEB buffer 3 and incubated for 10 min at room temperature. A mixture of $1\times10^5$ protoplasts (or $5\times10^5$ protoplasts in the case of lettuce) re-suspended in 200 μL MMG solution was gently mixed with 5-20 μL of RNP complex and 210 μL of freshly prepared PEG solution (40% [w/v] PEG 4000; Sigma No. 95904, 0.2 M mannitol and 0.1 M $CaCl_2$)), and then incubated at 25° C. for 10 min in darkness. After incubation, 950 μL W5 solution (2 mM MES [pH 5.7], 154 mM NaCl, 125 mM $CaCl_2$) and 5 mM KCl) were added slowly. The resulting solution was mixed well by inverting the tube. Protoplasts were pelleted by centrifugation at 100 g for 3 min and re-suspended gently in 1 ml WI solution (0.5 M mannitol, 20 mM KCl and 4 mM MES at pH 5.7). Finally, the protoplasts were transferred into multi-well plates and cultured under dark conditions at 25° C. for 24-48 h. Cells were analyzed one day after transfection.

Protoplast Regeneration.

RNP-transfected protoplasts were re-suspended in ½× B5 culture medium supplemented with 375 mg/l $CaCl_2.2H_2O$, 18.35 mg/l NaFe-EDTA, 270 mg/l sodium succinate, 103 g/l sucrose, 0.2 mg/l 2,4 dichlorophenoxyacetic acid (2,4-D), 0.3 mg/l 6-benzylaminopurine (BAP), and 0.1 g/l MES. The protoplasts were mixed with a 1:1 solution of ½× B5 medium and 2.4% agarose to a culture density of $2.5\times10^5$ protoplasts/ml. The protoplasts embedded in agarose were plated onto 6-well plates, overlaid with 2 ml of liquid ½× B5 culture medium, and cultured at 25° C. in darkness. After 7 days, the liquid medium replaced with fresh culture medium. The cultures were transferred to the light (16 h light [30 μmol $m^{-2}$ $s^{-1}$] and 8 h darkness) and cultured at 25° C. After 3 weeks of culture, micro-calli were grown to a few mm in diameter and transferred to MS regeneration medium supplemented with 30 g/l sucrose, 0.6% plant agar, 0.1 mg/l α-naphthaleneacetic acid (NAA), 0.5 mg/l BAP. Induction of multiple lettuce shoots was observed after about 4 weeks on regeneration medium.

Rooting, Transfer to Soil and Hardening of Lettuce.

To regenerate whole plants, proliferated and elongated adventitious shoots were transferred to a fresh regeneration medium and incubated for 4-6 weeks at 25° C. in the light (16 h light [120 μmol $m^{-2}$ $s^{-1}$] and 8 h darkness). For root induction, approximately 3-5 cm long plantlets were excised and transferred onto a solid hormone-free ½× MS medium in Magenta vessels. Plantlets developed from adventitious shoots were subjected to acclimation, transplanted to potting soil, and maintained in a growth chamber at 25° C. (100-150 μmol $m^{-2}$ $s^{-1}$ under cool-white fluorescent lamps with a 16-h photoperiod).

T7E1 Assay.

Genomic DNA was isolated from protoplasts or calli using DNeasy Plant Mini Kit (Qiagen). The target DNA region was amplified and subjected to the T7E1 assay as described previously. In brief, PCR products were denatured at 95° C. and cooled down to a room temperature slowly using a thermal cycler. Annealed PCR products were incubated with T7 endonuclease I (ToolGen, Inc.) at 37° C. for 20 min and analyzed via agarose gel electrophoresis.

RGEN-RFLP.

The RGEN-RFLP assay was performed as previously described. Briefly, PCR products (300-400 ng) were incubated in 1×NEB buffer 3 for 60 min at 37° C. with Cas9 protein (1 μg) and sgRNA (750 ng) in a reaction volume of 10 μl. RNase A (4 μg) was then added to the reaction mixture and incubated at 37° C. for 30 min to remove the sgRNA. The reaction was stopped by adding 6× stop solution (30% glycerol, 1.2% SDS, 250 mM EDTA). DNA products were electrophoresed using a 2.5% agarose gel.

Targeted Deep Sequencing.

The on-target and potential off-target sites were amplified from genomic DNA. Indices and sequencing adaptors were added by additional PCR. High-throughput sequencing was performed using Illumina Miseq (v2, 300 cycle).

Result

Purified Cas9 protein was mixed with two to 10 fold molar excess of gRNAs targeting four genes in three plant species in vitro to form preassembled RNPs. The RGEN RNPs were then incubated with protoplasts derived from Arabidopsis (A. thaliana), a wild type of tobacco (N. attenuate), and rice (O. sativa) in the presence of polyethylene glycol (PEG). We used both the T7 endonuclease I (T7E1) assay and targeted deep sequencing to measure mutation frequencies in transfected cells (FIG. 1a,b). Indels were detected at the expected position, that is, 3 nucleotide (nt) upstream of a NGG protospacer-adjacent motif (PAM), with frequencies that ranged from 8.4% to 44%.

We also co-transfected two gRNAs whose target sites were separated by 201 base pairs (bps) in another gene in Arabidopsis to investigate whether the repair of two concurrent DSBs would give rise to targeted deletion of the intervening sequence, as shown in human cells. Sanger sequencing showed that 223 bp DNA sequences were deleted in the protoplasts (FIG. 1c). Notably, RGEN-induced mutations were detected 24 hours post-transfection, suggesting that RGENs cut target sites immediately after transfection and induce mutations before a full cycle of cell division.

Next, we investigated whether RGEN RNPs can induce off-target mutations at sites highly homologous to on-target sites. We searched for potential off-target sites of the PHYTOCHROME B (PHYB) and BRASSINOSTEROID INSENSITIVE 1 (BRI1) gene-specific sgRNAs in the Arabidopsis genome using the Cas-OFFinder program and used targeted deep sequencing to measure mutation frequencies (FIG. 5). Indels were not detected at any of these sites that differed from on-target sites by two to five nucleotides, in line with our previous results in human cells.

We designed an RGEN target site (SEQ ID NO: 93) to disrupt the BRASSINOSTEROID INSENSITIVE 2 (BIN2) gene, which encodes a negative regulator in a brassinosteroid (BR) signaling pathway (FIG. 2a). We transfected the RGEN RNP in the presence of polyethylene glycol (PEG) and measured the targeted gene modification efficiencies caused by RGEN using both the T7 endonuclease 1 (T7E1) assay and targeted deep sequencing. Indels were detected at the expected position, that is, 3 nucleotide (nt) upstream of NGG protospacer-adjacent motif (PAM), with frequencies that ranged from 8.3% to 11% (9.0% on average) using T7E1 assay and 3.2% to 5.7% (4.3% on average) using NGS assay (FIG. 2b, c).

We performed the regeneration process to produce whole plants which contain the BIN2 mutant alleles from RGEN-RNP treated protoplasts. Only a fraction (<0.5%) of protoplasts could be cultured to form calli. Among these, 35 of fast-growing lines were used to perform further analyses (FIG. 3). We performed the RGEN-RFLP assay and targeted deep sequencing to genotype the lettuce microcalli. RGEN-RFLP assay distinguishes mono-allelic mutant clones (50% cleavage) from heterozygous bi-allelic mutant clones (no cleavage) and homozygous bi-allelic mutant clones (no cleavage) from wild-type clones (100%) cleavage. Remarkably, these analyses showed that two of 35 (5.7%) calli contained mono-allelic mutations and 14 of 35 (40%) calli contained bi-allelic mutations at the target site. Thus, the mutation frequency in regenerated calli was 42.9% (=30 mutant alleles/70 alleles), showing up to 10-fold increase from that in protoplasts. Note that we have obtained genome-edited lettuce at a frequency of 43% without any selection, an extremely high frequency compared to the mutation frequency in bulk populations, suggesting that RGEN-induced mutations in the BIN2 gene were stably maintained and enriched during regeneration process.

BIN2 gene disruption showed no morphological changes but, some stress-tolerant phenotypes in rice. We propose that up-regulation of BR signaling caused by knocking out the BIN2 gene may facilitate the overall rate of cell proliferation and growth and give advantages to calli standing the stressful regeneration process.

Finally, we transfected an RGEN RNP to disrupt the lettuce (*Lactuca sativa*) homolog of *Arabidopsis* BRASSINOSTEROID INSENSITIVE 2 (BIN2) gene (FIG. 6), which encodes a negative regulator in a brassinosteroid (BR) signaling pathway, in lettuce protoplasts and obtained microcalli regenerated from the RNP-transfected cells (FIG. 2-4 and FIG. 7). We used the same RGEN RNP in a RFLP analysis to genotype the lettuce microcalli. Unlike the T7E1 assay, this analysis distinguishes mono-allelic mutant clones (50% cleavage) from heterozygous bi-allelic mutant clones (no cleavage) and homozygous bi-allelic mutant clones (no cleavage) from wild-type clones (100% cleavage). Furthermore, the RGEN-RFLP assay is not limited by sequence polymorphisms near the nuclease target site that may exist in the lettuce genome. This assay showed that two of 35 (5.7%) calli contained mono-allelic mutations and 14 of 35 (40%) calli contained bi-allelic mutations at the target site (FIG. 3, FIG. 4b), demonstrating that RGEN-induced mutations were stably maintained after regeneration. Thus, the mutation frequency in lettuce calli was 46%. We also used targeted deep sequencing to confirm these genotypes in the 16 mutant calli. The number of base pairs deleted or inserted at the target site ranged from −9 to +1, consistent with the mutagenic patterns observed in human cells. No apparent mosaicism was detected in these clones (FIG. 8), suggesting that the RGEN RNP cleaved the target site immediately after transfection and induced indels before cell division.

We then determined whether the BIN2-specific RGEN induced collateral damage in the lettuce genome using high-throughput sequencing. No off-target mutations were induced at 91 homologous sites that differed by one to 5 nucleotides from the on-target site in three BIN2-mutated plantlets (Tables 5-8), consistent with our findings in human cells: Off-target mutations induced by CRISPR RGENs are rarely found in a single cell-derived clone.

TABLE 5

Number of potential off-target sites in the lettuce genome. Potential RGEN off-target sites were identified in the lettuce genome using Cas-OFFinder (www.regenome.net). We used the Legassy_V2 database (Genebank: AFSA00000000.1) as the reference genome and identified homologous sequences that differed from on-target sequences by up to 5 nt. We chose a total of 92 sites and performed targeted deep sequencing. Some sites were excluded in this analysis because PCR primers couldn't be designed owing to a poor quality of reference genome data or because no amplicons were obtained using PCR.

|  | No. of mismatches to on-target site | | | | | | |
| --- | --- | --- | --- | --- | --- | --- | --- |
|  | 0 | 1 | 2 | 3 | 4 | 5 | Total |
| No. of potential off-target sites | 1 (on-target) | 0 | 1 | 4 | 27 | 349 | 382 |
| No. of sites with appropriate PCR primers | 1 | 0 | 1 | 3 | 24 | 72 | 101 |
| No. of sites amplified successfully | 1 | 0 | 1 | 3 | 22 | 65 | 92 |

TABLE 6

Indel frequencies at the on-target and 91 potential off-target sites in three regenerated plantlets. False-positive indels caused by sequencing errors are observed at frequencies that ranged from 0% to 3.0%.

| Site name | Sequence | WT Indels (%) | T0-20 Indels (%) | T0-25 Indels (%) |
| --- | --- | --- | --- | --- |
| On-target | ATCACAGTGATGCTCGTCA AAGG (SEQ ID NO: 94) | 0.021 | 99.912 | 45.042 |
| OT1 | ATCACAGTGcgGCTCGTCAA gGG (SEQ ID NO: 95) | 0.022 | 0.039 | 0 |
| OT2 | caCACAGTGATGtTCGTCAAg GG (SEQ ID NO: 96) | 0 | 0.014 | 0.013 |
| OT3 | ATacCAGgGATGCTCGTCAAt GG (SEQ ID NO: 97) | 0 | 0 | 0 |
| OT4 | ATCAtAGTGATGCTCaTgAAg GG (SEQ ID NO: 98) | 0.013 | 0.03 | 0 |
| OT5 | ATCACAtTGATGCTctaCAtAG G (SEQ ID NO: 99) | 0.023 | 0.033 | 0.012 |
| OT6 | ATaACAGaGAcGaTCGTCAAA GG (SEQ ID NO: 100) | 0.029 | 0.03 | 0.027 |
| OT7 | ATCACAcTGATGCcCtaCAAA GG (SEQ ID NO: 101) | 0.093 | 0.06 | 0.109 |

TABLE 6-continued

Indel frequencies at the on-target and 91 potential off-target sites in three regenerated plantlets. False-positive indels caused by sequencing errors are observed at frequencies that ranged from 0% to 3.0%.

| Site name | Sequence | WT Indels (%) | T0-20 Indels (%) | T0-25 Indels (%) |
| --- | --- | --- | --- | --- |
| OT8 | ATCACAtTGAgGCcCGaCAAAGG (SEQ ID NO: 102) | — | — | — |
| OT9 | ATCACAcTGATGCaCtaCAAAGG (SEQ ID NO: 103) | 0.057 | 0.037 | 0.077 |
| OT10 | caCACAGTGATGtTCaTCAAAGG (SEQ ID NO: 104) | 0.635 | 0.715 | 0.145 |
| OT11 | ATgACAaTtATGCTCtTCAAAGG (SEQ ID NO: 105) | 0.250 | 0 | 0 |
| OT12 | ATCAaAGTGcTcCTCGTgAAAGG (SEQ ID NO: 106) | 0 | 0 | 0 |
| OT13 | taCACAaTGtTGCTCGTCAAcGG (SEQ ID NO: 107) | 0.013 | 0 | 0.012 |
| OT14 | gcCACAGTGATGaTCGTCgAcGG (SEQ ID NO: 108) | 0 | 0 | 0.013 |
| OT15 | ATatCAGgGATGCTCGcCAAtGG (SEQ ID NO: 109) | 0 | 0 | 0 |
| OT16 | AaatCAGTGATcCTCGTCAAcGG (SEQ ID NO: 110) | 0 | 0 | 0.012 |
| OT17 | ATggCAGTGATGgTCGTgAAgGG (SEQ ID NO: 111) | 0 | 0.045 | 0.1 |
| OT18 | cTCAgAGTGtTGCTCtTCAAtGG (SEQ ID NO: 112) | 0 | 0.01 | 0 |
| OT19 | ATCACAGaGATGCTCcaaAAtGG (SEQ ID NO: 113) | 0.074 | 0.033 | 0.068 |
| OT20 | ATCAagGTtATtCTCGTCAAgGG (SEQ ID NO: 114) | 0 | 0.009 | 0 |
| OT21 | AgCACAGTGAgGCTtGTCgAgGG (SEQ ID NO: 115) | 0 | 0 | 0 |
| OT22 | ATatCAagGATGCTCGTCAAtGG (SEQ ID NO: 116) | 0 | 0 | 0 |
| OT23 | tTCcCAGaGATGCTCtTCAAgGG (SEQ ID NO: 117) | 0.024 | 0.05 | 0.035 |
| OT24 | gTCACAtTGATGCTCaTCAtgGG (SEQ ID NO: 118) | 0 | 0 | 0 |
| OT25 | ATCACAGaGATGtTCaTCAtcGG (SEQ ID NO: 119) | 0.022 | 0 | 0 |
| OT26 | ATCAaAaTGAgGCTCGaCAAcGG (SEQ ID NO: 120) | — | — | — |
| OT27 | ATaACAaTGAaGCTCGTtAAtGG (SEQ ID NO: 121) | 0 | 0 | 0 |
| OT28 | ATatCAGgGATGCTCaTCAAtGG (SEQ ID NO: 122) | 0 | 0.011 | 0.017 |
| OT29 | ATCAtAtTGAaGCaCtTCAAAGG (SEQ ID NO: 123) | 0.029 | 0.019 | 0.036 |
| OT30 | cTCACAtTGATGCaCtaCAAAGG (SEQ ID NO: 124) | 0.069 | 0.055 | 0.097 |
| OT31 | tcCACAaTGATGCaCtTCAAAGG (SEQ ID NO: 125) | 0.023 | 0 | 0.012 |

TABLE 6-continued

Indel frequencies at the on-target and 91 potential off-target sites in three regenerated plantlets. False-positive indels caused by sequencing errors are observed at frequencies that ranged from 0% to 3.0%.

| Site name | Sequence | WT Indels (%) | T0-20 Indels (%) | T0-25 Indels (%) |
|---|---|---|---|---|
| OT32 | cTCACAaTgTtTGCTCtaCAAAGG (SEQ ID NO: 126) | — | — | — |
| OT33 | ATgACAaTGAaGCTCGTaAtAGG (SEQ ID NO: 127) | 0 | 0 | 0 |

TABLE 7

| Site name | Sequence | WT Indels (%) | T0-20 Indels (%) | T0-24 Indels(%) | T0-25 Indels(%) |
|---|---|---|---|---|---|
| On-target | ATCACAGTGATGCTCGTCAAAGG (SEQ ID NO: 94) | 0.021 | 99.912 | 99.867 | 45.042 |
| OT34 | cTCtCAGTGgTGCTgGTCgAAGG (SEQ ID NO: 128) | 0 | 0 | 0 | 0.029 |
| OT35 | ATCACAcTtATaCTCGaCAgAGG (SEQ ID NO: 129) | 0 | 0 | 0.054 | 0.018 |
| OT36 | cTCACAGTGAggCTttTaAAAGG (SEQ ID NO: 130) | 0.16 | 0.154 | 0.153 | 0.082 |
| OT37 | ATCACtGTGATGtTCGggAgAGG (SEQ ID NO: 131) | 0 | 0 | 0 | 0.042 |
| OT38 | cTCtCgGTGgTGCTgGTCAAAGG (SEQ ID NO: 132) | 0.045 | 0.061 | 0.069 | 0.082 |
| OT39 | gTgACAGTcATGCaCGTCcAAGG (SEQ ID NO: 133) | 0.017 | 0.023 | 0.013 | 0.017 |
| OT40 | ATCACAcTGATtCcCtaCAAAGG (SEQ ID NO: 134) | 0.051 | 0.097 | 0.024 | 0.077 |
| OT41 | ATgAgAGTGATttTCGTtAAAGG (SEQ ID NO: 135) | 0.03 | 0.017 | 0 | 0.05 |
| OT42 | ATCACtGTGATGtTtacCAAAGG (SEQ ID NO: 136) | 0.038 | 0.035 | 0.042 | 0.012 |
| OT43 | ATCACAGTGATGCTtccacAAGG (SEQ ID NO: 137) | 0 | 0.02 | 0.034 | 0.012 |
| OT44 | gTaACAGTGgTGtTCGaCAAAGG (SEQ ID NO: 138) | 0.113 | 0.209 | 0.142 | 0.192 |
| OT45 | ATCcCAaTcAgGCTCtTCAAAGG (SEQ ID NO: 139) | 0.022 | 0.014 | 0.028 | 0.023 |
| OT46 | cTCACAcTGATGCaCtTCAtAGG (SEQ ID NO: 140) | 0 | 0 | 0 | 0.01 |
| OT47 | AaCACAcTGAgGCTCtgCAAAGG (SEQ ID NO: 141) | — | — | — | — |
| OT48 | ATggCAcTGATGCaCGaCAAAGG (SEQ ID NO: 142) | 0.022 | 0.014 | 0.04 | 0.011 |
| OT49 | caCACtGTcATGtTCGTCAAAGG (SEQ ID NO: 143) | 0.34 | 0.114 | 0.27 | 0.054 |
| OT50 | tTgACAGTGtTcCTaGTCAAAGG (SEQ ID NO: 144) | 0.017 | 0.014 | 0.013 | 0 |
| OT51 | ATCAtAGgtATGtTgGTCAAAGG (SEQ ID NO: 145) | 0 | 0.016 | 0.038 | 0.026 |
| OT52 | ATCACAcTGATGCcCtaCAtAGG (SEQ ID NO: 146) | 0.011 | 0 | 0 | 0.021 |

TABLE 7-continued

| Site name | Sequence | WT Indels (%) | T0-20 Indels (%) | T0-24 Indels(%) | T0-25 Indels(%) |
|---|---|---|---|---|---|
| OT53 | ATCACAcTGATtCcCtgCA AAGG (SEQ ID NO: 147) | 0.047 | 0.036 | 0.043 | 0.025 |
| OT54 | AaCAtAGcGtTGCTaGTCA AAGG (SEQ ID NO: 148) | 0.049 | 0.043 | 0.087 | 0.119 |
| OT55 | ATCACAtgGATcCTCcTgA AAGG (SEQ ID NO: 149) | 0.025 | 0 | 0 | 0 |
| OT56 | tTttCAaTGATGCTCaTCAA AGG (SEQ ID NO: 150) | 0.023 | 0.015 | 0.018 | 0 |
| OT57 | tTCtCtGTcATGtTCGTCAA AGG (SEQ ID NO: 151) | 0.027 | 0.052 | 0.02 | 0.019 |
| OT58 | ATCACAGTatTGgTCcaCA AAGG (SEQ ID NO: 152) | 0.052 | 0.02 | 0.044 | 0.041 |
| OT59 | ATgctAGaGATGCTtGTCA AAGG (SEQ ID NO: 153) | 0.029 | 0.01 | 0.017 | 0.078 |
| OT60 | ATCACAcTGATGCaCtaCA gAGG (SEQ ID NO: 154) | 0 | 0 | 0 | 0.023 |
| OT61 | cTCACAcTGATGCaCtaCA AAGG (SEQ ID NO: 155) | 0.051 | 0.052 | 0.061 | 0.018 |
| OT62 | tTgAtAGTGtTcCTCGTCAA AGG (SEQ ID NO: 156) | — | — | — | — |
| OT63 | ATCACAGatATcaTgGTCA AAGG (SEQ ID NO: 157) | 0.013 | 0 | 0.032 | 0.026 |
| OT64 | ATCttAGTcAaGCTaGTCA AAGG (SEQ ID NO: 158) | — | — | — | — |
| OT65 | ATCAgAtTtATGCTCaTtAA AGG (SEQ ID NO: 159) | — | — | — | — |
| OT66 | ATCtgAGTGATctTCGTCg AAGG (SEQ ID NO: 160) | 0.033 | 0.02 | 0 | 0.027 |

TABLE 8

| Site name | Sequence | WT Indels (%) | T0-20 Indels (%) | T0-24 Indels (%) | T0-25 Indels (%) |
|---|---|---|---|---|---|
| On-target | ATCACAGTGATGCTCGT CAAAGG (SEQ ID NO: 94) | 0.021 | 99.912 | 99.867 | 45.042 |
| OT67 | ATggCAGTGtTcCTaGTCA AAGG (SEQ ID NO: 161) | — | — | — | — |
| OT68 | ATCACAtTtATGCTtaTCtA AGG (SEQ ID NO: 162) | 0.019 | 0.011 | 0.019 | 0.023 |
| OT69 | tcCACAGTGtTcCTaGTCA AAGG (SEQ ID NO: 163) | 0.014 | 0.024 | 0.028 | 0.013 |
| OT70 | tTCttAGgGATGgTCGTCA AAGG (SEQ ID NO: 164) | 0.042 | 0.02 | 0.024 | 0.013 |
| OT71 | AaCACAGTcATGCTCacC AgAGG (SEQ ID NO: 165) | 3.006 | 2.67 | 2.831 | 0.935 |
| OT72 | AaaAgAGTGATGCTtaTCA AAGG (SEQ ID NO: 166) | 0.018 | 0.012 | 0.018 | 0.029 |
| OT73 | cTtcCAGTGATGaTaGTCA AAGG (SEQ ID NO: 167) | 0.051 | 0.021 | 0.02 | 0.043 |
| OT74 | ATCAaAGTGAgataCGTCA AAGG (SEQ ID NO: 168) | 0.012 | 0.022 | 0 | 0.021 |

TABLE 8-continued

| Site name | Sequence | WT Indels (%) | T0-20 Indels (%) | T0-24 Indels (%) | T0-25 Indels (%) |
|---|---|---|---|---|---|
| OT75 | ATgAtAtTGAcGCTtGTCAAAGG (SEQ ID NO: 169) | 0 | 0.055 | 0.02 | 0.053 |
| OT76 | ATCACgcTGATGggCcTCAAAGG (SEQ ID NO: 170) | 0.012 | 0.016 | 0 | 0 |
| OT77 | ATagatGTGATGCTtGTCAAAGG (SEQ ID NO: 171) | 0.012 | 0.02 | 0 | 0.022 |
| OT78 | gTCcCAtTGATGCaCGaCAAAGG (SEQ ID NO: 172) | 0.017 | 0.046 | 0.051 | 0 |
| OT79 | tTgACAaTtATGCTCtTCAAAGG (SEQ ID NO: 173) | 0.175 | 0.178 | 0.18 | 0.332 |
| OT80 | ATtAaAaTcATGtTCGTCAAAGG (SEQ ID NO: 174) | 0.082 | 0.037 | 0.051 | 0.025 |
| OT81 | caCACAGTcATGtTCcTCAAAGG (SEQ ID NO: 175) | 0 | 0.022 | 0.036 | 0.03 |
| OT82 | tTgACAaTcATGCTCtTCAAAGG (SEQ ID NO: 176) | — | — | — | — |
| OT83 | tTCAtAGTGATGtTttTCAAAGG (SEQ ID NO: 177) | 0.043 | 0.059 | 0.033 | 0.058 |
| OT84 | ATCACgcTcATGaTCcTCAAAGG (SEQ ID NO: 178) | 0 | 0.03 | 0 | 0 |
| OT85 | ATCACAcTcATGgaCcTCAAAGG (SEQ ID NO: 179) | 0 | 0.034 | 0.039 | 0.01 |
| OT86 | ATCAtAtTGAaGCcCtTCAAAGG (SEQ ID NO: 180) | 0.027 | 0.053 | 0.079 | 0.053 |
| OT87 | ATCACAaTGATGgTCGgggAAGG (SEQ ID NO: 181) | 0.268 | 0.358 | 0.301 | 0.273 |
| OT88 | ATCAtAaTGAaGCcCtTCAAAGG (SEQ ID NO: 182) | 0.029 | 0.057 | 0.085 | 0.057 |
| OT89 | ATgAatGTtATGCTCtTCAAAGG (SEQ ID NO: 183) | 0 | 0.038 | 0 | 0.052 |
| OT90 | ATCACAcTGATaCcCtaCAAAGG (SEQ ID NO: 184) | 0.027 | 0.026 | 0.053 | 0.051 |
| OT91 | AatAtAaTGATtCTCGTCAAAGG (SEQ ID NO: 185) | 0.022 | 0.02 | 0.013 | 0.036 |
| OT92 | ATgACtGTGtTcCTtGTCAAAGG (SEQ ID NO: 186) | 0 | 0 | 0.122 | 0.074 |
| OT93 | cTCAaAGTcATGaTCtTCAAAGG (SEQ ID NO: 187) | 0 | 0.026 | 0 | 0.022 |
| OT94 | cTCAatGaGATGCTCGaCAAAGG (SEQ ID NO: 188) | 0.053 | 0.052 | 0.056 | 0.057 |
| OT95 | ATCACAcTtAaGCTCtTgAAAGG (SEQ ID NO: 189) | 0.201 | 0.216 | 0.15 | 0.161 |
| OT96 | gTgACAGTGtTGCTtGTCgAAGG (SEQ ID NO: 190) | 0.012 | 0.012 | 0.015 | 0 |
| OT97 | ATaACAacaATGaTCGTCAAAGG (SEQ ID NO: 191) | 0.036 | 0.016 | 0.048 | 0.057 |
| OT98 | AaCACtGTGATGtTtGTCAgAGG (SEQ ID NO: 192) | 0 | 0 | 0 | 0 |

TABLE 8-continued

| Site name | Sequence | WT Indels (%) | T0-20 Indels (%) | T0-24 Indels (%) | T0-25 Indels (%) |
|---|---|---|---|---|---|
| OT99 | ATCACgcTGATagTCcTCA AAGG (SEQ ID NO: 193) | 0 | 0 | 0 | 0 |
| OT100 | gTgACAaTtATGCTCtTCA AAGG (SEQ ID NO: 194) | 1.201 | 0.847 | 1.346 | 0.61 |

Subsequently, whole plants were successfully regenerated from these genome-edited calli and grown in soil (FIG. 4c and FIG. 9). Seeds were obtained from a fully-grown homozygous bi-allelic mutant. As expected, the mutant allele was transmitted to the seeds (FIG. 10). Further studies are warranted to test whether the BIN2-disrupted lettuce displays enhanced BR signaling.

In summary, RGEN RNPs were successfully delivered into plant protoplasts and induced targeted genome modifications in 6 genes in 4 different plant species. Importantly, RGEN-induced mutations were stably maintained in whole plants regenerated from the protoplasts and transmitted to germlines. Because no recombinant DNA is used in this process, the resulting genome-edited plants could be exempted from current GMO regulations, paving the way for the widespread use of RNA-guided genome editing in plant biotechnology and agriculture.

The invention claimed is:

1. A method for preparing a plant from a protoplast comprising knocking-out an endogenous gene of the protoplast by introducing a pre-assembled Cas protein-guide RNA ribonucleoprotein(RNP), wherein the guide RNA specifically binds to a PHYB (phytochrome B) gene or a BIN2 (bridging integrator 2) gene, and wherein the guide RNA specifically binding to PHYB (phytochrome B) is encoded by a nucleic acid comprising the sequence of SEQ ID No: 85; or the guide RNA specifically binding to BIN2 (bridging integrator 2) is encoded by a nucleic acid comprising the sequence of SEQ ID No:91.

2. The method of claim 1, wherein the Cas protein is a Cas9 protein or a variant thereof.

3. The method of claim 1, wherein the Cas protein recognizes NGG trinucleotide.

4. The method of claim 1, wherein the Cas protein is linked to a protein transduction domain.

5. The method of claim 1, wherein the Cas protein is derived from a microorganism of the genus *Streptococcus*.

6. The method of claim 1, wherein the protoplast is derived from *Lactuca sativa*.

7. The method of claim 1, wherein the introduction is performed by a method selected from the group consisting of microinjection, electroporation, DEAE- dextran treatment, lipofection, nanoparticle-mediated transfection, protein transduction domain-mediated transfection, and PEG-mediated transfection.

8. The method of claim 1, further comprising regenerating the protoplast having knocked-out or knocked-in gene.

9. The method of claim 8, wherein the regeneration comprises culturing a protoplast having a knocked-out or knocked-in gene in agarose-containing medium to form callus; and culturing the callus in regeneration medium.

* * * * *

SEQUENCE LISTING

<160> NUMBER OF SEQ ID NOS: 351

<210> SEQ ID NO 1
<211> LENGTH: 20
<212> TYPE: DNA
<213> ORGANISM: Artificial Sequence
<220> FEATURE:
<223> OTHER INFORMATION: AOC 1st PCR-F

<400> SEQUENCE: 1
cgagctcaat gaacgtgacc                                          20

<210> SEQ ID NO 2
<211> LENGTH: 21
<212> TYPE: DNA
<213> ORGANISM: Artificial Sequence
<220> FEATURE:
<223> OTHER INFORMATION: AOC 1st PCR-R

<400> SEQUENCE: 2
gatcagaatg cagagtccag c                                        21

<210> SEQ ID NO 3
<211> LENGTH: 20
<212> TYPE: DNA
<213> ORGANISM: Artificial Sequence
<220> FEATURE:
<223> OTHER INFORMATION: AOC 2st PCR-R

<400> SEQUENCE: 3
atgcagagtc cagccgttat                                          20

<210> SEQ ID NO 4
<211> LENGTH: 20
<212> TYPE: DNA
<213> ORGANISM: Artificial Sequence
<220> FEATURE:
<223> OTHER INFORMATION: PHYB 1st PCR-F

<400> SEQUENCE: 4
tggttgtttg ccatcacact                                          20

<210> SEQ ID NO 5
<211> LENGTH: 20

```
<212> TYPE: DNA
<213> ORGANISM: Artificial Sequence
<220> FEATURE:
<223> OTHER INFORMATION: PHYB 1st PCR-R

<400> SEQUENCE: 5
gaaaagcctg aaaggacgaa                                                 20

<210> SEQ ID NO 6
<211> LENGTH: 20
<212> TYPE: DNA
<213> ORGANISM: Artificial Sequence
<220> FEATURE:
<223> OTHER INFORMATION: PHYB 2nd PCR-R

<400> SEQUENCE: 6
gcctccccat ttgatttctt                                                 20

<210> SEQ ID NO 7
<211> LENGTH: 20
<212> TYPE: DNA
<213> ORGANISM: Artificial Sequence
<220> FEATURE:
<223> OTHER INFORMATION: P450 1st PCR-F

<400> SEQUENCE: 7
ggagctgaac cacttcatcc                                                 20

<210> SEQ ID NO 8
<211> LENGTH: 20
<212> TYPE: DNA
<213> ORGANISM: Artificial Sequence
<220> FEATURE:
<223> OTHER INFORMATION: P450 1st PCR-R

<400> SEQUENCE: 8
cccagcacct gcttcactat                                                 20

<210> SEQ ID NO 9
<211> LENGTH: 18
<212> TYPE: DNA
<213> ORGANISM: Artificial Sequence
<220> FEATURE:
<223> OTHER INFORMATION: P450 2nd PCR-F

<400> SEQUENCE: 9
accccaggcc aattcatg                                                   18

<210> SEQ ID NO 10
<211> LENGTH: 21
<212> TYPE: DNA
<213> ORGANISM: Artificial Sequence
<220> FEATURE:
<223> OTHER INFORMATION: P450 2nd PCR-R

<400> SEQUENCE: 10
gggacaaaga ttcatgcagc a                                               21

<210> SEQ ID NO 11
<211> LENGTH: 20
<212> TYPE: DNA
<213> ORGANISM: Artificial Sequence
<220> FEATURE:
<223> OTHER INFORMATION: DWD1 1st PCR-F

<400> SEQUENCE: 11
```
ccttttcttt gtggggtgtg 20

<210> SEQ ID NO 12
<211> LENGTH: 20
<212> TYPE: DNA
<213> ORGANISM: Artificial Sequence
<220> FEATURE:
<223> OTHER INFORMATION: DWD1 1st PCR-R

<400> SEQUENCE: 12
tccttctccc tctcctcctg 20

<210> SEQ ID NO 13
<211> LENGTH: 20
<212> TYPE: DNA
<213> ORGANISM: Artificial Sequence
<220> FEATURE:
<223> OTHER INFORMATION: DWD1 2nd PCR-F

<400> SEQUENCE: 13
atctcgtgcc atctccatcc 20

<210> SEQ ID NO 14
<211> LENGTH: 20
<212> TYPE: DNA
<213> ORGANISM: Artificial Sequence
<220> FEATURE:
<223> OTHER INFORMATION: BRI1 1st PCR-F

<400> SEQUENCE: 14
atttgggctg atccttgttg 20

<210> SEQ ID NO 15
<211> LENGTH: 22
<212> TYPE: DNA
<213> ORGANISM: Artificial Sequence
<220> FEATURE:
<223> OTHER INFORMATION: BRI1 1st PCR-R

<400> SEQUENCE: 15
tgttgaacac ctgaaacttt gg 22

<210> SEQ ID NO 16
<211> LENGTH: 20
<212> TYPE: DNA
<213> ORGANISM: Artificial Sequence
<220> FEATURE:
<223> OTHER INFORMATION: BRI1 2nd PCR-F

<400> SEQUENCE: 16
accaattgga agctgactgg 20

<210> SEQ ID NO 17
<211> LENGTH: 20
<212> TYPE: DNA
<213> ORGANISM: Artificial Sequence
<220> FEATURE:
<223> OTHER INFORMATION: BRI1 2nd PCR-R

<400> SEQUENCE: 17
ccatgccaaa atctgaaacc 20

<210> SEQ ID NO 18
<211> LENGTH: 20
<212> TYPE: DNA
<213> ORGANISM: Artificial Sequence

<220> FEATURE:
<223> OTHER INFORMATION: PHYB-OT1-F

<400> SEQUENCE: 18
ccgcattcaa cagctctctc					20

<210> SEQ ID NO 19
<211> LENGTH: 20
<212> TYPE: DNA
<213> ORGANISM: Artificial Sequence
<220> FEATURE:
<223> OTHER INFORMATION: PHYB-OT1-R

<400> SEQUENCE: 19
gctcaaatca ggtggctacg					20

<210> SEQ ID NO 20
<211> LENGTH: 20
<212> TYPE: DNA
<213> ORGANISM: Artificial Sequence
<220> FEATURE:
<223> OTHER INFORMATION: PHYB-OT2-F

<400> SEQUENCE: 20
aggctgttca aagtccaggt					20

<210> SEQ ID NO 21
<211> LENGTH: 20
<212> TYPE: DNA
<213> ORGANISM: Artificial Sequence
<220> FEATURE:
<223> OTHER INFORMATION: PHYB-OT2-R

<400> SEQUENCE: 21
atcgctggga gttcaacaga					20

<210> SEQ ID NO 22
<211> LENGTH: 20
<212> TYPE: DNA
<213> ORGANISM: Artificial Sequence
<220> FEATURE:
<223> OTHER INFORMATION: PHYB-OT3-F

<400> SEQUENCE: 22
ccaatgggcc tgaaagcttt					20

<210> SEQ ID NO 23
<211> LENGTH: 20
<212> TYPE: DNA
<213> ORGANISM: Artificial Sequence
<220> FEATURE:
<223> OTHER INFORMATION: PHYB-OT3-R

<400> SEQUENCE: 23
acaaccaaaa tccgcaacga					20

<210> SEQ ID NO 24
<211> LENGTH: 20
<212> TYPE: DNA
<213> ORGANISM: Artificial Sequence
<220> FEATURE:
<223> OTHER INFORMATION: BRI1-TS1-OT1-F

<400> SEQUENCE: 24
cgcaagttgg tcagagtgaa					20

<210> SEQ ID NO 25
<211> LENGTH: 19
<212> TYPE: DNA
<213> ORGANISM: Artificial Sequence
<220> FEATURE:
<223> OTHER INFORMATION: BRI1-TS1-OT1-R

<400> SEQUENCE: 25
acaaggaggc tgacggaaa                                              19

<210> SEQ ID NO 26
<211> LENGTH: 20
<212> TYPE: DNA
<213> ORGANISM: Artificial Sequence
<220> FEATURE:
<223> OTHER INFORMATION: BRI1-TS1-OT2-F

<400> SEQUENCE: 26
actcgttaca ggactcggtg                                             20

<210> SEQ ID NO 27
<211> LENGTH: 20
<212> TYPE: DNA
<213> ORGANISM: Artificial Sequence
<220> FEATURE:
<223> OTHER INFORMATION: BRI1-TS1-OT2-R

<400> SEQUENCE: 27
tacagagctg cttctggacc                                             20

<210> SEQ ID NO 28
<211> LENGTH: 20
<212> TYPE: DNA
<213> ORGANISM: Artificial Sequence
<220> FEATURE:
<223> OTHER INFORMATION: BRI1-TS1-OT3-F

<400> SEQUENCE: 28
ttaccgtagc tgggatcgtc                                             20

<210> SEQ ID NO 29
<211> LENGTH: 20
<212> TYPE: DNA
<213> ORGANISM: Artificial Sequence
<220> FEATURE:
<223> OTHER INFORMATION: BRI1-TS1-OT3-R

<400> SEQUENCE: 29
gacttgtctc cctcgccata                                             20

<210> SEQ ID NO 30
<211> LENGTH: 20
<212> TYPE: DNA
<213> ORGANISM: Artificial Sequence
<220> FEATURE:
<223> OTHER INFORMATION: BRI1-TS1-OT4-F

<400> SEQUENCE: 30
gcaaggacgg atgagaaacc                                             20

<210> SEQ ID NO 31
<211> LENGTH: 20
<212> TYPE: DNA
<213> ORGANISM: Artificial Sequence
<220> FEATURE:
<223> OTHER INFORMATION: BRI1-TS1-OT4-R

<400> SEQUENCE: 31
tggcatagtc gctatttcgc                                               20

<210> SEQ ID NO 32
<211> LENGTH: 20
<212> TYPE: DNA
<213> ORGANISM: Artificial Sequence
<220> FEATURE:
<223> OTHER INFORMATION: BRI1-TS1-OT5-F

<400> SEQUENCE: 32
gtctccaaaa tcctcgtcgc                                               20

<210> SEQ ID NO 33
<211> LENGTH: 20
<212> TYPE: DNA
<213> ORGANISM: Artificial Sequence
<220> FEATURE:
<223> OTHER INFORMATION: BRI1-TS1-OT5-R

<400> SEQUENCE: 33
ggaaaatttc tccccgcctc                                               20

<210> SEQ ID NO 34
<211> LENGTH: 20
<212> TYPE: DNA
<213> ORGANISM: Artificial Sequence
<220> FEATURE:
<223> OTHER INFORMATION: BRI1-TS1-OT6-F

<400> SEQUENCE: 34
tatggcggaa ggtgtaggtc                                               20

<210> SEQ ID NO 35
<211> LENGTH: 20
<212> TYPE: DNA
<213> ORGANISM: Artificial Sequence
<220> FEATURE:
<223> OTHER INFORMATION: BRI1-TS1-OT6-R

<400> SEQUENCE: 35
ttgcttggct gaaactcacc                                               20

<210> SEQ ID NO 36
<211> LENGTH: 20
<212> TYPE: DNA
<213> ORGANISM: Artificial Sequence
<220> FEATURE:
<223> OTHER INFORMATION: BRI1-TS2-OT1-F

<400> SEQUENCE: 36
cgagtgctga tgtgtgtgtt                                               20

<210> SEQ ID NO 37
<211> LENGTH: 20
<212> TYPE: DNA
<213> ORGANISM: Artificial Sequence
<220> FEATURE:
<223> OTHER INFORMATION: BRI1-TS2-OT1-R

<400> SEQUENCE: 37
tctcttggtg cagggtgaat                                               20

<210> SEQ ID NO 38

```
<211> LENGTH: 20
<212> TYPE: DNA
<213> ORGANISM: Artificial Sequence
<220> FEATURE:
<223> OTHER INFORMATION: BRI1-TS2-OT2-F

<400> SEQUENCE: 38
ccctctcaat tgcagccatt                                              20

<210> SEQ ID NO 39
<211> LENGTH: 20
<212> TYPE: DNA
<213> ORGANISM: Artificial Sequence
<220> FEATURE:
<223> OTHER INFORMATION: BRI1-TS2-OT2-R

<400> SEQUENCE: 39
cgtgtcttcc tctgccattg                                              20

<210> SEQ ID NO 40
<211> LENGTH: 21
<212> TYPE: DNA
<213> ORGANISM: Artificial Sequence
<220> FEATURE:
<223> OTHER INFORMATION: BRI1-TS2-OT3-F

<400> SEQUENCE: 40
acatttgctg cattgggatc t                                            21

<210> SEQ ID NO 41
<211> LENGTH: 20
<212> TYPE: DNA
<213> ORGANISM: Artificial Sequence
<220> FEATURE:
<223> OTHER INFORMATION: BRI1-TS2-OT3-R

<400> SEQUENCE: 41
ccaacccggc tcaaacttac                                              20

<210> SEQ ID NO 42
<211> LENGTH: 20
<212> TYPE: DNA
<213> ORGANISM: Artificial Sequence
<220> FEATURE:
<223> OTHER INFORMATION: BRI1-TS2-OT4-F

<400> SEQUENCE: 42
ctcgtctcag ccaggttagt                                              20

<210> SEQ ID NO 43
<211> LENGTH: 20
<212> TYPE: DNA
<213> ORGANISM: Artificial Sequence
<220> FEATURE:
<223> OTHER INFORMATION: BRI1-TS2-OT4-R

<400> SEQUENCE: 43
atcaagaatc caatggcggc                                              20

<210> SEQ ID NO 44
<211> LENGTH: 53
<212> TYPE: DNA
<213> ORGANISM: Artificial Sequence
<220> FEATURE:
<223> OTHER INFORMATION: AOC-deepF

<400> SEQUENCE: 44
```
acactctttc cctacacgac gctcttccga tctcgagctc aatgaacgtg acc        53

<210> SEQ ID NO 45
<211> LENGTH: 55
<212> TYPE: DNA
<213> ORGANISM: Artificial Sequence
<220> FEATURE:
<223> OTHER INFORMATION: AOC-deepR

<400> SEQUENCE: 45
gtgactggag ttcagacgtg tgctcttccg atctgatcag aatgcagagt ccagc      55

<210> SEQ ID NO 46
<211> LENGTH: 53
<212> TYPE: DNA
<213> ORGANISM: Artificial Sequence
<220> FEATURE:
<223> OTHER INFORMATION: PHYB-deepF

<400> SEQUENCE: 46
acactctttc cctacacgac gctcttccga tctgcaaatg tcagagaaac gcg        53

<210> SEQ ID NO 47
<211> LENGTH: 55
<212> TYPE: DNA
<213> ORGANISM: Artificial Sequence
<220> FEATURE:
<223> OTHER INFORMATION: PHYB-deepR

<400> SEQUENCE: 47
gtgactggag ttcagacgtg tgctcttccg atctatcagt gcttaatccg gttga      55

<210> SEQ ID NO 48
<211> LENGTH: 51
<212> TYPE: DNA
<213> ORGANISM: Artificial Sequence
<220> FEATURE:
<223> OTHER INFORMATION: P450-deepF

<400> SEQUENCE: 48
acactctttc cctacacgac gctcttccga tctaccccag gccaattcat g          51

<210> SEQ ID NO 49
<211> LENGTH: 57
<212> TYPE: DNA
<213> ORGANISM: Artificial Sequence
<220> FEATURE:
<223> OTHER INFORMATION: P450-deepR

<400> SEQUENCE: 49
gtgactggag ttcagacgtg tgctcttccg atctggctct ggtttcaagt tagtaca    57

<210> SEQ ID NO 50
<211> LENGTH: 52
<212> TYPE: DNA
<213> ORGANISM: Artificial Sequence
<220> FEATURE:
<223> OTHER INFORMATION: DWD1-deepF

<400> SEQUENCE: 50
acactctttc cctacacgac gctcttccga tctctgccac aaccaacgga tc         52

<210> SEQ ID NO 51
<211> LENGTH: 52
<212> TYPE: DNA

```
<213> ORGANISM: Artificial Sequence
<220> FEATURE:
<223> OTHER INFORMATION: DWD1-deepR

<400> SEQUENCE: 51
gtgactggag ttcagacgtg tgctcttccg atcttggatt cagacccacc cg        52

<210> SEQ ID NO 52
<211> LENGTH: 53
<212> TYPE: DNA
<213> ORGANISM: Artificial Sequence
<220> FEATURE:
<223> OTHER INFORMATION: BRI1-TS1-deepF

<400> SEQUENCE: 52
acactctttc cctacacgac gctcttccga tctttgcgga tcttcttcag gct       53

<210> SEQ ID NO 53
<211> LENGTH: 54
<212> TYPE: DNA
<213> ORGANISM: Artificial Sequence
<220> FEATURE:
<223> OTHER INFORMATION: BRI1-TS1-deepR

<400> SEQUENCE: 53
gtgactggag ttcagacgtg tgctcttccg atctgctcgt ctccaacttt gcaa      54

<210> SEQ ID NO 54
<211> LENGTH: 53
<212> TYPE: DNA
<213> ORGANISM: Artificial Sequence
<220> FEATURE:
<223> OTHER INFORMATION: BRI1-TS2-deepF

<400> SEQUENCE: 54
acactctttc cctacacgac gctcttccga tctttgcaaa gttggagacg agc       53

<210> SEQ ID NO 55
<211> LENGTH: 54
<212> TYPE: DNA
<213> ORGANISM: Artificial Sequence
<220> FEATURE:
<223> OTHER INFORMATION: BRI1-TS2-deepR

<400> SEQUENCE: 55
gtgactggag ttcagacgtg tgctcttccg atctatctga aacccgagct tcca      54

<210> SEQ ID NO 56
<211> LENGTH: 55
<212> TYPE: DNA
<213> ORGANISM: Artificial Sequence
<220> FEATURE:
<223> OTHER INFORMATION: BIN2-deepF

<400> SEQUENCE: 56
acactctttc cctacacgac gctcttccga tcttgtggtt tctttgaagc attgt     55

<210> SEQ ID NO 57
<211> LENGTH: 54
<212> TYPE: DNA
<213> ORGANISM: Artificial Sequence
<220> FEATURE:
<223> OTHER INFORMATION: BIN2-deepR

<400> SEQUENCE: 57
gtgactggag ttcagacgtg tgctcttccg atcttgccac tcacaatcac atgt      54
```

<210> SEQ ID NO 58
<211> LENGTH: 53
<212> TYPE: DNA
<213> ORGANISM: Artificial Sequence
<220> FEATURE:
<223> OTHER INFORMATION: PHYB-OT1-deepF

<400> SEQUENCE: 58
acactctttc cctacacgac gctcttccga tctttcatga aggtggctca ggt        53

<210> SEQ ID NO 59
<211> LENGTH: 54
<212> TYPE: DNA
<213> ORGANISM: Artificial Sequence
<220> FEATURE:
<223> OTHER INFORMATION: PHYB-OT1-deepR

<400> SEQUENCE: 59
gtgactggag ttcagacgtg tgctcttccg atctcttcat tctcttgccg tggg        54

<210> SEQ ID NO 60
<211> LENGTH: 54
<212> TYPE: DNA
<213> ORGANISM: Artificial Sequence
<220> FEATURE:
<223> OTHER INFORMATION: PHYB-OT2-deepF

<400> SEQUENCE: 60
acactctttc cctacacgac gctcttccga tctggtgaca atgtggctaa tggt        54

<210> SEQ ID NO 61
<211> LENGTH: 54
<212> TYPE: DNA
<213> ORGANISM: Artificial Sequence
<220> FEATURE:
<223> OTHER INFORMATION: PHYB-OT2-deepR

<400> SEQUENCE: 61
gtgactggag ttcagacgtg tgctcttccg atctactcgg ccaatgttac tcca        54

<210> SEQ ID NO 62
<211> LENGTH: 53
<212> TYPE: DNA
<213> ORGANISM: Artificial Sequence
<220> FEATURE:
<223> OTHER INFORMATION: PHYB-OT3-deepF

<400> SEQUENCE: 62
acactctttc cctacacgac gctcttccga tctggcttgt tgggtgatct tga        53

<210> SEQ ID NO 63
<211> LENGTH: 54
<212> TYPE: DNA
<213> ORGANISM: Artificial Sequence
<220> FEATURE:
<223> OTHER INFORMATION: PHYB-OT3-deepR

<400> SEQUENCE: 63
gtgactggag ttcagacgtg tgctcttccg atctgaccca cttcacagaa agca        54

<210> SEQ ID NO 64
<211> LENGTH: 54
<212> TYPE: DNA
<213> ORGANISM: Artificial Sequence
<220> FEATURE:

<223> OTHER INFORMATION: BRI-TS1-OT1-deepF

<400> SEQUENCE: 64
acactctttc cctacacgac gctcttccga tcttctgcac gattctacct gaca         54

<210> SEQ ID NO 65
<211> LENGTH: 56
<212> TYPE: DNA
<213> ORGANISM: Artificial Sequence
<220> FEATURE:
<223> OTHER INFORMATION: BRI-TS1-OT1-deepR

<400> SEQUENCE: 65
gtgactggag ttcagacgtg tgctcttccg atcttctcct gtcatgtgtt cctaac       56

<210> SEQ ID NO 66
<211> LENGTH: 53
<212> TYPE: DNA
<213> ORGANISM: Artificial Sequence
<220> FEATURE:
<223> OTHER INFORMATION: BRI-TS1-OT2-deepF

<400> SEQUENCE: 66
acactctttc cctacacgac gctcttccga tcttagctat gccggtggaa gtt          53

<210> SEQ ID NO 67
<211> LENGTH: 55
<212> TYPE: DNA
<213> ORGANISM: Artificial Sequence
<220> FEATURE:
<223> OTHER INFORMATION: BRI-TS1-OT2-deepR

<400> SEQUENCE: 67
gtgactggag ttcagacgtg tgctcttccg atctacagaa gtagccattc cgaga        55

<210> SEQ ID NO 68
<211> LENGTH: 53
<212> TYPE: DNA
<213> ORGANISM: Artificial Sequence
<220> FEATURE:
<223> OTHER INFORMATION: BRI-TS1-OT3-deepF

<400> SEQUENCE: 68
acactctttc cctacacgac gctcttccga tctcggagac ctttaagctt cgc          53

<210> SEQ ID NO 69
<211> LENGTH: 54
<212> TYPE: DNA
<213> ORGANISM: Artificial Sequence
<220> FEATURE:
<223> OTHER INFORMATION: BRI-TS1-OT3-deepR

<400> SEQUENCE: 69
gtgactggag ttcagacgtg tgctcttccg atcttgcaaa accatcagca gtgg         54

<210> SEQ ID NO 70
<211> LENGTH: 53
<212> TYPE: DNA
<213> ORGANISM: Artificial Sequence
<220> FEATURE:
<223> OTHER INFORMATION: BRI-TS1-OT4-deepF

<400> SEQUENCE: 70
acactctttc cctacacgac gctcttccga tctgtttgaa gaaggtggcc cag          53

```
<210> SEQ ID NO 71
<211> LENGTH: 54
<212> TYPE: DNA
<213> ORGANISM: Artificial Sequence
<220> FEATURE:
<223> OTHER INFORMATION: BRI-TS1-OT4-deepR

<400> SEQUENCE: 71
gtgactggag ttcagacgtg tgctcttccg atctggtggg acgatcgagc ttat          54

<210> SEQ ID NO 72
<211> LENGTH: 53
<212> TYPE: DNA
<213> ORGANISM: Artificial Sequence
<220> FEATURE:
<223> OTHER INFORMATION: BRI-TS1-OT5-deepF

<400> SEQUENCE: 72
acactctttc cctacacgac gctcttccga tcttgactaa ccgcttgtcc tca           53

<210> SEQ ID NO 73
<211> LENGTH: 54
<212> TYPE: DNA
<213> ORGANISM: Artificial Sequence
<220> FEATURE:
<223> OTHER INFORMATION: BRI-TS1-OT5-deepR

<400> SEQUENCE: 73
gtgactggag ttcagacgtg tgctcttccg atctacgttg ccagtaaagt tcgc          54

<210> SEQ ID NO 74
<211> LENGTH: 53
<212> TYPE: DNA
<213> ORGANISM: Artificial Sequence
<220> FEATURE:
<223> OTHER INFORMATION: BRI-TS1-OT6-deepF

<400> SEQUENCE: 74
acactctttc cctacacgac gctcttccga tctcgtctct tactcgcctc ctt           53

<210> SEQ ID NO 75
<211> LENGTH: 55
<212> TYPE: DNA
<213> ORGANISM: Artificial Sequence
<220> FEATURE:
<223> OTHER INFORMATION: BRI-TS1-OT6-deepR

<400> SEQUENCE: 75
gtgactggag ttcagacgtg tgctcttccg atcttcatct gaggttggtt cgaca         55

<210> SEQ ID NO 76
<211> LENGTH: 54
<212> TYPE: DNA
<213> ORGANISM: Artificial Sequence
<220> FEATURE:
<223> OTHER INFORMATION: BRI-TS2-OT1-deepF

<400> SEQUENCE: 76
acactctttc cctacacgac gctcttccga tcttcattca gctttgccaa acca          54

<210> SEQ ID NO 77
<211> LENGTH: 54
<212> TYPE: DNA
<213> ORGANISM: Artificial Sequence
<220> FEATURE:
<223> OTHER INFORMATION: BRI-TS2-OT1-deepR
```

<400> SEQUENCE: 77
gtgactggag ttcagacgtg tgctcttccg atcttccggt ggaattactg ctca          54

<210> SEQ ID NO 78
<211> LENGTH: 54
<212> TYPE: DNA
<213> ORGANISM: Artificial Sequence
<220> FEATURE:
<223> OTHER INFORMATION: BRI-TS2-OT2-deepF

<400> SEQUENCE: 78
acactctttc cctacacgac gctcttccga tcttgttcac aattactgcc acca          54

<210> SEQ ID NO 79
<211> LENGTH: 55
<212> TYPE: DNA
<213> ORGANISM: Artificial Sequence
<220> FEATURE:
<223> OTHER INFORMATION: BRI-TS2-OT2-deepR

<400> SEQUENCE: 79
gtgactggag ttcagacgtg tgctcttccg atctactctc tacgatcgca actct         55

<210> SEQ ID NO 80
<211> LENGTH: 53
<212> TYPE: DNA
<213> ORGANISM: Artificial Sequence
<220> FEATURE:
<223> OTHER INFORMATION: BRI-TS2-OT3-deepF

<400> SEQUENCE: 80
acactctttc cctacacgac gctcttccga tctggagatg gaggggatgg aac           53

<210> SEQ ID NO 81
<211> LENGTH: 54
<212> TYPE: DNA
<213> ORGANISM: Artificial Sequence
<220> FEATURE:
<223> OTHER INFORMATION: BRI-TS2-OT3-deepR

<400> SEQUENCE: 81
gtgactggag ttcagacgtg tgctcttccg atctcggctc tgaacaggtc taca          54

<210> SEQ ID NO 82
<211> LENGTH: 53
<212> TYPE: DNA
<213> ORGANISM: Artificial Sequence
<220> FEATURE:
<223> OTHER INFORMATION: BRI-TS2-OT4-deepF

<400> SEQUENCE: 82
acactctttc cctacacgac gctcttccga tcttgcaatc agatgtccgg tca           53

<210> SEQ ID NO 83
<211> LENGTH: 55
<212> TYPE: DNA
<213> ORGANISM: Artificial Sequence
<220> FEATURE:
<223> OTHER INFORMATION: BRI-TS2-OT4-deepR

<400> SEQUENCE: 83
gtgactggag ttcagacgtg tgctcttccg atctgtacct cttcagcaac caagt         55

<210> SEQ ID NO 84
<211> LENGTH: 66

```
<212> TYPE: DNA
<213> ORGANISM: Artificial Sequence
<220> FEATURE:
<223> OTHER INFORMATION: AOC-sgF

<400> SEQUENCE: 84
gaaattaata cgactcacta tagcaaaaga ctgtcaattc cctgtttag agctagaaat      60 agcaag                                                                66

<210> SEQ ID NO 85
<211> LENGTH: 67
<212> TYPE: DNA
<213> ORGANISM: Artificial Sequence
<220> FEATURE:
<223> OTHER INFORMATION: PHYB-sgF

<400> SEQUENCE: 85
gaaattaata cgactcacta taggcactag gagcaacacc caacgtttta gagctagaaa      60
tagcaag                                                                67

<210> SEQ ID NO 86
<211> LENGTH: 67
<212> TYPE: DNA
<213> ORGANISM: Artificial Sequence
<220> FEATURE:
<223> OTHER INFORMATION: P450-sgF

<400> SEQUENCE: 86
gaaattaata cgactcacta taggcatata gttgggtcat ggcagtttta gagctagaaa      60
tagcaag                                                                67

<210> SEQ ID NO 87
<211> LENGTH: 67
<212> TYPE: DNA
<213> ORGANISM: Artificial Sequence
<220> FEATURE:
<223> OTHER INFORMATION: DWD1-TS1-sgF

<400> SEQUENCE: 87
gaaattaata cgactcacta taggtgcatc gtccaagcgc acaggtttta gagctagaaa      60
tagcaag                                                                67

<210> SEQ ID NO 88
<211> LENGTH: 67
<212> TYPE: DNA
<213> ORGANISM: Artificial Sequence
<220> FEATURE:
<223> OTHER INFORMATION: DWD1-TS2-sgF

<400> SEQUENCE: 88
gaaattaata cgactcacta taggctacga cgtcaggttc taccgtttta gagctagaaa      60
tagcaag                                                                67

<210> SEQ ID NO 89
<211> LENGTH: 67
<212> TYPE: DNA
<213> ORGANISM: Artificial Sequence
<220> FEATURE:
<223> OTHER INFORMATION: BRI1-TS1-sgF

<400> SEQUENCE: 89
gaaattaata cgactcacta taggtttgaa agatggaagc gcgggtttta gagctagaaa      60
``` tagcaag 67

<210> SEQ ID NO 90
<211> LENGTH: 67
<212> TYPE: DNA
<213> ORGANISM: Artificial Sequence
<220> FEATURE:
<223> OTHER INFORMATION: BRI1-TS2-sgF

<400> SEQUENCE: 90
gaaattaata cgactcacta taggtgaaac taaactggtc cacagtttta gagctagaaa 60
tagcaag 67

<210> SEQ ID NO 91
<211> LENGTH: 66
<212> TYPE: DNA
<213> ORGANISM: Artificial Sequence
<220> FEATURE:
<223> OTHER INFORMATION: BIN2-sgF

<400> SEQUENCE: 91
gaaattaata cgactcacta tagatcacag tgatgctcgt caagttttag agctagaaat 60
agcaag 66

<210> SEQ ID NO 92
<211> LENGTH: 82
<212> TYPE: DNA
<213> ORGANISM: Artificial Sequence
<220> FEATURE:
<223> OTHER INFORMATION: Universal sgR

<400> SEQUENCE: 92
aaaaaagcac cgactcggtg ccactttttc aagttgataa cggactagcc ttattttaac 60
ttgctatttc tagctctaaa ac 82

<210> SEQ ID NO 93
<211> LENGTH: 20
<212> TYPE: DNA
<213> ORGANISM: Artificial Sequence
<220> FEATURE:
<223> OTHER INFORMATION: BIN2 target site

<400> SEQUENCE: 93
atcacagtga tgctcgtcaa 20

<210> SEQ ID NO 94
<211> LENGTH: 23
<212> TYPE: DNA
<213> ORGANISM: Artificial Sequence
<220> FEATURE:
<223> OTHER INFORMATION: on-target

<400> SEQUENCE: 94
atcacagtga tgctcgtcaa agg 23

<210> SEQ ID NO 95
<211> LENGTH: 23
<212> TYPE: DNA
<213> ORGANISM: Artificial Sequence
<220> FEATURE:
<223> OTHER INFORMATION: OT1

<400> SEQUENCE: 95
atcacagtgc ggctcgtcaa ggg 23

<210> SEQ ID NO 96
<211> LENGTH: 23
<212> TYPE: DNA
<213> ORGANISM: Artificial Sequence
<220> FEATURE:
<223> OTHER INFORMATION: OT2

<400> SEQUENCE: 96
cacacagtga tgttcgtcaa ggg                                           23

<210> SEQ ID NO 97
<211> LENGTH: 23
<212> TYPE: DNA
<213> ORGANISM: Artificial Sequence
<220> FEATURE:
<223> OTHER INFORMATION: OT3

<400> SEQUENCE: 97
ataccaggga tgctcgtcaa tgg                                           23

<210> SEQ ID NO 98
<211> LENGTH: 23
<212> TYPE: DNA
<213> ORGANISM: Artificial Sequence
<220> FEATURE:
<223> OTHER INFORMATION: OT4

<400> SEQUENCE: 98
atcatagtga tgctcatgaa ggg                                           23

<210> SEQ ID NO 99
<211> LENGTH: 23
<212> TYPE: DNA
<213> ORGANISM: Artificial Sequence
<220> FEATURE:
<223> OTHER INFORMATION: OT5

<400> SEQUENCE: 99
atcacattga tgctctacat agg                                           23

<210> SEQ ID NO 100
<211> LENGTH: 23
<212> TYPE: DNA
<213> ORGANISM: Artificial Sequence
<220> FEATURE:
<223> OTHER INFORMATION: OT6

<400> SEQUENCE: 100
ataacagaga cgatcgtcaa agg                                           23

<210> SEQ ID NO 101
<211> LENGTH: 23
<212> TYPE: DNA
<213> ORGANISM: Artificial Sequence
<220> FEATURE:
<223> OTHER INFORMATION: OT7

<400> SEQUENCE: 101
atcacactga tgccctacaa agg                                           23

<210> SEQ ID NO 102
<211> LENGTH: 23
<212> TYPE: DNA
<213> ORGANISM: Artificial Sequence
<220> FEATURE:

<223> OTHER INFORMATION: OT8

<400> SEQUENCE: 102
atcacattga ggcccgacaa agg                                         23

<210> SEQ ID NO 103
<211> LENGTH: 23
<212> TYPE: DNA
<213> ORGANISM: Artificial Sequence
<220> FEATURE:
<223> OTHER INFORMATION: OT9

<400> SEQUENCE: 103
atcacactga tgcactacaa agg                                         23

<210> SEQ ID NO 104
<211> LENGTH: 23
<212> TYPE: DNA
<213> ORGANISM: Artificial Sequence
<220> FEATURE:
<223> OTHER INFORMATION: OT10

<400> SEQUENCE: 104
cacacagtga tgttcatcaa agg                                         23

<210> SEQ ID NO 105
<211> LENGTH: 23
<212> TYPE: DNA
<213> ORGANISM: Artificial Sequence
<220> FEATURE:
<223> OTHER INFORMATION: OT11

<400> SEQUENCE: 105
atgacaatta tgctcttcaa agg                                         23

<210> SEQ ID NO 106
<211> LENGTH: 23
<212> TYPE: DNA
<213> ORGANISM: Artificial Sequence
<220> FEATURE:
<223> OTHER INFORMATION: OT12

<400> SEQUENCE: 106
atcaaagtgc tcctcgtgaa agg                                         23

<210> SEQ ID NO 107
<211> LENGTH: 23
<212> TYPE: DNA
<213> ORGANISM: Artificial Sequence
<220> FEATURE:
<223> OTHER INFORMATION: OT13

<400> SEQUENCE: 107
tacacaatgt tgctcgtcaa cgg                                         23

<210> SEQ ID NO 108
<211> LENGTH: 23
<212> TYPE: DNA
<213> ORGANISM: Artificial Sequence
<220> FEATURE:
<223> OTHER INFORMATION: OT14

<400> SEQUENCE: 108
gccacagtga tgatcgtcga cgg                                         23

```
<210> SEQ ID NO 109
<211> LENGTH: 23
<212> TYPE: DNA
<213> ORGANISM: Artificial Sequence
<220> FEATURE:
<223> OTHER INFORMATION: OT15

<400> SEQUENCE: 109
atatcaggga tgctcgccaa tgg                                              23

<210> SEQ ID NO 110
<211> LENGTH: 23
<212> TYPE: DNA
<213> ORGANISM: Artificial Sequence
<220> FEATURE:
<223> OTHER INFORMATION: OT16

<400> SEQUENCE: 110
aaatcagtga tcctcgtcaa cgg                                              23

<210> SEQ ID NO 111
<211> LENGTH: 23
<212> TYPE: DNA
<213> ORGANISM: Artificial Sequence
<220> FEATURE:
<223> OTHER INFORMATION: OT17

<400> SEQUENCE: 111
atggcagtga tggtcgtgaa ggg                                              23

<210> SEQ ID NO 112
<211> LENGTH: 23
<212> TYPE: DNA
<213> ORGANISM: Artificial Sequence
<220> FEATURE:
<223> OTHER INFORMATION: OT18

<400> SEQUENCE: 112
ctcagagtgt tgctcttcaa tgg                                              23

<210> SEQ ID NO 113
<211> LENGTH: 23
<212> TYPE: DNA
<213> ORGANISM: Artificial Sequence
<220> FEATURE:
<223> OTHER INFORMATION: OT19

<400> SEQUENCE: 113
atcacagaga tgctccaaaa tgg                                              23

<210> SEQ ID NO 114
<211> LENGTH: 23
<212> TYPE: DNA
<213> ORGANISM: Artificial Sequence
<220> FEATURE:
<223> OTHER INFORMATION: OT20

<400> SEQUENCE: 114
atcaaggtta ttctcgtcaa ggg                                              23

<210> SEQ ID NO 115
<211> LENGTH: 23
<212> TYPE: DNA
<213> ORGANISM: Artificial Sequence
<220> FEATURE:
<223> OTHER INFORMATION: OT21
```

<400> SEQUENCE: 115
agcacagtga ggcttgtcga ggg                                          23

<210> SEQ ID NO 116
<211> LENGTH: 23
<212> TYPE: DNA
<213> ORGANISM: Artificial Sequence
<220> FEATURE:
<223> OTHER INFORMATION: OT22

<400> SEQUENCE: 116
atatcaagga tgctcgtcaa tgg                                          23

<210> SEQ ID NO 117
<211> LENGTH: 23
<212> TYPE: DNA
<213> ORGANISM: Artificial Sequence
<220> FEATURE:
<223> OTHER INFORMATION: OT23

<400> SEQUENCE: 117
ttcccagaga tgctcttcaa ggg                                          23

<210> SEQ ID NO 118
<211> LENGTH: 23
<212> TYPE: DNA
<213> ORGANISM: Artificial Sequence
<220> FEATURE:
<223> OTHER INFORMATION: OT24

<400> SEQUENCE: 118
gtcacattga tgctcatcat ggg                                          23

<210> SEQ ID NO 119
<211> LENGTH: 23
<212> TYPE: DNA
<213> ORGANISM: Artificial Sequence
<220> FEATURE:
<223> OTHER INFORMATION: OT25

<400> SEQUENCE: 119
atcacagaga tgttcatcat cgg                                          23

<210> SEQ ID NO 120
<211> LENGTH: 23
<212> TYPE: DNA
<213> ORGANISM: Artificial Sequence
<220> FEATURE:
<223> OTHER INFORMATION: OT26

<400> SEQUENCE: 120
atcaaaatga ggctcgacaa cgg                                          23

<210> SEQ ID NO 121
<211> LENGTH: 23
<212> TYPE: DNA
<213> ORGANISM: Artificial Sequence
<220> FEATURE:
<223> OTHER INFORMATION: OT27

<400> SEQUENCE: 121
ataacaatga agctcgttaa tgg                                          23

<210> SEQ ID NO 122
<211> LENGTH: 23

```
<212> TYPE: DNA
<213> ORGANISM: Artificial Sequence
<220> FEATURE:
<223> OTHER INFORMATION: OT28

<400> SEQUENCE: 122
atatcaggga tgctcatcaa tgg                                              23

<210> SEQ ID NO 123
<211> LENGTH: 23
<212> TYPE: DNA
<213> ORGANISM: Artificial Sequence
<220> FEATURE:
<223> OTHER INFORMATION: OT29

<400> SEQUENCE: 123
atcatattga agcacttcaa agg                                              23

<210> SEQ ID NO 124
<211> LENGTH: 23
<212> TYPE: DNA
<213> ORGANISM: Artificial Sequence
<220> FEATURE:
<223> OTHER INFORMATION: OT30

<400> SEQUENCE: 124
ctcacattga tgcactacaa agg                                              23

<210> SEQ ID NO 125
<211> LENGTH: 23
<212> TYPE: DNA
<213> ORGANISM: Artificial Sequence
<220> FEATURE:
<223> OTHER INFORMATION: OT31

<400> SEQUENCE: 125
tccacaatga tgcacttcaa agg                                              23

<210> SEQ ID NO 126
<211> LENGTH: 23
<212> TYPE: DNA
<213> ORGANISM: Artificial Sequence
<220> FEATURE:
<223> OTHER INFORMATION: OT32

<400> SEQUENCE: 126
ctcacaatgt tgctctacaa agg                                              23

<210> SEQ ID NO 127
<211> LENGTH: 23
<212> TYPE: DNA
<213> ORGANISM: Artificial Sequence
<220> FEATURE:
<223> OTHER INFORMATION: OT33

<400> SEQUENCE: 127
atgacaatga agctcgtaat agg                                              23

<210> SEQ ID NO 128
<211> LENGTH: 23
<212> TYPE: DNA
<213> ORGANISM: Artificial Sequence
<220> FEATURE:
<223> OTHER INFORMATION: OT34

<400> SEQUENCE: 128
```

```
ctctcagtgg tgctggtcga agg                                              23

<210> SEQ ID NO 129
<211> LENGTH: 23
<212> TYPE: DNA
<213> ORGANISM: Artificial Sequence
<220> FEATURE:
<223> OTHER INFORMATION: OT35

<400> SEQUENCE: 129
atcacactta tactcgacag agg                                              23

<210> SEQ ID NO 130
<211> LENGTH: 23
<212> TYPE: DNA
<213> ORGANISM: Artificial Sequence
<220> FEATURE:
<223> OTHER INFORMATION: OT36

<400> SEQUENCE: 130
ctcacagtga ggcttttaaa agg                                              23

<210> SEQ ID NO 131
<211> LENGTH: 23
<212> TYPE: DNA
<213> ORGANISM: Artificial Sequence
<220> FEATURE:
<223> OTHER INFORMATION: OT37

<400> SEQUENCE: 131
atcactgtga tgttcgggag agg                                              23

<210> SEQ ID NO 132
<211> LENGTH: 23
<212> TYPE: DNA
<213> ORGANISM: Artificial Sequence
<220> FEATURE:
<223> OTHER INFORMATION: OT38

<400> SEQUENCE: 132
ctctcggtgg tgctggtcaa agg                                              23

<210> SEQ ID NO 133
<211> LENGTH: 23
<212> TYPE: DNA
<213> ORGANISM: Artificial Sequence
<220> FEATURE:
<223> OTHER INFORMATION: OT39

<400> SEQUENCE: 133
gtgacagtca tgcacgtcca agg                                              23

<210> SEQ ID NO 134
<211> LENGTH: 23
<212> TYPE: DNA
<213> ORGANISM: Artificial Sequence
<220> FEATURE:
<223> OTHER INFORMATION: OT40

<400> SEQUENCE: 134
atcacactga ttccctacaa agg                                              23

<210> SEQ ID NO 135
<211> LENGTH: 23
<212> TYPE: DNA
<213> ORGANISM: Artificial Sequence
```

-continued

```
<220> FEATURE:
<223> OTHER INFORMATION: OT41

<400> SEQUENCE: 135
atgagagtga ttttcgttaa agg                                           23

<210> SEQ ID NO 136
<211> LENGTH: 23
<212> TYPE: DNA
<213> ORGANISM: Artificial Sequence
<220> FEATURE:
<223> OTHER INFORMATION: OT42

<400> SEQUENCE: 136
atcactgtga tgtttaccaa agg                                           23

<210> SEQ ID NO 137
<211> LENGTH: 23
<212> TYPE: DNA
<213> ORGANISM: Artificial Sequence
<220> FEATURE:
<223> OTHER INFORMATION: OT43

<400> SEQUENCE: 137
atcacagtga tgcttccaca agg                                           23

<210> SEQ ID NO 138
<211> LENGTH: 23
<212> TYPE: DNA
<213> ORGANISM: Artificial Sequence
<220> FEATURE:
<223> OTHER INFORMATION: OT44

<400> SEQUENCE: 138
gtaacagtgg tgttcgacaa agg                                           23

<210> SEQ ID NO 139
<211> LENGTH: 23
<212> TYPE: DNA
<213> ORGANISM: Artificial Sequence
<220> FEATURE:
<223> OTHER INFORMATION: OT45

<400> SEQUENCE: 139
atcccaatca ggctcttcaa agg                                           23

<210> SEQ ID NO 140
<211> LENGTH: 23
<212> TYPE: DNA
<213> ORGANISM: Artificial Sequence
<220> FEATURE:
<223> OTHER INFORMATION: OT46

<400> SEQUENCE: 140
ctcacactga tgcacttcat agg                                           23

<210> SEQ ID NO 141
<211> LENGTH: 23
<212> TYPE: DNA
<213> ORGANISM: Artificial Sequence
<220> FEATURE:
<223> OTHER INFORMATION: OT47

<400> SEQUENCE: 141
aacacactga ggctctgcaa agg                                           23
```

```
<210> SEQ ID NO 142
<211> LENGTH: 23
<212> TYPE: DNA
<213> ORGANISM: Artificial Sequence
<220> FEATURE:
<223> OTHER INFORMATION: OT48

<400> SEQUENCE: 142
atggcactga tgcacgacaa agg                                              23

<210> SEQ ID NO 143
<211> LENGTH: 23
<212> TYPE: DNA
<213> ORGANISM: Artificial Sequence
<220> FEATURE:
<223> OTHER INFORMATION: OT49

<400> SEQUENCE: 143
cacactgtca tgttcgtcaa agg                                              23

<210> SEQ ID NO 144
<211> LENGTH: 23
<212> TYPE: DNA
<213> ORGANISM: Artificial Sequence
<220> FEATURE:
<223> OTHER INFORMATION: OT50

<400> SEQUENCE: 144
ttgacagtgt tcctagtcaa agg                                              23

<210> SEQ ID NO 145
<211> LENGTH: 23
<212> TYPE: DNA
<213> ORGANISM: Artificial Sequence
<220> FEATURE:
<223> OTHER INFORMATION: OT51

<400> SEQUENCE: 145
atcataggta tgttggtcaa agg                                              23

<210> SEQ ID NO 146
<211> LENGTH: 23
<212> TYPE: DNA
<213> ORGANISM: Artificial Sequence
<220> FEATURE:
<223> OTHER INFORMATION: OT52

<400> SEQUENCE: 146
atcacactga tgccctacat agg                                              23

<210> SEQ ID NO 147
<211> LENGTH: 23
<212> TYPE: DNA
<213> ORGANISM: Artificial Sequence
<220> FEATURE:
<223> OTHER INFORMATION: OT53

<400> SEQUENCE: 147
atcacactga ttccctgcaa agg                                              23

<210> SEQ ID NO 148
<211> LENGTH: 23
<212> TYPE: DNA
<213> ORGANISM: Artificial Sequence
<220> FEATURE:
<223> OTHER INFORMATION: OT54
```

<400> SEQUENCE: 148
aacatagcgt tgctagtcaa agg                                    23

<210> SEQ ID NO 149
<211> LENGTH: 23
<212> TYPE: DNA
<213> ORGANISM: Artificial Sequence
<220> FEATURE:
<223> OTHER INFORMATION: OT55

<400> SEQUENCE: 149
atcacatgga tcctcctgaa agg                                    23

<210> SEQ ID NO 150
<211> LENGTH: 23
<212> TYPE: DNA
<213> ORGANISM: Artificial Sequence
<220> FEATURE:
<223> OTHER INFORMATION: OT56

<400> SEQUENCE: 150
ttttcaatga tgctcatcaa agg                                    23

<210> SEQ ID NO 151
<211> LENGTH: 23
<212> TYPE: DNA
<213> ORGANISM: Artificial Sequence
<220> FEATURE:
<223> OTHER INFORMATION: OT57

<400> SEQUENCE: 151
ttctctgtca tgttcgtcaa agg                                    23

<210> SEQ ID NO 152
<211> LENGTH: 23
<212> TYPE: DNA
<213> ORGANISM: Artificial Sequence
<220> FEATURE:
<223> OTHER INFORMATION: OT58

<400> SEQUENCE: 152
atcacagtat tggtccacaa agg                                    23

<210> SEQ ID NO 153
<211> LENGTH: 23
<212> TYPE: DNA
<213> ORGANISM: Artificial Sequence
<220> FEATURE:
<223> OTHER INFORMATION: OT59

<400> SEQUENCE: 153
atgctagaga tgcttgtcaa agg                                    23

<210> SEQ ID NO 154
<211> LENGTH: 23
<212> TYPE: DNA
<213> ORGANISM: Artificial Sequence
<220> FEATURE:
<223> OTHER INFORMATION: OT60

<400> SEQUENCE: 154
atcacactga tgcactacag agg                                    23

<210> SEQ ID NO 155

```
<211> LENGTH: 23
<212> TYPE: DNA
<213> ORGANISM: Artificial Sequence
<220> FEATURE:
<223> OTHER INFORMATION: OT61

<400> SEQUENCE: 155
ctcacactga tgcactacaa agg                                              23

<210> SEQ ID NO 156
<211> LENGTH: 23
<212> TYPE: DNA
<213> ORGANISM: Artificial Sequence
<220> FEATURE:
<223> OTHER INFORMATION: OT62

<400> SEQUENCE: 156
ttgatagtgt tcctcgtcaa agg                                              23

<210> SEQ ID NO 157
<211> LENGTH: 23
<212> TYPE: DNA
<213> ORGANISM: Artificial Sequence
<220> FEATURE:
<223> OTHER INFORMATION: OT63

<400> SEQUENCE: 157
atcacagata tcatggtcaa agg                                              23

<210> SEQ ID NO 158
<211> LENGTH: 23
<212> TYPE: DNA
<213> ORGANISM: Artificial Sequence
<220> FEATURE:
<223> OTHER INFORMATION: OT64

<400> SEQUENCE: 158
atcttagtca agctagtcaa agg                                              23

<210> SEQ ID NO 159
<211> LENGTH: 23
<212> TYPE: DNA
<213> ORGANISM: Artificial Sequence
<220> FEATURE:
<223> OTHER INFORMATION: OT65

<400> SEQUENCE: 159
atcagattta tgctcattaa agg                                              23

<210> SEQ ID NO 160
<211> LENGTH: 23
<212> TYPE: DNA
<213> ORGANISM: Artificial Sequence
<220> FEATURE:
<223> OTHER INFORMATION: OT66

<400> SEQUENCE: 160
atctgagtga tcttcgtcga agg                                              23

<210> SEQ ID NO 161
<211> LENGTH: 23
<212> TYPE: DNA
<213> ORGANISM: Artificial Sequence
<220> FEATURE:
<223> OTHER INFORMATION: OT67

<400> SEQUENCE: 161
```
atggcagtgt tcctagtcaa agg                                            23

<210> SEQ ID NO 162
<211> LENGTH: 23
<212> TYPE: DNA
<213> ORGANISM: Artificial Sequence
<220> FEATURE:
<223> OTHER INFORMATION: OT68

<400> SEQUENCE: 162
atcacattta tgcttatcta agg                                            23

<210> SEQ ID NO 163
<211> LENGTH: 23
<212> TYPE: DNA
<213> ORGANISM: Artificial Sequence
<220> FEATURE:
<223> OTHER INFORMATION: OT69

<400> SEQUENCE: 163
tccacagtgt tcctagtcaa agg                                            23

<210> SEQ ID NO 164
<211> LENGTH: 23
<212> TYPE: DNA
<213> ORGANISM: Artificial Sequence
<220> FEATURE:
<223> OTHER INFORMATION: OT70

<400> SEQUENCE: 164
ttcttaggga tggtcgtcaa agg                                            23

<210> SEQ ID NO 165
<211> LENGTH: 23
<212> TYPE: DNA
<213> ORGANISM: Artificial Sequence
<220> FEATURE:
<223> OTHER INFORMATION: OT71

<400> SEQUENCE: 165
aacacagtca tgctcaccag agg                                            23

<210> SEQ ID NO 166
<211> LENGTH: 23
<212> TYPE: DNA
<213> ORGANISM: Artificial Sequence
<220> FEATURE:
<223> OTHER INFORMATION: OT72

<400> SEQUENCE: 166
aaaagagtga tgcttatcaa agg                                            23

<210> SEQ ID NO 167
<211> LENGTH: 23
<212> TYPE: DNA
<213> ORGANISM: Artificial Sequence
<220> FEATURE:
<223> OTHER INFORMATION: OT73

<400> SEQUENCE: 167
cttccagtga tgatagtcaa agg                                            23

<210> SEQ ID NO 168
<211> LENGTH: 23
<212> TYPE: DNA

<213> ORGANISM: Artificial Sequence
<220> FEATURE:
<223> OTHER INFORMATION: OT74

<400> SEQUENCE: 168
atcaaagtga gatacgtcaa agg                                              23

<210> SEQ ID NO 169
<211> LENGTH: 23
<212> TYPE: DNA
<213> ORGANISM: Artificial Sequence
<220> FEATURE:
<223> OTHER INFORMATION: OT75

<400> SEQUENCE: 169
atgatattga cgcttgtcaa agg                                              23

<210> SEQ ID NO 170
<211> LENGTH: 23
<212> TYPE: DNA
<213> ORGANISM: Artificial Sequence
<220> FEATURE:
<223> OTHER INFORMATION: OT76

<400> SEQUENCE: 170
atcacgctga tgggcctcaa agg                                              23

<210> SEQ ID NO 171
<211> LENGTH: 23
<212> TYPE: DNA
<213> ORGANISM: Artificial Sequence
<220> FEATURE:
<223> OTHER INFORMATION: OT77

<400> SEQUENCE: 171
atagatgtga tgcttgtcaa agg                                              23

<210> SEQ ID NO 172
<211> LENGTH: 23
<212> TYPE: DNA
<213> ORGANISM: Artificial Sequence
<220> FEATURE:
<223> OTHER INFORMATION: OT78

<400> SEQUENCE: 172
gtcccattga tgcacgacaa agg                                              23

<210> SEQ ID NO 173
<211> LENGTH: 23
<212> TYPE: DNA
<213> ORGANISM: Artificial Sequence
<220> FEATURE:
<223> OTHER INFORMATION: OT79

<400> SEQUENCE: 173
ttgacaatta tgctcttcaa agg                                              23

<210> SEQ ID NO 174
<211> LENGTH: 23
<212> TYPE: DNA
<213> ORGANISM: Artificial Sequence
<220> FEATURE:
<223> OTHER INFORMATION: OT80

<400> SEQUENCE: 174
attaaaatca tgttcgtcaa agg                                              23

<210> SEQ ID NO 175
<211> LENGTH: 23
<212> TYPE: DNA
<213> ORGANISM: Artificial Sequence
<220> FEATURE:
<223> OTHER INFORMATION: OT81

<400> SEQUENCE: 175
cacacagtca tgttcctcaa agg                                              23

<210> SEQ ID NO 176
<211> LENGTH: 23
<212> TYPE: DNA
<213> ORGANISM: Artificial Sequence
<220> FEATURE:
<223> OTHER INFORMATION: OT82

<400> SEQUENCE: 176
ttgacaatca tgctcttcaa agg                                              23

<210> SEQ ID NO 177
<211> LENGTH: 23
<212> TYPE: DNA
<213> ORGANISM: Artificial Sequence
<220> FEATURE:
<223> OTHER INFORMATION: OT83

<400> SEQUENCE: 177
ttcatagtga tgtttttcaa agg                                              23

<210> SEQ ID NO 178
<211> LENGTH: 23
<212> TYPE: DNA
<213> ORGANISM: Artificial Sequence
<220> FEATURE:
<223> OTHER INFORMATION: OT84

<400> SEQUENCE: 178
atcacgctca tgatcctcaa agg                                              23

<210> SEQ ID NO 179
<211> LENGTH: 23
<212> TYPE: DNA
<213> ORGANISM: Artificial Sequence
<220> FEATURE:
<223> OTHER INFORMATION: OT85

<400> SEQUENCE: 179
atcacactca tggacctcaa agg                                              23

<210> SEQ ID NO 180
<211> LENGTH: 23
<212> TYPE: DNA
<213> ORGANISM: Artificial Sequence
<220> FEATURE:
<223> OTHER INFORMATION: OT86

<400> SEQUENCE: 180
atcatattga agcccttcaa agg                                              23

<210> SEQ ID NO 181
<211> LENGTH: 23
<212> TYPE: DNA
<213> ORGANISM: Artificial Sequence
<220> FEATURE:

<223> OTHER INFORMATION: OT87

<400> SEQUENCE: 181
atcacaatga tggtcgggga agg                                           23

<210> SEQ ID NO 182
<211> LENGTH: 23
<212> TYPE: DNA
<213> ORGANISM: Artificial Sequence
<220> FEATURE:
<223> OTHER INFORMATION: OT88

<400> SEQUENCE: 182
atcataatga agcccttcaa agg                                           23

<210> SEQ ID NO 183
<211> LENGTH: 23
<212> TYPE: DNA
<213> ORGANISM: Artificial Sequence
<220> FEATURE:
<223> OTHER INFORMATION: OT89

<400> SEQUENCE: 183
atgaatgtta tgctcttcaa agg                                           23

<210> SEQ ID NO 184
<211> LENGTH: 23
<212> TYPE: DNA
<213> ORGANISM: Artificial Sequence
<220> FEATURE:
<223> OTHER INFORMATION: OT90

<400> SEQUENCE: 184
atcacactga taccctacaa agg                                           23

<210> SEQ ID NO 185
<211> LENGTH: 23
<212> TYPE: DNA
<213> ORGANISM: Artificial Sequence
<220> FEATURE:
<223> OTHER INFORMATION: OT91

<400> SEQUENCE: 185
aatataatga ttctcgtcaa agg                                           23

<210> SEQ ID NO 186
<211> LENGTH: 23
<212> TYPE: DNA
<213> ORGANISM: Artificial Sequence
<220> FEATURE:
<223> OTHER INFORMATION: OT92

<400> SEQUENCE: 186
atgactgtgt tccttgtcaa agg                                           23

<210> SEQ ID NO 187
<211> LENGTH: 23
<212> TYPE: DNA
<213> ORGANISM: Artificial Sequence
<220> FEATURE:
<223> OTHER INFORMATION: OT93

<400> SEQUENCE: 187
ctcaaagtca tgatcttcaa agg                                           23

<210> SEQ ID NO 188
<211> LENGTH: 23
<212> TYPE: DNA
<213> ORGANISM: Artificial Sequence
<220> FEATURE:
<223> OTHER INFORMATION: OT94

<400> SEQUENCE: 188
ctcaatgaga tgctcgacaa agg                                              23

<210> SEQ ID NO 189
<211> LENGTH: 23
<212> TYPE: DNA
<213> ORGANISM: Artificial Sequence
<220> FEATURE:
<223> OTHER INFORMATION: OT95

<400> SEQUENCE: 189
atcacactta agctcttgaa agg                                              23

<210> SEQ ID NO 190
<211> LENGTH: 23
<212> TYPE: DNA
<213> ORGANISM: Artificial Sequence
<220> FEATURE:
<223> OTHER INFORMATION: OT96

<400> SEQUENCE: 190
gtgacagtgt tgcttgtcga agg                                              23

<210> SEQ ID NO 191
<211> LENGTH: 23
<212> TYPE: DNA
<213> ORGANISM: Artificial Sequence
<220> FEATURE:
<223> OTHER INFORMATION: OT97

<400> SEQUENCE: 191
ataacaacaa tgatcgtcaa agg                                              23

<210> SEQ ID NO 192
<211> LENGTH: 23
<212> TYPE: DNA
<213> ORGANISM: Artificial Sequence
<220> FEATURE:
<223> OTHER INFORMATION: OT98

<400> SEQUENCE: 192
aacactgtga tgtttgtcag agg                                              23

<210> SEQ ID NO 193
<211> LENGTH: 23
<212> TYPE: DNA
<213> ORGANISM: Artificial Sequence
<220> FEATURE:
<223> OTHER INFORMATION: OT99

<400> SEQUENCE: 193
atcacgctga tagtcctcaa agg                                              23

<210> SEQ ID NO 194
<211> LENGTH: 23
<212> TYPE: DNA
<213> ORGANISM: Artificial Sequence
<220> FEATURE:
<223> OTHER INFORMATION: OT100

-continued

<400> SEQUENCE: 194
gtgacaatta tgctcttcaa agg                                           23

<210> SEQ ID NO 195
<211> LENGTH: 23
<212> TYPE: DNA
<213> ORGANISM: Artificial Sequence
<220> FEATURE:
<223> OTHER INFORMATION: Artificial Sequence

<400> SEQUENCE: 195
caaaagactg tcaattccct tgg                                           23

<210> SEQ ID NO 196
<211> LENGTH: 24
<212> TYPE: DNA
<213> ORGANISM: Artificial Sequence
<220> FEATURE:
<223> OTHER INFORMATION: Artificial Sequence

<400> SEQUENCE: 196
caaaagactg tcaattcacc ttgg                                          24

<210> SEQ ID NO 197
<211> LENGTH: 24
<212> TYPE: DNA
<213> ORGANISM: Artificial Sequence
<220> FEATURE:
<223> OTHER INFORMATION: Artificial Sequence

<400> SEQUENCE: 197
caaaagactg tcaattctcc ttgg                                          24

<210> SEQ ID NO 198
<211> LENGTH: 24
<212> TYPE: DNA
<213> ORGANISM: Artificial Sequence
<220> FEATURE:
<223> OTHER INFORMATION: Artificial Sequence

<400> SEQUENCE: 198
caaaagactg tcaattcccc ttgg                                          24

<210> SEQ ID NO 199
<211> LENGTH: 22
<212> TYPE: DNA
<213> ORGANISM: Artificial Sequence
<220> FEATURE:
<223> OTHER INFORMATION: Artificial Sequence

<400> SEQUENCE: 199
caaaagactg tcaattcctt gg                                            22

<210> SEQ ID NO 200
<211> LENGTH: 23
<212> TYPE: DNA
<213> ORGANISM: Artificial Sequence
<220> FEATURE:
<223> OTHER INFORMATION: Artificial Sequence

<400> SEQUENCE: 200
cactaggagc aacacccaac ggg                                           23

<210> SEQ ID NO 201
<211> LENGTH: 24

```
<212> TYPE: DNA
<213> ORGANISM: Artificial Sequence
<220> FEATURE:
<223> OTHER INFORMATION: Artificial Sequence

<400> SEQUENCE: 201
cactaggagc aacacccaaa cggg                                          24

<210> SEQ ID NO 202
<211> LENGTH: 22
<212> TYPE: DNA
<213> ORGANISM: Artificial Sequence
<220> FEATURE:
<223> OTHER INFORMATION: Artificial Sequence

<400> SEQUENCE: 202
cactaggagc aacaccaacg gg                                            22

<210> SEQ ID NO 203
<211> LENGTH: 24
<212> TYPE: DNA
<213> ORGANISM: Artificial Sequence
<220> FEATURE:
<223> OTHER INFORMATION: Artificial Sequence

<400> SEQUENCE: 203
cactaggagc aacaccccaa cggg                                          24

<210> SEQ ID NO 204
<211> LENGTH: 21
<212> TYPE: DNA
<213> ORGANISM: Artificial Sequence
<220> FEATURE:
<223> OTHER INFORMATION: Artificial Sequence

<400> SEQUENCE: 204
cactaggagc aacacaacgg g                                             21

<210> SEQ ID NO 205
<211> LENGTH: 19
<212> TYPE: DNA
<213> ORGANISM: Artificial Sequence
<220> FEATURE:
<223> OTHER INFORMATION: Artificial Sequence

<400> SEQUENCE: 205
cactaggagc aacaacggg                                                19

<210> SEQ ID NO 206
<211> LENGTH: 23
<212> TYPE: DNA
<213> ORGANISM: Artificial Sequence
<220> FEATURE:
<223> OTHER INFORMATION: Artificial Sequence

<400> SEQUENCE: 206
catatagttg ggtcatggca tgg                                           23

<210> SEQ ID NO 207
<211> LENGTH: 22
<212> TYPE: DNA
<213> ORGANISM: Artificial Sequence
<220> FEATURE:
<223> OTHER INFORMATION: Artificial Sequence

<400> SEQUENCE: 207
```

```
catatagttg ggtcatgcat gg                                              22

<210> SEQ ID NO 208
<211> LENGTH: 20
<212> TYPE: DNA
<213> ORGANISM: Artificial Sequence
<220> FEATURE:
<223> OTHER INFORMATION: Artificial Sequence

<400> SEQUENCE: 208
catatagttg ggtcgcatgg                                                 20

<210> SEQ ID NO 209
<211> LENGTH: 19
<212> TYPE: DNA
<213> ORGANISM: Artificial Sequence
<220> FEATURE:
<223> OTHER INFORMATION: Artificial Sequence

<400> SEQUENCE: 209
catatagttg ggcgcatgg                                                  19

<210> SEQ ID NO 210
<211> LENGTH: 18
<212> TYPE: DNA
<213> ORGANISM: Artificial Sequence
<220> FEATURE:
<223> OTHER INFORMATION: Artificial Sequence

<400> SEQUENCE: 210
catatagttg ggtcatgg                                                   18

<210> SEQ ID NO 211
<211> LENGTH: 52
<212> TYPE: DNA
<213> ORGANISM: Artificial Sequence
<220> FEATURE:
<223> OTHER INFORMATION: Artificial Sequence

<400> SEQUENCE: 211
tgcatcgtcc aagcgcacag tggcccggcc tacgacgtca ggttctaccc gg             52

<210> SEQ ID NO 212
<211> LENGTH: 23
<212> TYPE: DNA
<213> ORGANISM: Artificial Sequence
<220> FEATURE:
<223> OTHER INFORMATION: Artificial Sequence

<400> SEQUENCE: 212
tgcatcgtcc aagcgctacc cgg                                             23

<210> SEQ ID NO 213
<211> LENGTH: 52
<212> TYPE: DNA
<213> ORGANISM: Artificial Sequence
<220> FEATURE:
<223> OTHER INFORMATION: Artificial Sequence

<400> SEQUENCE: 213
tgcatcgtcc aagcgcacag tggcccggcc tacgacgtca ggttctaccc gg             52

<210> SEQ ID NO 214
<211> LENGTH: 46
<212> TYPE: DNA
<213> ORGANISM: Artificial Sequence
```

```
<220> FEATURE:
<223> OTHER INFORMATION: Artificial Sequence

<400> SEQUENCE: 214
tttgaaagat ggaagcgcgg tggtgaaact aaactggtcc acacgg          46

<210> SEQ ID NO 215
<211> LENGTH: 24
<212> TYPE: DNA
<213> ORGANISM: Artificial Sequence
<220> FEATURE:
<223> OTHER INFORMATION: Artificial Sequence

<400> SEQUENCE: 215
tttgaaagat ggaagcgcac acgg                                  24

<210> SEQ ID NO 216
<211> LENGTH: 53
<212> TYPE: DNA
<213> ORGANISM: Artificial Sequence
<220> FEATURE:
<223> OTHER INFORMATION: Artificial Sequence

<400> SEQUENCE: 216
gttttaaagc atcacagtga tgctcgtcaa aggatgcctc tcatttatgt caa  53

<210> SEQ ID NO 217
<211> LENGTH: 53
<212> TYPE: DNA
<213> ORGANISM: Artificial Sequence
<220> FEATURE:
<223> OTHER INFORMATION: Artificial Sequence

<400> SEQUENCE: 217
caaaatttcg tagtgtcact acgagcagtt tcctacggag agtaaataca gtt  53

<210> SEQ ID NO 218
<211> LENGTH: 23
<212> TYPE: DNA
<213> ORGANISM: Artificial Sequence
<220> FEATURE:
<223> OTHER INFORMATION: Artificial Sequence

<400> SEQUENCE: 218
atcacagtga tgctcgtcaa agg                                   23

<210> SEQ ID NO 219
<211> LENGTH: 24
<212> TYPE: DNA
<213> ORGANISM: Artificial Sequence
<220> FEATURE:
<223> OTHER INFORMATION: Artificial Sequence

<400> SEQUENCE: 219
atcacagtga tgctcgtcca aagg                                  24

<210> SEQ ID NO 220
<211> LENGTH: 22
<212> TYPE: DNA
<213> ORGANISM: Artificial Sequence
<220> FEATURE:
<223> OTHER INFORMATION: Artificial Sequence

<400> SEQUENCE: 220
atcacagtga tgctcgcaaa gg                                    22
```

```
<210> SEQ ID NO 221
<211> LENGTH: 24
<212> TYPE: DNA
<213> ORGANISM: Artificial Sequence
<220> FEATURE:
<223> OTHER INFORMATION: Artificial Sequence

<400> SEQUENCE: 221
atcacagtga tgctcgtaca aagg                                             24

<210> SEQ ID NO 222
<211> LENGTH: 24
<212> TYPE: DNA
<213> ORGANISM: Artificial Sequence
<220> FEATURE:
<223> OTHER INFORMATION: Artificial Sequence

<400> SEQUENCE: 222
atcacagtga tgctcgtgca aagg                                             24

<210> SEQ ID NO 223
<211> LENGTH: 23
<212> TYPE: DNA
<213> ORGANISM: Artificial Sequence
<220> FEATURE:
<223> OTHER INFORMATION: Artificial Sequence

<400> SEQUENCE: 223
atcacagtga tgctcgtcaa agg                                              23

<210> SEQ ID NO 224
<211> LENGTH: 24
<212> TYPE: DNA
<213> ORGANISM: Artificial Sequence
<220> FEATURE:
<223> OTHER INFORMATION: Artificial Sequence

<400> SEQUENCE: 224
atcacagtga tgctcgtcca aagg                                             24

<210> SEQ ID NO 225
<211> LENGTH: 20
<212> TYPE: DNA
<213> ORGANISM: Artificial Sequence
<220> FEATURE:
<223> OTHER INFORMATION: Artificial Sequence

<400> SEQUENCE: 225
atcacagtga tgctcaaagg                                                  20

<210> SEQ ID NO 226
<211> LENGTH: 24
<212> TYPE: DNA
<213> ORGANISM: Artificial Sequence
<220> FEATURE:
<223> OTHER INFORMATION: Artificial Sequence

<400> SEQUENCE: 226
atcacagtga tgctcgtaca aagg                                             24

<210> SEQ ID NO 227
<211> LENGTH: 24
<212> TYPE: DNA
<213> ORGANISM: Artificial Sequence
<220> FEATURE:
<223> OTHER INFORMATION: Artificial Sequence
```

<400> SEQUENCE: 227
atcacagtga tgctcgtgca aagg    24

<210> SEQ ID NO 228
<211> LENGTH: 23
<212> TYPE: DNA
<213> ORGANISM: Artificial Sequence
<220> FEATURE:
<223> OTHER INFORMATION: Artificial Sequence

<400> SEQUENCE: 228
atcacagtga tgctcgtcaa agg    23

<210> SEQ ID NO 229
<211> LENGTH: 24
<212> TYPE: DNA
<213> ORGANISM: Artificial Sequence
<220> FEATURE:
<223> OTHER INFORMATION: Artificial Sequence

<400> SEQUENCE: 229
atcacagtga tgctcgttca aagg    24

<210> SEQ ID NO 230
<211> LENGTH: 24
<212> TYPE: DNA
<213> ORGANISM: Artificial Sequence
<220> FEATURE:
<223> OTHER INFORMATION: Artificial Sequence

<400> SEQUENCE: 230
atcacagtga tgctcgtaca aagg    24

<210> SEQ ID NO 231
<211> LENGTH: 24
<212> TYPE: DNA
<213> ORGANISM: Artificial Sequence
<220> FEATURE:
<223> OTHER INFORMATION: Artificial Sequence

<400> SEQUENCE: 231
atcacagtga tgctcgtgca aagg    24

<210> SEQ ID NO 232
<211> LENGTH: 24
<212> TYPE: DNA
<213> ORGANISM: Artificial Sequence
<220> FEATURE:
<223> OTHER INFORMATION: Artificial Sequence

<400> SEQUENCE: 232
atcacagtga tgctcgtcca aagg    24

<210> SEQ ID NO 233
<211> LENGTH: 23
<212> TYPE: DNA
<213> ORGANISM: Artificial Sequence
<220> FEATURE:
<223> OTHER INFORMATION: Artificial Sequence

<400> SEQUENCE: 233
atcacagtga tgctcgtcaa agg    23

<210> SEQ ID NO 234

```
<211> LENGTH: 24
<212> TYPE: DNA
<213> ORGANISM: Artificial Sequence
<220> FEATURE:
<223> OTHER INFORMATION: Artificial Sequence

<400> SEQUENCE: 234
atcacagtga tgctcgttca aagg                                              24

<210> SEQ ID NO 235
<211> LENGTH: 24
<212> TYPE: DNA
<213> ORGANISM: Artificial Sequence
<220> FEATURE:
<223> OTHER INFORMATION: Artificial Sequence

<400> SEQUENCE: 235
atcacagtga tgctcgtaca aagg                                              24

<210> SEQ ID NO 236
<211> LENGTH: 20
<212> TYPE: DNA
<213> ORGANISM: Artificial Sequence
<220> FEATURE:
<223> OTHER INFORMATION: Artificial Sequence

<400> SEQUENCE: 236
atcacagtga tgctcaaagg                                                   20

<210> SEQ ID NO 237
<211> LENGTH: 24
<212> TYPE: DNA
<213> ORGANISM: Artificial Sequence
<220> FEATURE:
<223> OTHER INFORMATION: Artificial Sequence

<400> SEQUENCE: 237
atcacagtga tgctcgtgca aagg                                              24

<210> SEQ ID NO 238
<211> LENGTH: 23
<212> TYPE: DNA
<213> ORGANISM: Artificial Sequence
<220> FEATURE:
<223> OTHER INFORMATION: Artificial Sequence

<400> SEQUENCE: 238
atcacagtga tgctcgtcaa agg                                               23

<210> SEQ ID NO 239
<211> LENGTH: 24
<212> TYPE: DNA
<213> ORGANISM: Artificial Sequence
<220> FEATURE:
<223> OTHER INFORMATION: Artificial Sequence

<400> SEQUENCE: 239
atcacagtga tgctcgttca aagg                                              24

<210> SEQ ID NO 240
<211> LENGTH: 24
<212> TYPE: DNA
<213> ORGANISM: Artificial Sequence
<220> FEATURE:
<223> OTHER INFORMATION: Artificial Sequence

<400> SEQUENCE: 240
```

```
atcacagtga tgctcgttca aagg                                          24

<210> SEQ ID NO 241
<211> LENGTH: 20
<212> TYPE: DNA
<213> ORGANISM: Artificial Sequence
<220> FEATURE:
<223> OTHER INFORMATION: Artificial Sequence

<400> SEQUENCE: 241
atcacagtga tgctcaaagg                                               20

<210> SEQ ID NO 242
<211> LENGTH: 24
<212> TYPE: DNA
<213> ORGANISM: Artificial Sequence
<220> FEATURE:
<223> OTHER INFORMATION: Artificial Sequence

<400> SEQUENCE: 242
atcacagtga tgctcgttca aagg                                          24

<210> SEQ ID NO 243
<211> LENGTH: 14
<212> TYPE: DNA
<213> ORGANISM: Artificial Sequence
<220> FEATURE:
<223> OTHER INFORMATION: Artificial Sequence

<400> SEQUENCE: 243
atcacagtca aagg                                                     14

<210> SEQ ID NO 244
<211> LENGTH: 24
<212> TYPE: DNA
<213> ORGANISM: Artificial Sequence
<220> FEATURE:
<223> OTHER INFORMATION: Artificial Sequence

<400> SEQUENCE: 244
atcacagtga tgctcgttca aagg                                          24

<210> SEQ ID NO 245
<211> LENGTH: 23
<212> TYPE: DNA
<213> ORGANISM: Artificial Sequence
<220> FEATURE:
<223> OTHER INFORMATION: Artificial Sequence

<400> SEQUENCE: 245
atcacagtga tgctcgtcaa agg                                           23

<210> SEQ ID NO 246
<211> LENGTH: 24
<212> TYPE: DNA
<213> ORGANISM: Artificial Sequence
<220> FEATURE:
<223> OTHER INFORMATION: Artificial Sequence

<400> SEQUENCE: 246
atcacagtga tgctcgttca aagg                                          24

<210> SEQ ID NO 247
<211> LENGTH: 14
<212> TYPE: DNA
```

```
<213> ORGANISM: Artificial Sequence
<220> FEATURE:
<223> OTHER INFORMATION: Artificial Sequence

<400> SEQUENCE: 247
atcacagtca aagg                                                    14

<210> SEQ ID NO 248
<211> LENGTH: 24
<212> TYPE: DNA
<213> ORGANISM: Artificial Sequence
<220> FEATURE:
<223> OTHER INFORMATION: Artificial Sequence

<400> SEQUENCE: 248
atcacagtga tgctcgttca aagg                                         24

<210> SEQ ID NO 249
<211> LENGTH: 24
<212> TYPE: DNA
<213> ORGANISM: Artificial Sequence
<220> FEATURE:
<223> OTHER INFORMATION: Artificial Sequence

<400> SEQUENCE: 249
atcacagtga tgctcgttca aagg                                         24

<210> SEQ ID NO 250
<211> LENGTH: 21
<212> TYPE: DNA
<213> ORGANISM: Artificial Sequence
<220> FEATURE:
<223> OTHER INFORMATION: Artificial Sequence

<400> SEQUENCE: 250
atcacagtga tgctcgtaag g                                            21

<210> SEQ ID NO 251
<211> LENGTH: 24
<212> TYPE: DNA
<213> ORGANISM: Artificial Sequence
<220> FEATURE:
<223> OTHER INFORMATION: Artificial Sequence

<400> SEQUENCE: 251
atcacagtga tgctcgttca aagg                                         24

<210> SEQ ID NO 252
<211> LENGTH: 24
<212> TYPE: DNA
<213> ORGANISM: Artificial Sequence
<220> FEATURE:
<223> OTHER INFORMATION: Artificial Sequence

<400> SEQUENCE: 252
atcacagtga tgctcgttca aagg                                         24

<210> SEQ ID NO 253
<211> LENGTH: 23
<212> TYPE: DNA
<213> ORGANISM: Artificial Sequence
<220> FEATURE:
<223> OTHER INFORMATION: Artificial Sequence

<400> SEQUENCE: 253
atcacagtga tgctcgtcaa agg                                          23
```

```
<210> SEQ ID NO 254
<211> LENGTH: 24
<212> TYPE: DNA
<213> ORGANISM: Artificial Sequence
<220> FEATURE:
<223> OTHER INFORMATION: Artificial Sequence

<400> SEQUENCE: 254
atcacagtga tgctcgttca aagg                                              24

<210> SEQ ID NO 255
<211> LENGTH: 22
<212> TYPE: DNA
<213> ORGANISM: Artificial Sequence
<220> FEATURE:
<223> OTHER INFORMATION: Artificial Sequence

<400> SEQUENCE: 255
atcacagtga tgctcgcaaa gg                                                22

<210> SEQ ID NO 256
<211> LENGTH: 24
<212> TYPE: DNA
<213> ORGANISM: Artificial Sequence
<220> FEATURE:
<223> OTHER INFORMATION: Artificial Sequence

<400> SEQUENCE: 256
atcacagtga tgctcgttca aagg                                              24

<210> SEQ ID NO 257
<211> LENGTH: 23
<212> TYPE: DNA
<213> ORGANISM: Artificial Sequence
<220> FEATURE:
<223> OTHER INFORMATION: Artificial Sequence

<400> SEQUENCE: 257
atcacagtga tgctcgtcaa agg                                               23

<210> SEQ ID NO 258
<211> LENGTH: 16
<212> TYPE: DNA
<213> ORGANISM: Artificial Sequence
<220> FEATURE:
<223> OTHER INFORMATION: Artificial Sequence

<400> SEQUENCE: 258
atcacagtgt caaagg                                                       16

<210> SEQ ID NO 259
<211> LENGTH: 23
<212> TYPE: DNA
<213> ORGANISM: Artificial Sequence
<220> FEATURE:
<223> OTHER INFORMATION: Artificial Sequence

<400> SEQUENCE: 259
atcacagtga tgctcgtcaa agg                                               23

<210> SEQ ID NO 260
<211> LENGTH: 24
<212> TYPE: DNA
<213> ORGANISM: Artificial Sequence
<220> FEATURE:
```

<223> OTHER INFORMATION: Artificial Sequence

<400> SEQUENCE: 260
atcacagtga tgctcgttca aagg     24

<210> SEQ ID NO 261
<211> LENGTH: 24
<212> TYPE: DNA
<213> ORGANISM: Artificial Sequence
<220> FEATURE:
<223> OTHER INFORMATION: Artificial Sequence

<400> SEQUENCE: 261
atcacagtga tgctcgttca aagg     24

<210> SEQ ID NO 262
<211> LENGTH: 24
<212> TYPE: DNA
<213> ORGANISM: Artificial Sequence
<220> FEATURE:
<223> OTHER INFORMATION: Artificial Sequence

<400> SEQUENCE: 262
atcacagtga tgctcgttca aagg     24

<210> SEQ ID NO 263
<211> LENGTH: 24
<212> TYPE: DNA
<213> ORGANISM: Artificial Sequence
<220> FEATURE:
<223> OTHER INFORMATION: Artificial Sequence

<400> SEQUENCE: 263
atcacagtga tgctcgttca aagg     24

<210> SEQ ID NO 264
<211> LENGTH: 53
<212> TYPE: DNA
<213> ORGANISM: Artificial Sequence
<220> FEATURE:
<223> OTHER INFORMATION: Artificial Sequence

<400> SEQUENCE: 264
gttttaaagc atcacagtga tgctcgtcaa aggatgcctc tcatttatgt caa     53

<210> SEQ ID NO 265
<211> LENGTH: 53
<212> TYPE: DNA
<213> ORGANISM: Artificial Sequence
<220> FEATURE:
<223> OTHER INFORMATION: Artificial Sequence

<400> SEQUENCE: 265
caaaatttcg tagtgtcact acgagcagtt tcctacggag agtaaataca gtt     53

<210> SEQ ID NO 266
<211> LENGTH: 23
<212> TYPE: DNA
<213> ORGANISM: Artificial Sequence
<220> FEATURE:
<223> OTHER INFORMATION: Artificial Sequence

<400> SEQUENCE: 266
atcacagtga tgctcgtcaa agg     23

-continued

```
<210> SEQ ID NO 267
<211> LENGTH: 24
<212> TYPE: DNA
<213> ORGANISM: Artificial Sequence
<220> FEATURE:
<223> OTHER INFORMATION: Artificial Sequence

<400> SEQUENCE: 267
atcacagtga tgctcgtcca aagg                                            24

<210> SEQ ID NO 268
<211> LENGTH: 24
<212> TYPE: DNA
<213> ORGANISM: Artificial Sequence
<220> FEATURE:
<223> OTHER INFORMATION: Artificial Sequence

<400> SEQUENCE: 268
atcacagtga tgctcgttca aagg                                            24

<210> SEQ ID NO 269
<211> LENGTH: 20
<212> TYPE: DNA
<213> ORGANISM: Artificial Sequence
<220> FEATURE:
<223> OTHER INFORMATION: Artificial Sequence

<400> SEQUENCE: 269
atcacagtga tgctcaaagg                                                 20

<210> SEQ ID NO 270
<211> LENGTH: 24
<212> TYPE: DNA
<213> ORGANISM: Artificial Sequence
<220> FEATURE:
<223> OTHER INFORMATION: Artificial Sequence

<400> SEQUENCE: 270
atcacagtga tgctcgttca aagg                                            24

<210> SEQ ID NO 271
<211> LENGTH: 14
<212> TYPE: DNA
<213> ORGANISM: Artificial Sequence
<220> FEATURE:
<223> OTHER INFORMATION: Artificial Sequence

<400> SEQUENCE: 271
atcacagtca aagg                                                       14

<210> SEQ ID NO 272
<211> LENGTH: 24
<212> TYPE: DNA
<213> ORGANISM: Artificial Sequence
<220> FEATURE:
<223> OTHER INFORMATION: Artificial Sequence

<400> SEQUENCE: 272
atcacagtga tgctcgttca aagg                                            24

<210> SEQ ID NO 273
<211> LENGTH: 24
<212> TYPE: DNA
<213> ORGANISM: Artificial Sequence
<220> FEATURE:
<223> OTHER INFORMATION: Artificial Sequence
```

```
<400> SEQUENCE: 273
atcacagtga tgctcgttca aagg                                          24

<210> SEQ ID NO 274
<211> LENGTH: 14
<212> TYPE: DNA
<213> ORGANISM: Artificial Sequence
<220> FEATURE:
<223> OTHER INFORMATION: Artificial Sequence

<400> SEQUENCE: 274
atcacagtca aagg                                                     14

<210> SEQ ID NO 275
<211> LENGTH: 24
<212> TYPE: DNA
<213> ORGANISM: Artificial Sequence
<220> FEATURE:
<223> OTHER INFORMATION: Artificial Sequence

<400> SEQUENCE: 275
atcacagtga tgctcgttca aagg                                          24

<210> SEQ ID NO 276
<211> LENGTH: 24
<212> TYPE: DNA
<213> ORGANISM: Artificial Sequence
<220> FEATURE:
<223> OTHER INFORMATION: Artificial Sequence

<400> SEQUENCE: 276
atcacagtga tgctcgttca aagg                                          24

<210> SEQ ID NO 277
<211> LENGTH: 21
<212> TYPE: DNA
<213> ORGANISM: Artificial Sequence
<220> FEATURE:
<223> OTHER INFORMATION: Artificial Sequence

<400> SEQUENCE: 277
atcacagtga tgctccaaag g                                             21

<210> SEQ ID NO 278
<211> LENGTH: 24
<212> TYPE: DNA
<213> ORGANISM: Artificial Sequence
<220> FEATURE:
<223> OTHER INFORMATION: Artificial Sequence

<400> SEQUENCE: 278
atcacagtga tgctcgttca aagg                                          24

<210> SEQ ID NO 279
<211> LENGTH: 24
<212> TYPE: DNA
<213> ORGANISM: Artificial Sequence
<220> FEATURE:
<223> OTHER INFORMATION: Artificial Sequence

<400> SEQUENCE: 279
atcacagtga tgctcgttca aagg                                          24

<210> SEQ ID NO 280
<211> LENGTH: 24
```

```
<212> TYPE: DNA
<213> ORGANISM: Artificial Sequence
<220> FEATURE:
<223> OTHER INFORMATION: Artificial Sequence

<400> SEQUENCE: 280
atcacagtga tgctcgttca aagg                                          24

<210> SEQ ID NO 281
<211> LENGTH: 22
<212> TYPE: DNA
<213> ORGANISM: Artificial Sequence
<220> FEATURE:
<223> OTHER INFORMATION: Artificial Sequence

<400> SEQUENCE: 281
atcacagtga tgctcgcaaa gg                                            22

<210> SEQ ID NO 282
<211> LENGTH: 24
<212> TYPE: DNA
<213> ORGANISM: Artificial Sequence
<220> FEATURE:
<223> OTHER INFORMATION: Artificial Sequence

<400> SEQUENCE: 282
atcacagtga tgctcgttca aagg                                          24

<210> SEQ ID NO 283
<211> LENGTH: 23
<212> TYPE: DNA
<213> ORGANISM: Artificial Sequence
<220> FEATURE:
<223> OTHER INFORMATION: Artificial Sequence

<400> SEQUENCE: 283
atcacagtga tgctcgtcaa agg                                           23

<210> SEQ ID NO 284
<211> LENGTH: 16
<212> TYPE: DNA
<213> ORGANISM: Artificial Sequence
<220> FEATURE:
<223> OTHER INFORMATION: Artificial Sequence

<400> SEQUENCE: 284
atcacagtgt caaagg                                                   16

<210> SEQ ID NO 285
<211> LENGTH: 23
<212> TYPE: DNA
<213> ORGANISM: Artificial Sequence
<220> FEATURE:
<223> OTHER INFORMATION: Artificial Sequence

<400> SEQUENCE: 285
atcacagtga tgctcgtcaa agg                                           23

<210> SEQ ID NO 286
<211> LENGTH: 24
<212> TYPE: DNA
<213> ORGANISM: Artificial Sequence
<220> FEATURE:
<223> OTHER INFORMATION: Artificial Sequence

<400> SEQUENCE: 286
```
atcacagtga tgctcgttca aagg                                        24

<210> SEQ ID NO 287
<211> LENGTH: 24
<212> TYPE: DNA
<213> ORGANISM: Artificial Sequence
<220> FEATURE:
<223> OTHER INFORMATION: Artificial Sequence

<400> SEQUENCE: 287
atcacagtga tgctcgttca aagg                                        24

<210> SEQ ID NO 288
<211> LENGTH: 24
<212> TYPE: DNA
<213> ORGANISM: Artificial Sequence
<220> FEATURE:
<223> OTHER INFORMATION: Artificial Sequence

<400> SEQUENCE: 288
atcacagtga tgctcgttca aagg                                        24

<210> SEQ ID NO 289
<211> LENGTH: 24
<212> TYPE: DNA
<213> ORGANISM: Artificial Sequence
<220> FEATURE:
<223> OTHER INFORMATION: Artificial Sequence

<400> SEQUENCE: 289
atcacagtga tgctcgttca aagg                                        24

<210> SEQ ID NO 290
<211> LENGTH: 23
<212> TYPE: DNA
<213> ORGANISM: Artificial Sequence
<220> FEATURE:
<223> OTHER INFORMATION: Artificial Sequence

<400> SEQUENCE: 290
gaattcgagc aatacccaac tgg                                         23

<210> SEQ ID NO 291
<211> LENGTH: 23
<212> TYPE: DNA
<213> ORGANISM: Artificial Sequence
<220> FEATURE:
<223> OTHER INFORMATION: Artificial Sequence

<400> SEQUENCE: 291
aactgggaac atcacccaat agg                                         23

<210> SEQ ID NO 292
<211> LENGTH: 23
<212> TYPE: DNA
<213> ORGANISM: Artificial Sequence
<220> FEATURE:
<223> OTHER INFORMATION: Artificial Sequence

<400> SEQUENCE: 292
caccaggagc aatatcaaac tgg                                         23

<210> SEQ ID NO 293
<211> LENGTH: 23
<212> TYPE: DNA
<213> ORGANISM: Artificial Sequence

```
<220> FEATURE:
<223> OTHER INFORMATION: Artificial Sequence

<400> SEQUENCE: 293
cactaggagc aacacccaac ggg                                               23

<210> SEQ ID NO 294
<211> LENGTH: 23
<212> TYPE: DNA
<213> ORGANISM: Artificial Sequence
<220> FEATURE:
<223> OTHER INFORMATION: Artificial Sequence

<400> SEQUENCE: 294
tttggaaaag ggtagcgcgg tgg                                               23

<210> SEQ ID NO 295
<211> LENGTH: 23
<212> TYPE: DNA
<213> ORGANISM: Artificial Sequence
<220> FEATURE:
<223> OTHER INFORMATION: Artificial Sequence

<400> SEQUENCE: 295
tttgaaaaag agaagcgtgg tgg                                               23

<210> SEQ ID NO 296
<211> LENGTH: 23
<212> TYPE: DNA
<213> ORGANISM: Artificial Sequence
<220> FEATURE:
<223> OTHER INFORMATION: Artificial Sequence

<400> SEQUENCE: 296
tttggaagat ggaagctatg tgg                                               23

<210> SEQ ID NO 297
<211> LENGTH: 23
<212> TYPE: DNA
<213> ORGANISM: Artificial Sequence
<220> FEATURE:
<223> OTHER INFORMATION: Artificial Sequence

<400> SEQUENCE: 297
attaaaggtt ggaagcgcgg cgg                                               23

<210> SEQ ID NO 298
<211> LENGTH: 23
<212> TYPE: DNA
<213> ORGANISM: Artificial Sequence
<220> FEATURE:
<223> OTHER INFORMATION: Artificial Sequence

<400> SEQUENCE: 298
tttgaaggat ggattcgctg cgg                                               23

<210> SEQ ID NO 299
<211> LENGTH: 23
<212> TYPE: DNA
<213> ORGANISM: Artificial Sequence
<220> FEATURE:
<223> OTHER INFORMATION: Artificial Sequence

<400> SEQUENCE: 299
tttgaaacat ggaagcacga agg                                               23
```

```
<210> SEQ ID NO 300
<211> LENGTH: 23
<212> TYPE: DNA
<213> ORGANISM: Artificial Sequence
<220> FEATURE:
<223> OTHER INFORMATION: Artificial Sequence

<400> SEQUENCE: 300
tttgaaagat ggaagcgcgg tgg                                              23

<210> SEQ ID NO 301
<211> LENGTH: 23
<212> TYPE: DNA
<213> ORGANISM: Artificial Sequence
<220> FEATURE:
<223> OTHER INFORMATION: Artificial Sequence

<400> SEQUENCE: 301
tgtaacaaaa ctggtcaacc agg                                              23

<210> SEQ ID NO 302
<211> LENGTH: 23
<212> TYPE: DNA
<213> ORGANISM: Artificial Sequence
<220> FEATURE:
<223> OTHER INFORMATION: Artificial Sequence

<400> SEQUENCE: 302
tagatctgaa ctggtccaca ggg                                              23

<210> SEQ ID NO 303
<211> LENGTH: 23
<212> TYPE: DNA
<213> ORGANISM: Artificial Sequence
<220> FEATURE:
<223> OTHER INFORMATION: Artificial Sequence

<400> SEQUENCE: 303
tgtaagtaaa ttggtccgca tgg                                              23

<210> SEQ ID NO 304
<211> LENGTH: 23
<212> TYPE: DNA
<213> ORGANISM: Artificial Sequence
<220> FEATURE:
<223> OTHER INFORMATION: Artificial Sequence

<400> SEQUENCE: 304
tgaaactaga ctggtcaaca agg                                              23

<210> SEQ ID NO 305
<211> LENGTH: 23
<212> TYPE: DNA
<213> ORGANISM: Artificial Sequence
<220> FEATURE:
<223> OTHER INFORMATION: Artificial Sequence

<400> SEQUENCE: 305
tgaaactaaa ctggtccaca cgg                                              23

<210> SEQ ID NO 306
<211> LENGTH: 849
<212> TYPE: DNA
<213> ORGANISM: Artificial Sequence
<220> FEATURE:
<223> OTHER INFORMATION: Artificial Sequence
```

<400> SEQUENCE: 306

```
gtcactgggc acatcatctc caccacaatt ggaggcaaga atggagaacc aaaacagact    60
gtgagttaca tggcagagcg tgtggtaggg gctggatctt ttggaattgt tttccaggca   120
aaatgtctag aaacggggga aactgtggct ataaaaaagg ttttacaaga caaaagatac   180
aagaatcgtg agttgcagtt gatgagaaca atggatcatc caaatgtggt ttctttgaag   240
cattgtttct attcaactac aagcaaagat gagcttttc tcaatctggt tatggaatat    300
gtcccagaga caattttcg ggttttaaag catcacagtg atgctcgtca aggatgcct    360
ctcatttatg tcaaactata cacatatcaa atatttaggg ggctagcata catgcatatg   420
gttgctggag catgccacag ggacttgaag cctcagaatg tcctggttga tcctcttact   480
caccaagtca agatctgcga ctttggaagc gcaaaaatgc tagtgagggg agaagcaaat   540
atatcatata tttgttctcg ttttatcgg gccccagaac ttatctttgg tgctactgag    600
tatacaactt cgattgatat atggtcggct ggttgcattc ttgctgagct tcttttgggg   660
cagccactat ttcccggaga aaatgcagtg gatcagcttg tggagattat taaggttctg   720
ggcacgccaa cgcgagaaga acttcgatgt atgaatccca actacactga ttttaggttt   780
cctcaagtaa aggcacaccc ttggcacaag gtatttcata agcggatgcc cccggaagcg   840
attgactta                                                           849
```

<210> SEQ ID NO 307
<211> LENGTH: 283
<212> TYPE: PRT
<213> ORGANISM: Artificial Sequence
<220> FEATURE:
<223> OTHER INFORMATION: Artificial Sequence

<400> SEQUENCE: 307

```
Val Thr Gly His Ile Ile Ser Thr Thr Ile Gly Gly Lys Asn Gly Glu
1               5                   10                  15
Pro Lys Gln Thr Val Ser Tyr Met Ala Glu Arg Val Val Gly Ala Gly
            20                  25                  30
Ser Phe Gly Ile Val Phe Gln Ala Lys Cys Leu Glu Thr Gly Glu Thr
        35                  40                  45
Val Ala Ile Lys Lys Val Leu Gln Asp Lys Arg Tyr Lys Asn Arg Glu
    50                  55                  60
Leu Gln Leu Met Arg Thr Met Asp His Pro Asn Val Val Ser Leu Lys
65                  70                  75                  80
His Cys Phe Tyr Ser Thr Thr Ser Lys Asp Glu Leu Phe Leu Asn Leu
                85                  90                  95
Val Met Glu Tyr Val Pro Glu Thr Ile Phe Arg Val Leu Lys His His
            100                 105                 110
Ser Asp Ala Arg Gln Arg Met Pro Leu Ile Tyr Val Lys Leu Tyr Thr
        115                 120                 125
Tyr Gln Ile Phe Arg Gly Leu Ala Tyr Met His Met Val Ala Gly Ala
    130                 135                 140
Cys His Arg Asp Leu Lys Pro Gln Asn Val Leu Val Asp Pro Leu Thr
145                 150                 155                 160
His Gln Val Lys Ile Cys Asp Phe Gly Ser Ala Lys Met Leu Val Arg
                165                 170                 175
Gly Glu Ala Asn Ile Ser Tyr Ile Cys Ser Arg Phe Tyr Arg Ala Pro
            180                 185                 190
```

```
Glu Leu Ile Phe Gly Ala Thr Glu Tyr Thr Thr Ser Ile Asp Ile Trp
            195                 200                 205

Ser Ala Gly Cys Ile Leu Ala Glu Leu Leu Gly Gln Pro Leu Phe
        210                 215                 220

Pro Gly Glu Asn Ala Val Asp Gln Leu Val Glu Ile Ile Lys Val Leu
225                 230                 235                 240

Gly Thr Pro Thr Arg Glu Glu Leu Arg Cys Met Asn Pro Asn Tyr Thr
                245                 250                 255

Asp Phe Arg Phe Pro Gln Val Lys Ala His Pro Trp His Lys Val Phe
                260                 265                 270

His Lys Arg Met Pro Pro Glu Ala Ile Asp Leu
                275                 280
```

<210> SEQ ID NO 308
<211> LENGTH: 23
<212> TYPE: DNA
<213> ORGANISM: Artificial Sequence
<220> FEATURE:
<223> OTHER INFORMATION: Artificial Sequence

<400> SEQUENCE: 308
atcacagtga tgctcgtcaa agg                                          23

<210> SEQ ID NO 309
<211> LENGTH: 24
<212> TYPE: DNA
<213> ORGANISM: Artificial Sequence
<220> FEATURE:
<223> OTHER INFORMATION: Artificial Sequence

<400> SEQUENCE: 309
atcacagtga tgctcgttca aagg                                         24

<210> SEQ ID NO 310
<211> LENGTH: 23
<212> TYPE: DNA
<213> ORGANISM: Artificial Sequence
<220> FEATURE:
<223> OTHER INFORMATION: Artificial Sequence

<400> SEQUENCE: 310
atcacagtga tgctcgtcaa agg                                          23

<210> SEQ ID NO 311
<211> LENGTH: 24
<212> TYPE: DNA
<213> ORGANISM: Artificial Sequence
<220> FEATURE:
<223> OTHER INFORMATION: Artificial Sequence

<400> SEQUENCE: 311
atcacagtga tgctcgttca aagg                                         24

<210> SEQ ID NO 312
<211> LENGTH: 23
<212> TYPE: DNA
<213> ORGANISM: Artificial Sequence
<220> FEATURE:
<223> OTHER INFORMATION: Artificial Sequence

<400> SEQUENCE: 312
atcacagtga tgctcgtcaa agg                                          23

```
<210> SEQ ID NO 313
<211> LENGTH: 24
<212> TYPE: DNA
<213> ORGANISM: Artificial Sequence
<220> FEATURE:
<223> OTHER INFORMATION: Artificial Sequence

<400> SEQUENCE: 313
atcacagtga tgctcgttca aagg                                              24

<210> SEQ ID NO 314
<211> LENGTH: 23
<212> TYPE: DNA
<213> ORGANISM: Artificial Sequence
<220> FEATURE:
<223> OTHER INFORMATION: Artificial Sequence

<400> SEQUENCE: 314
atcacagtga tgctcgtcaa agg                                               23

<210> SEQ ID NO 315
<211> LENGTH: 14
<212> TYPE: DNA
<213> ORGANISM: Artificial Sequence
<220> FEATURE:
<223> OTHER INFORMATION: Artificial Sequence

<400> SEQUENCE: 315
atcacagtca aagg                                                         14

<210> SEQ ID NO 316
<211> LENGTH: 24
<212> TYPE: DNA
<213> ORGANISM: Artificial Sequence
<220> FEATURE:
<223> OTHER INFORMATION: Artificial Sequence

<400> SEQUENCE: 316
atcacagtga tgctcgttca aagg                                              24

<210> SEQ ID NO 317
<211> LENGTH: 23
<212> TYPE: DNA
<213> ORGANISM: Artificial Sequence
<220> FEATURE:
<223> OTHER INFORMATION: Artificial Sequence

<400> SEQUENCE: 317
atcacagtga tgctcgtcaa agg                                               23

<210> SEQ ID NO 318
<211> LENGTH: 24
<212> TYPE: DNA
<213> ORGANISM: Artificial Sequence
<220> FEATURE:
<223> OTHER INFORMATION: Artificial Sequence

<400> SEQUENCE: 318
atcacagtga tgctcgttca aagg                                              24

<210> SEQ ID NO 319
<211> LENGTH: 23
<212> TYPE: DNA
<213> ORGANISM: Artificial Sequence
<220> FEATURE:
<223> OTHER INFORMATION: Artificial Sequence
```

```
<400> SEQUENCE: 319
atcacagtga tgctcgtcaa agg                                           23

<210> SEQ ID NO 320
<211> LENGTH: 14
<212> TYPE: DNA
<213> ORGANISM: Artificial Sequence
<220> FEATURE:
<223> OTHER INFORMATION: Artificial Sequence

<400> SEQUENCE: 320
atcacagtca aagg                                                     14

<210> SEQ ID NO 321
<211> LENGTH: 24
<212> TYPE: DNA
<213> ORGANISM: Artificial Sequence
<220> FEATURE:
<223> OTHER INFORMATION: Artificial Sequence

<400> SEQUENCE: 321
atcacagtga tgctcgttca aagg                                          24

<210> SEQ ID NO 322
<211> LENGTH: 23
<212> TYPE: DNA
<213> ORGANISM: Artificial Sequence
<220> FEATURE:
<223> OTHER INFORMATION: Artificial Sequence

<400> SEQUENCE: 322
atcacagtga tgctcgtcaa agg                                           23

<210> SEQ ID NO 323
<211> LENGTH: 23
<212> TYPE: DNA
<213> ORGANISM: Artificial Sequence
<220> FEATURE:
<223> OTHER INFORMATION: Artificial Sequence

<400> SEQUENCE: 323
atcacagtga tgctcgtcaa agg                                           23

<210> SEQ ID NO 324
<211> LENGTH: 23
<212> TYPE: DNA
<213> ORGANISM: Artificial Sequence
<220> FEATURE:
<223> OTHER INFORMATION: Artificial Sequence

<400> SEQUENCE: 324
atcacagtga tgctcgtcaa agg                                           23

<210> SEQ ID NO 325
<211> LENGTH: 24
<212> TYPE: DNA
<213> ORGANISM: Artificial Sequence
<220> FEATURE:
<223> OTHER INFORMATION: Artificial Sequence

<400> SEQUENCE: 325
atcacagtga tgctcgttca aagg                                          24

<210> SEQ ID NO 326
<211> LENGTH: 23
```

-continued

<212> TYPE: DNA
<213> ORGANISM: Artificial Sequence
<220> FEATURE:
<223> OTHER INFORMATION: Artificial Sequence

<400> SEQUENCE: 326
atcacagtga tgctcgtcaa agg                                              23

<210> SEQ ID NO 327
<211> LENGTH: 24
<212> TYPE: DNA
<213> ORGANISM: Artificial Sequence
<220> FEATURE:
<223> OTHER INFORMATION: Artificial Sequence

<400> SEQUENCE: 327
atcacagtga tgctcgttca aagg                                             24

<210> SEQ ID NO 328
<211> LENGTH: 21
<212> TYPE: DNA
<213> ORGANISM: Artificial Sequence
<220> FEATURE:
<223> OTHER INFORMATION: Artificial Sequence

<400> SEQUENCE: 328
atcacagtga tgctcgtaag g                                                21

<210> SEQ ID NO 329
<211> LENGTH: 23
<212> TYPE: DNA
<213> ORGANISM: Artificial Sequence
<220> FEATURE:
<223> OTHER INFORMATION: Artificial Sequence

<400> SEQUENCE: 329
atcacagtga tgctcgtcaa agg                                              23

<210> SEQ ID NO 330
<211> LENGTH: 24
<212> TYPE: DNA
<213> ORGANISM: Artificial Sequence
<220> FEATURE:
<223> OTHER INFORMATION: Artificial Sequence

<400> SEQUENCE: 330
atcacagtga tgctcgttca aagg                                             24

<210> SEQ ID NO 331
<211> LENGTH: 23
<212> TYPE: DNA
<213> ORGANISM: Artificial Sequence
<220> FEATURE:
<223> OTHER INFORMATION: Artificial Sequence

<400> SEQUENCE: 331
atcacagtga tgctcgtcaa agg                                              23

<210> SEQ ID NO 332
<211> LENGTH: 24
<212> TYPE: DNA
<213> ORGANISM: Artificial Sequence
<220> FEATURE:
<223> OTHER INFORMATION: Artificial Sequence

<400> SEQUENCE: 332

```
atcacagtga tgctcgttca aagg                                           24

<210> SEQ ID NO 333
<211> LENGTH: 22
<212> TYPE: DNA
<213> ORGANISM: Artificial Sequence
<220> FEATURE:
<223> OTHER INFORMATION: Artificial Sequence

<400> SEQUENCE: 333
atcacagtga tgctcgcaaa gg                                             22

<210> SEQ ID NO 334
<211> LENGTH: 23
<212> TYPE: DNA
<213> ORGANISM: Artificial Sequence
<220> FEATURE:
<223> OTHER INFORMATION: Artificial Sequence

<400> SEQUENCE: 334
atcacagtga tgctcgtcaa agg                                            23

<210> SEQ ID NO 335
<211> LENGTH: 23
<212> TYPE: DNA
<213> ORGANISM: Artificial Sequence
<220> FEATURE:
<223> OTHER INFORMATION: Artificial Sequence

<400> SEQUENCE: 335
atcacagtga tgctcgtcaa agg                                            23

<210> SEQ ID NO 336
<211> LENGTH: 24
<212> TYPE: DNA
<213> ORGANISM: Artificial Sequence
<220> FEATURE:
<223> OTHER INFORMATION: Artificial Sequence

<400> SEQUENCE: 336
atcacagtga tgctcgttca aagg                                           24

<210> SEQ ID NO 337
<211> LENGTH: 23
<212> TYPE: DNA
<213> ORGANISM: Artificial Sequence
<220> FEATURE:
<223> OTHER INFORMATION: Artificial Sequence

<400> SEQUENCE: 337
atcacagtga tgctcgtcaa agg                                            23

<210> SEQ ID NO 338
<211> LENGTH: 23
<212> TYPE: DNA
<213> ORGANISM: Artificial Sequence
<220> FEATURE:
<223> OTHER INFORMATION: Artificial Sequence

<400> SEQUENCE: 338
atcacagtga tgctcgtcaa agg                                            23

<210> SEQ ID NO 339
<211> LENGTH: 23
<212> TYPE: DNA
<213> ORGANISM: Artificial Sequence
```

```
<220> FEATURE:
<223> OTHER INFORMATION: Artificial Sequence

<400> SEQUENCE: 339
atcacagtga tgctcgtcaa agg                                              23

<210> SEQ ID NO 340
<211> LENGTH: 16
<212> TYPE: DNA
<213> ORGANISM: Artificial Sequence
<220> FEATURE:
<223> OTHER INFORMATION: Artificial Sequence

<400> SEQUENCE: 340
atcacagtgt caaagg                                                      16

<210> SEQ ID NO 341
<211> LENGTH: 23
<212> TYPE: DNA
<213> ORGANISM: Artificial Sequence
<220> FEATURE:
<223> OTHER INFORMATION: Artificial Sequence

<400> SEQUENCE: 341
atcacagtga tgctcgtcaa agg                                              23

<210> SEQ ID NO 342
<211> LENGTH: 23
<212> TYPE: DNA
<213> ORGANISM: Artificial Sequence
<220> FEATURE:
<223> OTHER INFORMATION: Artificial Sequence

<400> SEQUENCE: 342
atcacagtga tgctcgtcaa agg                                              23

<210> SEQ ID NO 343
<211> LENGTH: 24
<212> TYPE: DNA
<213> ORGANISM: Artificial Sequence
<220> FEATURE:
<223> OTHER INFORMATION: Artificial Sequence

<400> SEQUENCE: 343
atcacagtga tgctcgttca aagg                                             24

<210> SEQ ID NO 344
<211> LENGTH: 23
<212> TYPE: DNA
<213> ORGANISM: Artificial Sequence
<220> FEATURE:
<223> OTHER INFORMATION: Artificial Sequence

<400> SEQUENCE: 344
atcacagtga tgctcgtcaa agg                                              23

<210> SEQ ID NO 345
<211> LENGTH: 24
<212> TYPE: DNA
<213> ORGANISM: Artificial Sequence
<220> FEATURE:
<223> OTHER INFORMATION: Artificial Sequence

<400> SEQUENCE: 345
atcacagtga tgctcgttca aagg                                             24
```

```
<210> SEQ ID NO 346
<211> LENGTH: 23
<212> TYPE: DNA
<213> ORGANISM: Artificial Sequence
<220> FEATURE:
<223> OTHER INFORMATION: Artificial Sequence

<400> SEQUENCE: 346
atcacagtga tgctcgtcaa agg                                              23

<210> SEQ ID NO 347
<211> LENGTH: 24
<212> TYPE: DNA
<213> ORGANISM: Artificial Sequence
<220> FEATURE:
<223> OTHER INFORMATION: Artificial Sequence

<400> SEQUENCE: 347
atcacagtga tgctcgttca aagg                                             24

<210> SEQ ID NO 348
<211> LENGTH: 23
<212> TYPE: DNA
<213> ORGANISM: Artificial Sequence
<220> FEATURE:
<223> OTHER INFORMATION: Artificial Sequence

<400> SEQUENCE: 348
atcacagtga tgctcgtcaa agg                                              23

<210> SEQ ID NO 349
<211> LENGTH: 24
<212> TYPE: DNA
<213> ORGANISM: Artificial Sequence
<220> FEATURE:
<223> OTHER INFORMATION: Artificial Sequence

<400> SEQUENCE: 349
atcacagtga tgctcgttca aagg                                             24

<210> SEQ ID NO 350
<211> LENGTH: 23
<212> TYPE: DNA
<213> ORGANISM: Artificial Sequence
<220> FEATURE:
<223> OTHER INFORMATION: Artificial Sequence

<400> SEQUENCE: 350
atcacagtga tgctcgtcaa agg                                              23

<210> SEQ ID NO 351
<211> LENGTH: 24
<212> TYPE: DNA
<213> ORGANISM: Artificial Sequence
<220> FEATURE:
<223> OTHER INFORMATION: Artificial Sequence

<400> SEQUENCE: 351
atcacagtga tgctcgttca aagg                                             24
```